(12) United States Patent
Kumar et al.

(10) Patent No.: US 9,708,618 B2
(45) Date of Patent: Jul. 18, 2017

(54) CONSTRUCTS FOR EXPRESSING TRANSGENES USING REGULATORY ELEMENTS FROM BRACHYPODIUM UBIQUITIN GENES

(71) Applicant: Dow AgroSciences, LLC, Indianapolis, IN (US)

(72) Inventors: Sandeep Kumar, Carmel, IN (US); Jeffrey Beringer, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/472,965

(22) Filed: Aug. 29, 2014

(65) Prior Publication Data

US 2015/0067925 A1   Mar. 5, 2015

Related U.S. Application Data

(60) Provisional application No. 61/872,134, filed on Aug. 30, 2013.

(51) Int. Cl.
*C12N 15/82* (2006.01)
*C07K 14/415* (2006.01)

(52) U.S. Cl.
CPC ........ *C12N 15/8216* (2013.01); *C07K 14/415* (2013.01)

(58) Field of Classification Search
None
See application file for complete search history.

(56) References Cited

U.S. PATENT DOCUMENTS

| | | |
|---|---|---|
| 2002/0046415 A1 | 4/2002 | Albert et al. |
| 2003/0066108 A1 | 4/2003 | Jilka et al. |
| 2007/0243543 A1 | 10/2007 | Song et al. |
| 2009/0007301 A1 | 1/2009 | Wintz et al. |
| 2010/0199377 A1 | 8/2010 | Sekar et al. |
| 2012/0180158 A1 | 7/2012 | Abbitt |

FOREIGN PATENT DOCUMENTS

| | | |
|---|---|---|
| EP | 0342926 | 11/1989 |
| WO | WO 2009/109054 | 9/2009 |
| WO | WO 2010/146046 | 12/2010 |
| WO | WO 2012/159891 | 11/2012 |
| WO | WO 2013/101343 | 7/2013 |
| WO | WO 2014/039872 | 3/2014 |

OTHER PUBLICATIONS

Potenza et al., In Vitro Cell Dev Biol Plant 40:1-22 (2004).*
Saha et al., In Silico Biol 7(1):7-19 (2007).*
Loke et al., Plant Physiol 138:1457-68 (2005).*
Donald & Cashmore, EMBO J 9:1717-26 (1990).*
Kim et al., Plant Mol Biol 24:105-17 (1994).*
Dolferus et al., Plant Physiol 105:1075-87 (1994).*
PCT International Search Report and Written Opinion for PCT/US2014/053328 completed by the US Searching Authority on Dec. 23, 2014.
Wen Jing Li et al, "Evaluation of seed storage protein gene 3'-untranslated regions in enhancing gene expression in transgenic rice seed," Transgenic Research, Kluwer Academic Publishers—Plenum Publishers, NE, vol. 21, No. 3, Sep. 13, 2011 pp. 545-553.
Christensen et al "Ubiquitin Promoter-Based Vectors for High-Level Expression of Selectable and/or Screenable Marker Genes in Monocotyledonous Plants," Transgenic Research, Springer Netherlands, NL, vol. 5, No. 3, Jan. 1, 1996, pp. 213-218.

* cited by examiner

*Primary Examiner* — Cathy Kingdon Worley
*Assistant Examiner* — Russell Boggs
(74) *Attorney, Agent, or Firm* — Eric J. Kraus; Barnes & Thornburg LLP

(57) ABSTRACT

Provided are constructs and methods for expressing a transgene in plant cells and/or plant tissues using the regulatory elements, including the promoters and/or 3'-UTRs, isolated from *Brachypodium distachyon* ubiquitin genes.

26 Claims, 50 Drawing Sheets

Fig. 35 ctgctcgttcagcccacagtaacacgccgtgcgacatgcagatgccctccaccacgccgaccaacccaagt
ccgccgcgctcgtccacggcgccatccgcatccgcgcgtcaacgtcatccggaggaggcgagcgcgatgtcg
acggccacggcggcggcggacacgacggcgacgccccgactccgcgcgcgcgtcaaggctgcagtggcgtcg
tggtggccgtccgcctgcacgagatccccgcgtggacgagcgccgcctccacccagcccctatatcgagaaa
tcaacggtgggctcgagctcctcagcaacctccccacccccttccgaccacgctccttccccgtgccc
ctcttctccgtaaaccgagccgccgagaacaacaccaacgaaagggcgaagagaatcgccatagagaggag
atgggcggaggcggatagtttcagccattcacggagaaatggggaggagagaacacgacatcatacggacgc
gaccctctagctggctggctgtcctaaagaatcgaacggaatcgctgcgccaggagaaaacgaacggtcctg
aagcatgtgcgccggttcttccaaaacacttatctttaagattgaagtagtatatatgactgaaattttta
caaggttttccccataaaacaggtgagcttatctcatccttttgtttaggatgtacgtattatatatgact
gaatatttttattttcattgaatgaagattttcgacccccaaaaataaaaaacggaggagtacctttgt
gccgtgtatatggactagagccatcgggacgtttccggagactgcgtggtggggcgatggacgcacaacga
ccgcatttcggttgccgactcgccgttcgcatctggtaggcacgactcgtcgggttcggctcttgcgtgag
ccgtgacgtaacagacccgttctcttccccgtctggccatccataaatccccctccatcggcttcccttt
cctcaatccagcaccctgattCCGATCGAAAAGTCCCCGCAAGAGCAAGCGACCGATCTCGTGAATCTCCGT
CAAGgtatgcagcctcgcttcctcctcgctaccgtttcaattctggagtaggtcgtagaggataccatgttg
atttgacagagggagtagattagatacttgtagatcgaagtgcggatgttccatggtagatgataccatgtt
gatttcgattagatcggattaaatctttgtagatcgaagtgcgcatgttccatgaattgcctgttaccagta
gattcaagttttctgtgttatagaggtgggatctactcgttgagatgattagctcctagaggacaccatgc
cgttttggaaaatagatcagaaccgtgtagatcgatgtgagcatgtgttcctgtagatccaagttcttcgc
atgttactagttgtgatctattgtttgtgaatacgctctcgatctatccgtgtagatttcactcgattact
gttactgtggcttgatcgttcatagttgttcgttaggtttgatcgaacagtgtctgaacctaattggatatg
tattcttgatctatcaacgtgtaggtttcagtcatgtatttatgtactccctccgtcccaaattaactgacg
tggattttgtataagaatctatacaaatccatgtcagttaattcgggatggagtaccatattcaataatttg
tttattgctgtccacttatgtaccatatgtttgttgttcctcatgtggattctactaattatcattgattgg
tgatcttctattttgctagtttcctagctcaatctggttattcatgtagatgtgttgttgaaatcggagacc
atgcttgttattagatagtttattgcttatcagtttcatgttctggttgatgcaacacatattcatgttcgc
tatctggttgctgcttgatattctctgatttacattcattataagaatatattctgctctggttgttgcttc
tcatgactttacctactcggtaggtgacttacctttggtttacaattgtcaactatgcagATGcagatctt
tgtgaagaccctcaccggcaagaccatcaccttgaggtcgagtcttctgatacgatcgacaatgtcaaggc
aaagatccaggacaaggagggcatcccccggaccagcagcgtctcatcttcgccgggaagcagctggagga
tggccgcaccctggcagattacaacatccagaaggagtccaccctccatctggtgctcaggctcaggggtgg
catgcaaatctttgtgaagaccttactggcaagaccatcacactcgaggtcgagtcgtctgacacgatcga
caatgtgaaggcaaagatccaggacaaggagggcatcccccagaccagcagcgcctcatctttgctggcaa
gcaactggaagacggtcgcaccctggcagattacaatatccagaaggagtccaccttgcaccttgtgcttcg
cctccgtggtggcatgcaaatctttgtcaagaccttgacaggcaagaccattactctggaggtcgagtcgtc
tgacacaatcgataatgtgaaggcgaagatccaggacaaggagggaattccaccggaccagcagcgcctaat
ctttgctggcaaacagcttgaggatggccgcaccctggcagattacaacatccagaaagaatccactctgca
cctggtgcttcgcctccgtggtggcatgcagatctttgtcaagaccttgacagggaagacaatcacactgga
ggtcgagtcgtctgacacaatcgataatgtgaaggcgaagatccaggacaaggagggcattccaccggacca
gcagcgccttatcttcgccggcaagcagcttgaggatggccgcaccttgctgattacaatatccagaagga

Fig. 35 cont.

*atccaccctgcacctggtgcttcgcctccgtggtggcatgcagatctttgtcaagactttgaccgggaagac*
*cattacactggaggttgaatcttcagacaccatcgacaacgtgaaggcgaagatccaggacaaggagggcat*
*cccccagaccagcagcgcctgatctttgctggtaagcagcttgaggatggacgcactctggcggattataa*
*catccagaaggagtctaccctacacctggtgctccgcctccgtggtggccagTAAgtttgtcaaaaactggc*
*ctacagtctgctgcccctgttggtctgcccttggaagtagtcgtgtctatggttatgtgagaagtcgttgt*
*gttctttctaatcccgtactgtttgtgtgaacatctgctgctgtcgtattgcatcgtgaagaatcctgttat*
*gaataagtgaacatgaaccttgttctgtgattacggcttcgtggttatgcgaacgttcttacaaacgcaatt*
*gcacctgatgtaaaatcgttttgctagctgtatggaacaagtgctcatgatgttcatgcaagatgcaattc*
*cagcttttgttggtttgtcatctttgtactgtgcttaccgcacataaagattgcatcttgcttattgctttg*
*ttgctttggtgctcgtccgcttctccttgcaccttatcaaacctttgtttagattctcttcttatagcactt*
*ggtaactctcagctttacaacgccagtactgtttctgaaatttcatgactgataaagctgatagatggagta*
*ctaatatatgacatctttccataaatgttcgggtgcagagatatggaggccccaggatcctatttacaggat*
*gaacctacctgggccgctgtacgcatgacatccgcgagcaagtctgaggttctcaatgtacacatgaaattg*
*attttgctgcgtttggcttggctgatcgttgcatttgttctgattcatcagagttaaataacggatatatc*
*agcaaatatccgcagcatccacaccgaccacacgtccggttaacagagtcccctgccttgctttaattatt*
*acggagtactccgctattaatccttagatatgtttcgaaggaactcaaaccttcctccatctgcaaatctca*
*gtgcttcaaaactggaattagataattgaaccttcattcggttgcaattcacaactgcaaattgaacagca*
*ctgtcaatttcaatttcggggttcacgattccaccgataggttgacatgatccatgatccacccattgtacaa*
*c (SEQ ID NO:19)*

Fig. 36 ggcgtcaggactggcgaagtctggactctgcagggccgaactgctgaagacgaagcagaggaagagaaaggg
aagtgttcgacttgtaatttgtaggggttttttttagaggaacttgtaatttgtaggtgggctggcctcgtt
ggaaaaacgatgctggctggttgggctgggccgatgtacgcttgcaaacaacttgtggcggcccgttctgga
cgagcaggagtttctttttttgttctcacttttctggtcttctttagttacggagtaccttttgtttttaaa
ggagttacctttttttaggaattctttagttacctttcgcttgctctcaaaaaatatttaactttcgcttt
ttttcattttaattttttgcaactatttacgagtttcatgaatgcttattttccagcatatcattatttgcaa
gtattttatgccgtatgtattggacgagagccatcgggactgttccagagactgcgtggtggggacggctc
ccaaccgccttttctatctctgttcgcatccggtggccgacttggctcgcgcgtgagccgtgacgtaacaga
cttggtctcttcccatctggccatctataaattcccccatcgatcgaccctccctttccCCAATCCAGCAC
CCCCGATCCCGATCGAAAATTCTCCGCAACAGCAAGCGATCGATCTAGCGAATCCCCGTCAAGgtatgtagc
ctctcgattcctcctcagccctgccctcgatttggtgtacgcgttgagatgatgatctcgtagatgtctaga
tgacaccatgtcgatttgaaatagatcagatccgtgtagatcgatgagctcctgtgtacctgtggattcaag
ttattttcgcatgctattgttgtgatctactagatctagtgtgtgtattctatgctatcgatttctccgtgt
agatttcactcgattactgttactgtggcttgatcggccatagatgttggttaaggtttgatcggttagtgt
tgaacctgcgtggatatctagcatccatctattatcgtgtaggtttcgaacaaacaagcactattattgta
ctgatggttcgtctatggttggttttgaccgttttagtgttgaacgagccttctgtatttgtttattgctgt
ccagtgatgtaccatgttcgttgagtgtcggattatactaattattgttgattgataatcttgtagtttgct
tttcctaatttatttatcgtagtcctgatttgcctcagctgtgcctcacccgtgcgatggtcaatcaacttg
ttagcccaatctgcttaatcatgtacatttgttgttagaatcagagatcaagccaattagctatcttattgc
ttatctgttccatgttctgatcgatgtaacagtctacacttttgctctgtgctacttgattaaaacattctg
acttaaattcatgattggaagtttcagatctgattgttgccttacttgactaatatctattcatgtgacacc
tctctgtcttggtaacttaccgctgtttgtttgtaatttctgactatgcagATGcagatctttgtgaagacc
ctcactggcaaaaccatcacccttgaggtcgagtcgtccgacacgatcgacaacgtcaaggcaaagatccag
gacaaggagggcattcctccagaccagcagcgcctcatctttgctggaaagcagcttgaggacggccgcacc
ctcgccgactacaacatccagaaggagtccaccctccacctggtcctgaggctccgtggtggcatgcagatc
ttcgtcaagaccccttaccggcaagaccatcacgctggaggtcgagtcctctgacacgatcgacaatgtgaag
gcgaagatccaggataaggagggcatcccccggaccagcagcgcctcatctttgccggcaagcagcttgag
gacggccgtaccctcgccgactacaacatccagaaggaatccacactccatctggtgctcaggctgcgtggt
ggcatgcagatcttcgtcaagaccctaaccggcaagaccatcactctggaggttgagtcctctgacacgatc
gacaatgtgaaggcaaagatccaggataaggagggcattcccccggaccagcagcgcctcatcttcgctggc
aagcagcttgaggatggccgcaccctggcagattacaatatccagaaggaatccaccttgcacctggtgctt
cgcctccgtggtggcatgcagatctttgtaaagaccttgactggcaagacaattaccctggaggttgagtcg
tccgacacaattgacaatgtcaaggcgaagatccaggacaaggagggcatccaccggaccagcagcgcctc
atcttcgccggcaagcagcttgaggatggtcgcacccttgcagattacaatatccagaaggaatccactctg
catctggtgcttcgtctccgcggtggaatgcagatcttcgttaagacgttgacagggaagaccatcacactg
gagggttgaatcttcggacaccattgacaacgtgaaggcaaagatccaggacaaggagggcatccccccagac
cagcagcgcctcatctttgctggtaagcagcttgaggatggccgcaccttgcagattacaacattcagaag
gagtccaccctgcacctggtgctccgtctccgtggtgggcagTAAgcttctgccgaactggttcacagtctg
ctgcccttggtggtctgccccttagtggtcatgccttttgttatgtgtcttgcgtcccaatcctgtatcgtt
tgtgtgaacatctctgctgctgtatagcagcttgaatcctgttatgaatttgtgaacctgaaccttgttccg
tgaatcatgttatgaataagtgaacctgaaccttgttccgtgattattgttacaatctgttgtgccgtatgg

Fig. 36 cont.

```
ttggtcgtgtgtgatttatgttgaactggagaaccaagttcgttccaggacatattgcaacctaagctaaac
catgtagaactacttgttctgggagacataaaacgtcattttatgcattcgtaacatttaagcatactaca
ataattgtattgtccttttcctactcatccttgaaaccatatgcctcttctcagcgcctctacatgcagtgt
gctcagaacaaacaggccctgccagctgcttttcaattttccaattaataaccacaatagtcggactatggc
atctgtgggtgactatgcaagatgttgctgtcaggtctctgaaacttttcccatgtatctgttgaaattacc
cagtaaattcatgcctctatttaatctggcatggttgattttcaaacagaatgtgttttttttgttctgga
agctatattggtaaataaatacaaagctggagtgtgattatatttccaacagatattcaagaaaatctcagt
tgatttatttactactgtagtatatatatatatcttacagttgacttctcatatttcaaacgacatgtgagc
acattgttcagtttcttaggatgtgttgtgtgctcaaaggtgtaattttgcattctgccctccgagtaaaca
ctacacgtatttttttgagtggcagtgcatttgattacaaggcaacaacaacaaaaacctatggcaagatat
ccttcttagaggctgccaggatcattttgactgaactatgtaaggctgaagaaaagg (SEQ ID NO:20)
```

Fig. 37 tgcgtctggacgcacaagtcatagcattatcggctaaaatttcttaatttctaaattagtcatatcggctaa
gaaagtggggagcactatcatttcgtagaacaagaacaaggtatcatatatatatatatatataatatttaa
actttgttaagtggaatcaaagtgctagtattaatggagtttcatgtgcattaaattttatgtcacatcagc
aatttgttgacttggcaaggtcatttagggtgtgtttggaagacaggggctattaggagtattaaacatag
tctaattacaaaactaattgcacaaccgctaagctgaatcgcgagatggatctattaagcttaattagtcca
tgatttgacaatgtggtgctacaataaccatttgctaatgatggattacttaggtttaatagattcgtctcg
tgatttagcctatgggttctgctattaattttgtaattagctcatatttagttcttataattagtatccgaa
catccaatgtgacatgctaaagtttaaccctggtatccaaatgaagtcttatgagagtttcatcactccggt
ggtatatgtacttaggctccgttttcttccaccgacttattttttagcacccgtcacattgaatgtttagata
ctaattagaagtattaaacgtagactatttacaaaatccattacataagacgaatctaaacggcgagacgaa
tctattaaacctaattagtccatgatttgacaatgtgttgctacagtaaacatttgctaatgatggattaat
taggcttaatagattcgtctcgccgtttagcctccacttatgtaatgggttttctaaacaatctacgtttaa
tactcctaattagtatctaaatattcaatgtgacacgtgctaaaaataagtcagtggaaggaagagaacgtc
cccttagttttccatcttattaattgtacgatgaaactgtgcagccagatgattgacaatcgcaatacttca
actagtgggccatgcacatcagcgacgtgtaacgtcgtgagttgctgttcccgtagAGAAATATCAACTGGT
GGGCCACGCACATCAGCGTCGTGTAACGTGGACGGAGGAGCCCCGTGACGGCGTCGACATCGAACGGCCACC
AACCACGGAACCACCCGTCCCCACCTCTCGGAAGCTCCGCTCCACGGCGTCGACATCTAACGGCTACCAGCA
GGCGTACGGGTTGGAGTGGACTCCTTGCCTCTTTGCGCTGGCGGCTTCCGGAAATTGCGTGGCGGAGACGAG
GCGGGCTCGTCTCACACGGCACGGAAGACgtcacgggttccttccccacctctcctcttccccaccgccata
aatagCCGACCCCCTCGCCTTTCTCCCCAATCTCATCTCGTCTCGTGTTGTTCGGAGCACACCACCCGCCCC
AAATCGTTCTTCCCGCAAGCCTCGGCGATCCTTCACCCGCTTCAAGgtacggcgatcgtcttcctcctctag
atcggcgtgatctgcaagtagttgatttggtagatggttaggatctgtgcactgaagaaatcatgttagatc
cgcgatgtttctgttcgtagatggctgggaggtggaattttgtgtagatctgatatgttctcctgtttatc
ttgtcacgctcctgcgatttgtggggatttttaggtcgttgatctgggaatcgtggggttgcttctaggctgt
tcgtagatgaggtcgttctcacggttactggatcattgcctagtagatcagctcgggctttcgtctttgta
tatggtgcccatacttgcatctatgatctggttccgtggtgttacctaggtttctgcgcctgattcgtccga
tcgattttgttagcatgtggtaaacgtttggtcatggtctgatttagattagagtcgaataggatgatctcg
atctagctcttgggattaatatgcatgtgtcaccaatctgttccgtggttaagatgatgaatctatgcttag
ttaatgggtgtagatatatatgctgctgttcctcaatgatgccgtagcttttacctgagcagcatggatcct
cctgttacttaggtagatgcacatgcttatagatcaagatatgtactgctactgttggaattctttagtata
cctgatgatcatccatgctcttgttacttgttttggtatacttggatgatggcatgctgctgcttttgttg
atttgagcccatccatatctgcatatgtcacatgattaagatgattacgctgtttctgtatgatgccatagc
ttttatgtgagcaacatgcatcctcctggttatatgcattaatagatggaagatatctattgctacaatttg
atgattattttgtacatacgatgatcaagcatgctcttcatactttgttgatatacttggataatgaaatgc
tgctgcacgttcattctatagcactaatgatgtgatgaacacgcacgacctgtttgtggcatctgtttgaat
gtgttgttgctgttcactagagactgttttattaacctactgctagatacttacccttctgtctgtttattc
ttttgcagATGcagatctttgtcaagaccctcaccggcaagaccatcaccctcgaggtggagtcttctgaca
ccattgacaacgtcaaggccaagatccaggacaaggaaggcattccccggatcagcagcggctcatctttg
ccggcaagcagcttgaggatgggcgcaccctggctgactacaacatccagaaggagagcaccctccacctgg
tgctccgtctcaggggaggcatgcagatctttgtgaagaccttgactggcaagaccatcacccttgaggtgg

Fig. 37 cont.

agtcttccgacaccatcgacaacgtcaaggccaagatccaggacaaggagggcatcccccggaccagcaga
ggctcatctttgcgggcaagcagcttgaggatggacgcaccctggctgactataacatccagaaggagagca
ccctccatctggtgctccgtctcaggggaggcatgcagatcttcgtgaagactctcactggcaagaccatca
ccctcgaggtggagtcttccgacaccatcgacaacgtcaaggccaagatccaggacaaggagggcatccccc
cagaccagcagaggctcatctttgctggcaagcagcttgaggacggacgcaccctggctgactataacatcc
agaaggagagcaccctccacctggtgctccgcctgagggtgggatgcagatctttgtgaagactttgactg
gcaagaccattactttggaggttgagagctccgacaccatcgacaacgtgaaggccaagatccaggacaagg
aaggcatcccccggaccagcagaggctcatcttcgccggcaagcagcttgaggacggacgcaccctggctg
actataacatccagaaggagagcaccctccacctggtgctccgtctcaggggaggcatgcagatcttcgtga
agaccctcactggcaagaccatcacccttgaggtggagtcttccgacaccatcgacaatgtcaaggccaaga
tccaggacaaggagggcatcccccagaccagcagagactcatctttgcaggcaagcagcttgaggacggac
gcaccctggctgactacaacatccagaaggagagcacctccacctggtgctccgtctcaggggaggcatgc
agatcttcgtgaagaccctcactggcaagaccatcaccctcgaggtggagtcttctgacaccatcgacaacg
tcaaggccaagatccaggacaaggagggcatcccccggaccagcagcgtcttatctttgccggcaagcagc
tggaggatggccgcaccttgcggattacaatatccagaaggagagcacctccatctggtgctccgtctga
ggggtgggatgcagatattcgtgaagactttgaccggcaagaccatcacttggaggttgagagctccgaca
ccattgacaatgtgaaggccaagatccaggacaaggagggtatcccccggaccagcagcgtctgatcttcg
ccggcaagcaactggaggatggccgcaccctggcggactacaatatccagaaggagtccaccctccacctgg
tgctccgcctccgtggtggtcagTAAgcccatcggtcatggatgcttctactgtacctgggtcgtctggtct
ctgcctgtgtcacctttgaagtacctgtgtcgggattgtgtttggtcatgaactgcagtttgtcttgatgt
tctttgtctggtcttatgaactggttgtatctgtatgtttactgtaaactgttgttgcggtgcagcagtat
ggcatccgaatgaataaatgatgtttggacttaaatctgtactctgtttgttttcggttatgccagttctat
attgcctgagatcagaatgtttagcttttgagttctgtttggcttgtggtcgactcctgtttcttacttgag
gcgtaactctgttctggcaaactcaaatgtctaactgaatgttttaggacttaattgttggacagattaacg
tgtttggtttgtttctagattgtgattcggaaggcttgttagttgtggaatcaaggagagcagctaggtctg
tgcagaacgttattttggatttaagccttctcagattatgccattactctaaacctaatgatatcatatttc
actcggggatgttggagtagtcttttctttctcctgcagacaaaatgattttgctttcgtgtgtgtacatga
ttttgtgcaactgttgcaacaactgaagtagacaagttttgacctcaccagaagaatgaaaaagatttgga
atttgttacatcgacaaaccattgtaacttggcccatcagaatgcacagaagagcggctacaaattgacatg
cgttgcaaactttgcaatagttgatgcacatgtttgccattgcctgccagtcttaggaaaagtgtgtggttc
gagaaatctaagcatatgtgctctgctcacattgcgtggaacccacacagctttgtcacactcttgtccact
ccagaagtcattcctggcgctgtttaccctggtaaaaggtaaccgaaaacttctcaaggctgtacccaaaa
ctggaaggaaatttggaggaaatctttgcttttgatcggctcactctttc (SEQ ID NO:21)

Fig. 38 ttgaattttaattttcaaattttgcagggtagtagtggacatcacaatacatatttagaaaaagttttataat
tttcctccgttagttttcatataattttgaactccaacgattaatctattattaaatatcccgatctatcaa
aataatgataaaaatttatgattaattttttctaacatgtgttatggtgtgtactatcgtcttataaaatttc
aacttaaaactccacctatacatggagaaatgaaaaagacgaattacagtagggagtaatttgaaccaaatg
gaatagtttgagggtaaaatgaactaaacaatagtttaggaggttattcagattttagttatagttgagagg
agtaatttagacttttttcctatcttgaattgttgacggctctcctatcggatatcggatggagtctttcagc
ccaacataacttcattcgggcccaaacgttcgtccatccagcctagggagaacattttgcccatgatatctg
ttttctttttttctattttcactggtattataggagggaaatatacaacgtgttcacctttggtttcattc
ttgttccatctgaatttatctaaaactgtgtttgaacttcgtaagaattttgttcgatctgtccggtacatc
gtgttgataggtggcctccgagattcttcttttttaaccggcaaagtaaaataatctcagctccagcctaacg
tcaattatcagagagagaaaaaaatattttttttatgattgatcggaaaccaaccgccttacgtgtcgatcct
ggttcctggccggcacggcggaggaaagcgaccgacctcgcaacgccggcgcacggcgccgccgtgttggac
ttggtctcccgcgactccgtgggcctcggcttatcgcgccgctccatctcaaccgtccgcttggacacgtg
gaagttgatccgtcgcgcaccagcctcggaggtaacctaactgcccgtactataaatccgggatccggcctc
tccaatccccatcgccaCAAGTTCGCGATCTCTCGATTTCACAAATCGCCGAGAAGACCCGAGCAGAGAAGT
TCCCTCCGATCGCCTTGCCAAGgtactcctacctaatcctccttaactgatctctcctctatcacgttggta
atcttcgaatgatctgctgcctggctcgctgttcccctcgttatgcactgtttccatcacgagttttttt
ttcatcatctaatctatgcggttgcggaagaattgtggctagtggagtagttttctgtgcttgatcggtaga
ttcgatgtgtgggtgtatggatgttttctgaaaagttgctggattagtttacgctttcaggccgcaggtctg
ttcgaaattgattatgaagtctatatgctttggatctatcgatttccagtttattcagatgtaggccaaaa
aattgtcggcatttgtgtggaattagttggcctttaggtctgcacattcatggtgacggcacagttgctgct
ggctgttgcgtgggacgagttattatagttgttttgttttccctgattgattcacattttcaatgataac
tagcctttgtcacctaaccaagtccaggttgatcctatctgtgttcttcagctaccagtttgcatagatgat
ggtgtattcgattgctttagtaggccttctgatttcacatctaattctgtcatgaatatagataactttaca
tgcttttgatatactttatatttgaactgttcactgtccagcctattttggataattgagtgcattggcttt
tgatgcctgaattattcacatgttcctggataattgacctgtgtcacctagttgactgttttttgaggtgcc
acccgtctgttcagctgatttgtgtattcgattgctctagttaatcttttgattatgcagctagtgctttgt
catatgtagctttataggcttctgatgtccttggatatagttcagtctacttgtcaagttgctttacaagta
gtagctctgattctatttggcttcctgagtcagagctttgcaaattgcttgttgttacattacatcatatta
cttgaattgcagttatttaatggttggattgttgctgtttacttctacattttttgctgttttatattatac
taaaatgtttgtgttgctgcttttcagATGcagatctttgtgaagacactcactggcaagactatcacccctt
gaggtggagtcttctgacacaattgacaatgtcaaggcaaagatccaggacaaggaagggattcctccagac
cagcagcgccttatcttcgctggcaagcagcttgaggatggccgtacacttgcagattacaacattcagaag
gagtccacactgcaccttgtcctcaggctgcgtggaggcatgcagattttcgtgaagaccctcactggcaag
acgatcacctagaggtggagtcatctgacaccatcgacaatgtgaaggcaaagatccaggacaaggagggc
atcccccctgaccagcagcgcctcatctttgcaggcaagcagttggaggatgggcgaactctggctgactat
aatatccagaaagagtccacccttcacctcgtcctccgcctgcgaggtggcatgcagatctttgtgaagacg
ctgacaggcaagaccatcacattggaagttgagtcctccgatacaatcgacaatgtgaaggccaagatccag
gataaggagggtatccccccggaccagcagcgcctcatcttcgccggcaagcagctcgaggatggccgcact
ctcgctgactacaacatccagaaggaatcaaccctgcacctggtgctccgcctgcgtggtggaatgcagatc

Fig. 38 cont.

tttgtgaagacgcttaccggcaagaccatcaccttggaggtggagtcttcggacaccatcgacaatgtgaag
gcgaagattcaggacaaggagggcattcctccggaccagcagcgcctcatctttgctggcaagcagctagag
gacgggcgtaccctggcggattacaacatccagaaggagtccaccctccaccttgtcctgcgcctccgtggt
ggtttcTGAgcctagtgctcctgagttgccttttgtcgttatggtcaacctctggtttaagtcgtgtgaact
ctctgcattgcgttgctagtgtctggttgtggttgtaataagaacatgaagaacatgttgctgtggatcaca
tgactttttttttgaaccggaagatcacatgactttcatggctttaagttcctgaactctgaaatctggac
ccctttttaagctctgaactcatcattcttgcatttacatctggtgttgatcttattgatgtgatgcagtcc
tgctgaaatagtcaatgtagattcatgactgactgattgcgtttatggtgtgtatgttgttaacaagctgaa
ggtcgtgtggtgtctttccagttagacgaagtgtgctttattgtagcgtgtagtgctgctggatgattgatg
aactgaaacattctgcatttagcaactagcgagccaaaggtgatgactgagtttctgtagacctgtttttt
atgcccatggtcgttcttcaattgcacttgattttcacattagctggatcataatctgagcagactactcaa
aagtacaaagttcatcttcgctatgacgctttgccactaggattttctttgtatgatttgtttacaaatcct
gtaatctagtcaaaagaaaagccaaaattttctttgtatgatttgtttacaaatcctctaatctagtcaaa
gaaaagccaaatttatccctcctggtccctacatcacgtagctatgtggcccgcaagcagatgaaagcagc
cccgtcagccgacgccgacgccgacgccaacacatcctgctcctccctcgccggcgccggcgccggcgaggc
cgcaccgccgctgccccgtggccgcaggcacacggtgccgcactgccgccgcccgtggccgcaggcacacg
gtgccgcactgccgccgcctcccctccggcattgccggacggctgggctactgtcccgccgccttcccaa
t (SEQ ID NO:34)

```
                        SEQUENCE LISTING

<160> NUMBER OF SEQ ID NOS: 40

<210> SEQ ID NO 1
<211> LENGTH: 1029
<212> TYPE: DNA
<213> ORGANISM: Brachypodium distachyon

<400> SEQUENCE: 1
ctgctcgttc agcccacagt aacacgccgt gcgacatgca gatgccctcc accacgccga      60 ccaacccccaa gtccgccgcg ctcgtccacg gcgccatccg catccgcgcg tcaacgtcat     120
ccggaggagg cgagcgcgat gtcgacggcc acggcggcgg cggacacgac ggcgacgccc     180
cgactccgcg cgcgcgtcaa ggctgcagtg gcgtcgtggt ggccgtccgc ctgcacgaga     240
tccccgcgtg gacgagcgcc gcctccaccc agcccctata tcgagaaatc aacggtgggc     300
tcgagctcct cagcaacctc cccaccccccc cttccgacca cgctcccttc ccccgtgccc     360
ctcttctccg taaacccgag ccgccgagaa caacaccaac gaaagggcga agagaatcgc     420
catagagagg agatgggcgg aggcggatag tttcagccat tcacggagaa atggggagga     480
gagaacacga catcatacgg acgcgaccct ctagctggct ggctgtccta aagaatcgaa     540
cggaatcgct gcgccaggag aaaacgaacg gtcctgaagc atgtgcgccc ggttcttcca     600
aaacacttat ctttaagatt gaagtagtat atatgactga aattttaca aggtttttcc      660 ccataaaaca ggtgagctta tctcatcctt ttgtttagga tgtacgtatt atatatgact     720 gaatatttt tattttcatt gaatgaagat tttcgacccc ccaaaaataa aaacggagg      780 gagtaccttt gtgccgtgta tatggactag agccatcggg acgtttccgg agactgcgtg     840 gtggggggcga tggacgcaca acgaccgcat tttcggttgc cgactcgccg ttcgcatctg     900
gtaggcacga ctcgtcgggt tcggctcttg cgtgagccgt gacgtaacag acccgttctc     960
```

```
ttccccgtc tggccatcca taaatccccc ctccatcggc ttcccttcc tcaatccagc   1020 accctgatt                                                         1029

<210> SEQ ID NO 2
<211> LENGTH: 636
<212> TYPE: DNA
<213> ORGANISM: Brachypodium distachyon

<400> SEQUENCE: 2
ggcgtcagga ctggcgaagt ctggactctg cagggccgaa ctgctgaaga cgaagcagag    60
gaagagaaag ggaagtgttc gacttgtaat ttgtaggggt ttttttaga ggaacttgta   120 atttgtaggt gggctggcct cgttggaaaa acgatgctgg ctggttgggc tgggccgatg   180
tacgcttgca acaacttgt ggcggcccgt tctggacgag caggagtttc ttttttgttc   240 tcactttct ggtcttcttt agttacggag tacctttgt tttttaaagg agttaccttt    300
tttttaggaa ttctttagtt acctttcgct tgctctcaaa aaatatttaa ctttcgcttt   360
ttttcatttt aatttttgca actatttacg agtttcatga atgcttattt ccagcatat   420 cattatttgc aagtattttt atgccgtatg tattggacga gagccatcgg gactgttcca   480
gagactgcgt ggtggggacg gctcccaacc gccttttcta tctctgttcg catccggtgg   540
ccgacttggc tcgcgcgtga gccgtgacgt aacagacttg gtctcttccc catctggcca   600
tctataaatt ccccatcga tcgaccctcc ctttcc                            636

<210> SEQ ID NO 3
<211> LENGTH: 1064
<212> TYPE: DNA
<213> ORGANISM: Setaria italica

<400> SEQUENCE: 3
tgcgtctgga cgcacaagtc atagcattat cggctaaaat ttcttaattt ctaaattagt    60
catatcggct aagaaagtgg ggagcactat catttcgtag aacaagaaca aggtatcata   120
tatatatata tatataatat ttaaactttg ttaagtggaa tcaaagtgct agtattaatg   180
gagtttcatg tgcattaaat tttatgtcac atcagcaatt ttgttgactt ggcaaggtca   240
tttagggtgt gtttggaaga caggggctat taggagtatt aaacatagtc taattacaaa   300
actaattgca caaccgctaa gctgaatcgc gagatggatc tattaagctt aattagtcca   360
tgatttgaca atgtggtgct acaataacca tttgctaatg atggattact taggtttaat   420
agattcgtct cgtgatttag cctatgggtt ctgctattaa ttttgtaatt agctcatatt   480
tagttcttat aattagtatc cgaacatcca atgtgacatg ctaaagttta accctggtat   540
ccaaatgaag tcttatgaga gtttcatcac tccggtggta tatgtactta ggctccgttt   600
tcttccaccg acttatttt agcacccgtc acattgaatg tttagatact aattagaagt    660
attaaacgta gactatttac aaaatccatt acataagacg aatctaaacg gcagacgaa    720 tctattaaac ctaattagtc catgatttga caatgtgttg ctacagtaaa catttgctaa   780
tgatggatta attaggctta atagattcgt ctcgccgttt agcctccact tatgtaatgg   840
gttttctaaa caatctacgt ttaatactcc taattagtat ctaaatattc aatgtgacac   900
gtgctaaaaa taagtcagtg gaaggaagag aacgtcccct tagttttcca tcttattaat   960
tgtacgatga aactgtgcag ccagatgatt gacaatcgca atacttcaac tagtgggcca  1020
tgcacatcag cgacgtgtaa cgtcgtgagt tgctgttccc gtag                  1064
```

<210> SEQ ID NO 4
<211> LENGTH: 1026
<212> TYPE: DNA
<213> ORGANISM: Brachypodium distachyon

<400> SEQUENCE: 4

```
gtttgtcaaa aactggccta cagtctgctg ccccctgttgg tctgcccctt ggaagtagtc      60
gtgtctatgg ttatgtgaga agtcgttgtg ttctttctaa tcccgtactg tttgtgtgaa     120
catctgctgc tgtcgtattg catcgtgaag aatcctgtta tgaataagtg aacatgaacc     180
ttgttctgtg attacggctt cgtggttatg cgaacgttct tacaaacgca attgcacctg     240
atgtaaaatc gttttgtgcta gctgtatgga acaagtgctc atgatgttca tgcaagatgc     300
aattccagct tttgttggtt tgtcatcttt gtactgtgct taccgcacat aaagattgca     360
tcttgcttat tgctttgttg ctttggtgct cgtccgcttc tccttgcacc ttatcaaacc     420
tttgttagta ttctcttctt atagcacttg gtaactctca gctttacaac gccagtactg     480
tttctgaaat tcatgactg ataaagctga tagatggagt actaatatat gacatctttc     540
cataaatgtt cgggtgcaga gatatggagg ccccaggatc ctatttacag gatgaaccta     600
cctgggccgc tgtacgcatg acatccgcga gcaagtctga ggttctcaat gtacacatga     660
aattgatttt tgctgcgttt ggcttggctg atcgttgcat ttgttctgat tcatcagagt     720
taaataacgg atatatcagc aaatatccgc agcatccaca ccgaccacac gtccggttaa     780
cagagtcccc ctgccttgct ttaattatta cggagtactc cgctattaat ccttagatat     840
gtttcgaagg aactcaaacc ttcctccatc tgcaaatctc agtgcttcaa aactggaatt     900
agataattga aaccttcatt cggttgcaat tcacaactgc aaattgaaca gcactgtcaa     960
tttcaatttc gggttcacga ttccaccgat aggttgacat gatccatgat ccacccattg    1020
tacaac                                                                1026
```

<210> SEQ ID NO 5
<211> LENGTH: 1020
<212> TYPE: DNA
<213> ORGANISM: Brachypodium distachyon

<400> SEQUENCE: 5

```
gcttctgccg aactggttca cagtctgctg cccttggtgg tctgcccctt agtggtcatg      60
ccttttgtta tgtgtcttgc gtcccaatcc tgtatcgttt gtgtgaacat ctctgctgct     120
gtatagcagc ttgaatcctg ttatgaattt gtgaacctga accttgttcc gtgaatcatg     180
ttatgaataa gtgaacctga accttgttcc gtgattattg ttacaatctg ttgtgccgta     240
tggttggtcg tgtgtgattt atgttgaact ggagaaccaa gttcgttcca ggacatattg     300
caacctaagc taaaccatgt agaactactt gttctgggag acataaaacg tcattttat     360
gcattcgtaa catttaagca tactacaata attgtattgt ccttttccta ctcatccttg     420
aaaccatatg cctcttctca gcgcctctac atgcagtgtg ctcagaacaa acaggccctg     480
ccagctgctt ttcaattttc caattaataa ccacaatagt cggactatgg catctgtggg     540
tgactatgca agatgttgct gtcaggtctc tgaaactttt cccatgtatc tgttgaaatt     600
acccagtaaa ttcatgcctc tatttaatct ggcatggtt attttcaaac agaatgtgtt     660
ttttttttgtt ctggaagcta tattggtaaa taaatacaaa gctggagtgt gattatattt     720
ccaacagata ttcaagaaaa tctcagttga tttatttact actgtagtat atatatatat     780
cttacagttg acttctcata tttcaaacga catgtgagca cattgttcag tttcttagga     840
```

```
tgtgttgtgt gctcaaaggt gtaattttgc attctgccct ccgagtaaac actacacgta    900 ttttttttgag tggcagtgca tttgattaca aggcaacaac aacaaaaacc tatggcaaga    960
tatccttctt agaggctgcc aggatcattt tgactgaact atgtaaggct gaagaaaagg   1020
```

<210> SEQ ID NO 6
<211> LENGTH: 1032
<212> TYPE: DNA
<213> ORGANISM: Setaria italica

<400> SEQUENCE: 6

```
gcccatcggt catggatgct tctactgtac ctgggtcgtc tggtctctgc ctgtgtcacc     60
tttgaagtac ctgtgtcggg attgtgtttg gtcatgaact gcagtttgtc tttgatgttc    120
ttttgtctgg tcttatgaac tggttgtatc tgtatgttta ctgtaaactg ttgttgcggt    180
gcagcagtat ggcatccgaa tgaataaatg atgtttggac ttaaatctgt actctgtttg    240
ttttcggtta tgccagttct atattgcctg agatcagaat gtttagcttt tgagttctgt    300
ttggcttgtg gtcgactcct gtttcttact tgaggcgtaa ctctgttctg gcaaactcaa    360
atgtctaact gaatgtttta ggacttaatt gttggacaga ttaacgtgtt tggtttgttt    420
ctagattgtg attcggaagg cttgttagtt gtggaatcaa ggagagcagc taggtctgtg    480
cagaacgtta ttttggattt aagccttctc agattatgcc attactctaa acctaatgat    540
atcatatttc actcggggat gttggagtag tcttttcttt ctcctgcaga caaatgatt    600 ttgctttcgt gtgtgtacat gattttgtgc aactgttgca acaactgaag tagacaagtt    660
ttgacctcac cagaagaatg aaaaagattt tggaatttgt tacatcgaca aaccattgta    720
acttggccca tcagaatgca cagaagagcg gctacaaatt gacatgcgtt gcaaactttg    780
caatagttga tgcacatgtt tgccattgcc tgccagtctt aggaaaagtg tgtggttcga    840
gaaatctaag catatgtgct ctgctcacat gcgtggaaac ccacacagct ttgtcacact    900
cttgtccact ccagaagtca ttcctggcgc tgtttacccc tggtaaaagg taaccgaaaa    960
cttctcaagg ctgtacccaa aactggaagg aaatttggag gaaatctttg cttttgatcg   1020
gctcactctt tc                                                       1032
```

<210> SEQ ID NO 7
<211> LENGTH: 993
<212> TYPE: DNA
<213> ORGANISM: Brachypodium distachyon

<400> SEQUENCE: 7

```
gtatgcagcc tcgcttcctc ctcgctaccg tttcaattct ggagtaggtc gtagaggata     60
ccatgttgat ttgacagagg gagtagatta gatacttgta gatcgaagtg cggatgttcc    120
atggtagatg ataccatgtt gatttcgatt agatcggatt aaatctttgt agatcgaagt    180
gcgcatgttc catgaattgc ctgttaccag tagattcaag ttttttctgtg ttatagaggt    240 gggatctact cgttgagatg attagctcct agaggacacc atgccgtttt ggaaaataga    300
tcagaaccgt gtagatcgat gtgagcatgt gttcctgtag atccaagttc tttcgcatgt    360
tactagttgt gatctattgt ttgtgtaata cgctctcgat ctatccgtgt agatttcact    420
cgattactgt tactgtggct tgatcgttca tagttgttcg ttaggtttga tcgaacagtg    480
tctgaaccta attggatatg tattcttgat ctatcaacgt gtaggtttca gtcatgtatt    540
tatgtactcc ctccgtccca aattaactga cgtggatttt gtataagaat ctatacaaat    600
ccatgtcagt taattcggga tggagtacca tattcaataa tttgtttatt gctgtccact    660
```

```
tatgtaccat atgtttgttg ttcctcatgt ggattctact aattatcatt gattggtgat      720
cttctatttt gctagtttcc tagctcaatc tggttattca tgtagatgtg ttgttgaaat      780
cggagaccat gcttgttatt agatagttta ttgcttatca gtttcatgtt ctggttgatg      840
caacacatat tcatgttcgc tatctggttg ctgcttgata ttctctgatt tacattcatt      900
ataagaatat attctgctct ggttgttgct tctcatgact ttacctactc ggtaggtgac      960 ttacctttg gtttacaatt gtcaactatg cag                                    993
```

<210> SEQ ID NO 8
<211> LENGTH: 852
<212> TYPE: DNA
<213> ORGANISM: Brachypodium distachyon

<400> SEQUENCE: 8

```
gtatgtagcc tctcgattcc tcctcagccc tgccctcgat ttggtgtacg cgttgagatg       60
atgatctcgt agatgtctag atgacaccat gtcgatttga aatagatcag atccgtgtag      120
atcgatgagc tcctgtgtac ctgtggattc aagttatttt cgcatgctat tgttgtgatc      180
tactagatct agtgtgtgta ttctatgcta tcgatttctc cgtgtagatt tcactcgatt      240
actgttactg tggcttgatc ggccatagat gttggttaag gtttgatcgg ttagtgtttg      300
aacctgcgtg gatatctagc atccatctat tatcgtgtag gttcgaaca aacaagcact       360 attattgtac tgatggttcg tctatggttg gttttgaccg ttttagtgtt gaacgagcct      420
tctgtatttg tttattgctg tccagtgatg taccatgttc gttgagtgtc ggattatact      480
aattattgtt gattgataat cttgtagttt gcttttccta atttatttat cgtagtcctg      540
atttgcctca gctgtgcctc acccgtgcga tggtcaatca acttgttagc ccaatctgct      600
taatcatgta catttgttgt tagaatcaga gatcaagcca attagctatc ttattgctta      660
tctgttccat gttctgatcg atgtaacagt ctacactttt gctctgtgct acttgattaa      720
aacattctga cttaaattca tgattggaag tttcagatct gattgttgcc ttacttgact      780
aatatctatt catgtgacac ctctctgtct tggtaactta ccgctgtttg tttgtaattt      840
ctgactatgc ag                                                          852
```

<210> SEQ ID NO 9
<211> LENGTH: 48
<212> TYPE: DNA
<213> ORGANISM: Setaria italica

<400> SEQUENCE: 9

```
gtcacgggtt ccttccccac ctctcctctt ccccaccgcc ataaatag                    48
```

<210> SEQ ID NO 10
<211> LENGTH: 1114
<212> TYPE: DNA
<213> ORGANISM: Setaria italica

<400> SEQUENCE: 10

```
gtacggcgat cgtcttcctc ctctagatcg gcgtgatctg caagtagttg atttggtaga       60
tggttaggat ctgtgcactg aagaaatcat gttagatccg cgatgtttct gttcgtagat      120
ggctgggagg tggaattttt gtgtagatct gatatgttct cctgtttatc ttgtcacgct      180
cctgcgattt gtggggattt taggtcgttg atctggaat cgtggggttg cttctaggct       240
gttcgtagat gaggtcgttc tcacggttta ctggatcatt gcctagtaga tcagctcggg      300
```

```
ctttcgtctt tgtatatggt gcccatactt gcatctatga tctggttccg tggtgttacc      360
taggtttctg cgcctgattc gtccgatcga ttttgttagc atgtggtaaa cgtttggtca      420
tggtctgatt tagattagag tcgaatagga tgatctcgat ctagctcttg ggattaatat      480
gcatgtgtca ccaatctgtt ccgtggttaa gatgatgaat ctatgcttag ttaatgggtg      540
tagatatata tgctgctgtt cctcaatgat gccgtagctt ttacctgagc agcatggatc      600
ctcctgttac ttaggtagat gcacatgctt atagatcaag atatgtactg ctactgttgg      660
aattctttag tatacctgat gatcatccat gctcttgtta cttgttttgg tatacttgga      720
tgatggcatg ctgctgcttt tgttgatttt gagcccatcc atatctgcat atgtcacatg      780
attaagatga ttacgctgtt tctgtatgat gccatagctt ttatgtgagc aacatgcatc      840
ctcctggtta tatgcattaa tagatggaag atatctattg ctacaatttg atgattattt      900
tgtacatacg atgatcaagc atgctcttca tactttgttg atatacttgg ataatgaaat      960
gctgctgcac gttcattcta tagcactaat gatgtgatga acacgcacga cctgtttgtg     1020
gcatctgttt gaatgtgttg ttgctgttca ctagagactg ttttattaac ctactgctag     1080
atacttaccc ttctgtctgt ttattctttt gcag                                 1114

<210> SEQ ID NO 11
<211> LENGTH: 55
<212> TYPE: DNA
<213> ORGANISM: Brachypodium distachyon

<400> SEQUENCE: 11
ccgatcgaaa agtccccgca agagcaagcg accgatctcg tgaatctccg tcaag           55

<210> SEQ ID NO 12
<211> LENGTH: 75
<212> TYPE: DNA
<213> ORGANISM: Brachypodium distachyon

<400> SEQUENCE: 12
ccaatccagc accccgatc cgatcgaaa attctccgca acagcaagcg atcgatctag        60
cgaatccccg tcaag                                                       75

<210> SEQ ID NO 13
<211> LENGTH: 261
<212> TYPE: DNA
<213> ORGANISM: Setaria italica

<400> SEQUENCE: 13
agaaatatca actggtgggc cacgcacatc agcgtcgtgt aacgtggacg gaggagcccc      60
gtgacggcgt cgacatcgaa cggccaccaa ccacggaacc accgtccc accctctcgga     120 agctccgctc cacggcgtcg acatctaacg gctaccagca ggcgtacggg ttggagtgga     180
ctccttgcct ctttgcgctg gcggcttccg gaaattgcgt ggcggagacg aggcgggctc     240
gtctcacacg gcacggaaga c                                              261

<210> SEQ ID NO 14
<211> LENGTH: 113
<212> TYPE: DNA
<213> ORGANISM: Setaria italica

<400> SEQUENCE: 14
ccgaccccct cgcctttctc cccaatctca tctcgtctcg tgttgttcgg agcacaccac      60
ccgccccaaa tcgttcttcc cgcaagcctc ggcgatcctt cacccgcttc aag            113
```

<210> SEQ ID NO 15
<211> LENGTH: 2077
<212> TYPE: DNA
<213> ORGANISM: Brachypodium distachyon

<400> SEQUENCE: 15

```
ctgctcgttc agcccacagt aacacgccgt gcgacatgca gatgccctcc accacgccga      60
ccaaccccaa gtccgccgcg ctcgtccacg gcgccatccg catccgcgcg tcaacgtcat     120
ccggaggagg cgagcgcgat gtcgacggcc acggcggcgg cggacacgac ggcgacgccc     180
cgactccgcg cgcgcgtcaa ggctgcagtg gcgtcgtggt ggccgtccgc ctgcacgaga     240
tccccgcgtg gacgagcgcc gcctccaccc agcccctata tcgagaaatc aacggtgggc     300
tcgagctcct cagcaacctc cccaccccc cttccgacca cgctcccttc cccgtgccc      360
ctcttctccg taaacccgag ccgccgagaa caacaccaac gaaagggcga agagaatcgc     420
catagagagg agatgggcgg aggcggatag tttcagccat tcacggagaa atggggagga     480
gagaacacga catcatacgg acgcgaccct ctagctggct ggctgtccta agaatcgaa      540
cggaatcgct gcgccaggag aaaacgaacg gtcctgaagc atgtgcgccc ggttcttcca     600
aaacacttat ctttaagatt gaagtagtat atatgactga aatttttaca aggttttttcc    660
ccataaaaca ggtgagctta tctcatcctt tgtttagga tgtacgtatt atatatgact      720
gaatattttt tatttcatt gaatgaagat tttcgacccc ccaaaaataa aaacggagg      780
gagtaccttt gtgccgtgta tatggactag agccatcggg acgttccgg agactgcgtg     840
gtgggggcga tggacgcaca acgaccgcat tttcggttgc cgactcgccg ttcgcatctg     900
gtaggcacga ctcgtcgggt tcggctcttg cgtgagccgt gacgtaacag accgttctc      960
ttccccgtc tggccatcca taaatccccc ctccatcggc ttccctttcc tcaatccagc     1020
accctgattc cgatcgaaaa gtccccgcaa gagcaagcga ccgatctcgt gaatctccgt    1080
caaggtatgc agcctcgctt cctcctcgct accgtttcaa ttctggagta ggtcgtagag    1140
gataccatgt tgatttgaca gagggagtag attagagact tgtagatcga agtgcggatg    1200
ttccatggta gatgatacca tgttgattc gattagatcg gattaaatct ttgtagatcg     1260
aagtgcgcat gttccatgaa ttgcctgtta ccagtagatt caagttttc tgtgttatag     1320
aggtgggatc tactcgttga gatgattagc tcctagagga caccatgccg ttttggaaaa    1380
tagatcagaa ccgtgtagat cgatgtgagc atgtgttcct gtagatccaa gttctttcgc    1440
atgttactag ttgtgatcta ttgtttgtgt aatacgctct cgatctatcc gtgtagattt    1500
cactcgatta ctgttactgt ggcttgatcg ttcatagttg ttcgttaggt ttgatcgaac    1560
agtgtctgaa cctaattgga tatgtattct tgatctatca acgtgtaggt ttcagtcatg    1620
tatttatgta ctccctccgt cccaaattaa ctgacgtgga ttttgtataa gaatctatac    1680
aaatccatgt cagttaattc gggatggagt accatattca ataatttgtt tattgctgtc    1740
cacttatgta ccatatgttt gttgttcctc atgtggattc tactaattat cattgattgg    1800
tgatcttcta ttttgctagt ttcctagctc aatctggtta ttcatgtaga gtgttgttg     1860
aaatcggaga ccatgcttgt tattagatag tttattgctt atcagtttca tgttctggtt    1920
gatgcaacac atattcatgt tcgctatctg gttgctgctt gatattctct gatttacatt    1980
cattataaga atatattctg ctctggttgt tgcttctcat gactttacct actcggtagg    2040
tgacttacct tttggtttac aattgtcaac tatgcag                             2077
```

<210> SEQ ID NO 16
<211> LENGTH: 1563
<212> TYPE: DNA
<213> ORGANISM: Brachypodium distachyon

<400> SEQUENCE: 16

```
ggcgtcagga ctggcgaagt ctggactctg cagggccgaa ctgctgaaga cgaagcagag      60
gaagagaaag ggaagtgttc gacttgtaat ttgtaggggt ttttttttaga ggaacttgta     120
atttgtaggt gggctggcct cgttggaaaa acgatgctgg ctggttgggc tgggccgatg     180
tacgcttgca acaacttgt ggcggcccgt tctggacgag caggagtttc ttttttgttc      240
tcacttttct ggtcttcttt agttacggag tacctttttgt tttttaaagg agttaccttt    300
tttttaggaa ttctttagtt accttttcgct tgctctcaaa aaatatttaa cttttcgcttt   360
ttttcattt aattttttgca actatttacg agtttcatga atgcttattt tccagcatat    420
cattatttgc aagtattttt atgccgtatg tattggacga gagccatcgg gactgttcca    480
gagactgcgt ggtggggacg ctcccaacc gccttttcta tctctgttcg catccggtgg    540
ccgacttggc tcgcgcgtga gccgtgacgt aacagacttg gtctcttccc catctggcca    600
tctataaatt cccccatcga tcgaccctcc ctttccccaa tccagcaccc ccgatcccga    660
tcgaaaattc tccgcaacag caagcgatcg atctagcgaa tccccgtcaa ggtatgtagc    720
ctctcgattc ctcctcagcc ctgccctcga tttggtgtac gcgttgagat gatgatctcg    780
tagatgtcta gatgacacca tgtcgatttg aaatagatca gatccgtgta gatcgatgag    840
ctcctgtgta cctgtggatt caagttattt tcgcatgcta ttgttgtgat ctactagatc    900
tagtgtgtgt attctatgct atcgatttct ccgtgtagat ttcactcgat tactgttact    960
gtggcttgat cggccataga tgttggttaa ggtttgatcg gttagtgttt gaacctgcgt   1020
ggatatctag catccatcta ttatcgtgta ggtttcgaac aaacaagcac tattattgta   1080
ctgatggttc gtctatggtt ggttttgacc gttttagtgt tgaacgagcc ttctgtattt   1140
gtttattgct gtccagtgat gtaccatgtt cgttgagtgt cggattatac taattattgt   1200
tgattgataa tcttgtagtt tgcttttcct aatttattta tcgtagtcct gatttgcctc   1260
agctgtgcct cacccgtgcg atggtcaatc aacttgttag cccaatctgc ttaatcatgt   1320
acatttgttg ttagaatcag agatcaagcc aattagctat cttattgctt atctgttcca   1380
tgttctgatc gatgtaacag tctacacttt tgctctgtgc tacttgatta aacattctg   1440
acttaaattc atgattggaa gtttcagatc tgattgttgc cttacttgac taatatctat   1500
tcatgtgaca cctctctgtc ttggtaactt accgctgttt gtttgtaatt tctgactatg  1560
cag                                                                1563
```

<210> SEQ ID NO 17
<211> LENGTH: 2600
<212> TYPE: DNA
<213> ORGANISM: Setaria italica

<400> SEQUENCE: 17

```
tgcgtctgga cgcacaagtc atagcattat cggctaaaat ttcttaattt ctaaattagt      60
catatcggct aagaaagtgg ggagcactat catttcgtag aacaagaaca aggtatcata     120
tatatatata tatataatat ttaaactttg ttaagtggaa tcaaagtgct agtattaatg    180
gagtttcatg tgcattaaat tttatgtcac atcagcaatt tgttgacttt ggcaaggtca    240
tttagggtgt gtttggaaga caggggctat taggagtatt aaacatagtc taattacaaa    300
```

```
actaattgca caaccgctaa gctgaatcgc gagatggatc tattaagctt aattagtcca    360
tgatttgaca atgtggtgct acaataacca tttgctaatg atggattact taggtttaat    420
agattcgtct cgtgatttag cctatgggtt ctgctattaa ttttgtaatt agctcatatt    480
tagttcttat aattagtatc cgaacatcca atgtgacatg ctaaagttta accctggtat    540
ccaaatgaag tcttatgaga gtttcatcac tccggtggta tatgtactta ggctccgttt    600
tcttccaccg acttattttt agcacccgtc acattgaatg tttagatact aattagaagt    660
attaaacgta gactatttac aaaatccatt acataagacg aatctaaacg gcgagacgaa    720
tctattaaac ctaattagtc catgatttga caatgtgttg ctacagtaaa catttgctaa    780
tgatggatta attaggctta atagattcgt ctcgccgttt agcctccact tatgtaatgg    840
gttttctaaa caatctacgt ttaatactcc taattagtat ctaaatattc aatgtgacac    900
gtgctaaaaa taagtcagtg aaggaagag  aacgtcccct tagttttcca tcttattaat    960
tgtacgatga aactgtgcag ccagatgatt gacaatcgca atacttcaac tagtgggcca   1020
tgcacatcag cgacgtgtaa cgtcgtgagt tgctgttccc gtagagaaat atcaactggt   1080
gggccacgca catcagcgtc gtgtaacgtg gacggaggag ccccgtgacg cgtcgacat    1140
cgaacggcca ccaaccacgg aaccacccgt ccccacctct cggaagctcc gctccacggc   1200
gtcgacatct aacggctacc agcaggcgta cgggttggag tggactcctt gcctctttgc   1260
gctggcggct tccggaaatt gcgtggcgga gacgaggcgg gctcgtctca cacggcacgg   1320
aagacgtcac gggttccttc cccacctctc ctcttcccca ccgccataaa tagccgaccc   1380
cctcgccttt ctccccaatc tcatctcgtc tcgtgttgtt cggagcacac cacccgcccc   1440
aaatcgttct tcccgcaagc ctcggcgatc cttcacccgc ttcaaggtac ggcgatcgtc   1500
ttcctcctct agatcggcgt gatctgcaag tagttgattt ggtagatggt taggatctgt   1560
gcactgaaga aatcatgtta gatccgcgat gtttctgttc gtagatggct gggaggtgga   1620
atttttgtgt agatctgata tgttctcctg tttatcttgt cacgctcctg cgatttgtgg   1680
ggatttagg  tcgttgatct gggaatcgtg gggttgcttc taggctgttc gtagatgagg   1740
tcgttctcac ggtttactgg atcattgcct agtagatcag ctcgggcttt cgtctttgta   1800
tatggtgccc atacttgcat ctatgatctg gttccgtggt gttacctagg tttctgcgcc   1860
tgattcgtcc gatcgatttt gttagcatgt ggtaaacgtt tggtcatggt ctgatttaga   1920
ttagagtcga ataggatgat ctcgatctag ctcttgggat taatatgcat gtgtcaccaa   1980
tctgttccgt ggttaagatg atgaatctat gcttagttaa tgggtgtaga tatatatgct   2040
gctgttcctc aatgatgccg tagcttttac ctgagcagca tggatcctcc tgttacttag   2100
gtagatgcac atgcttatag atcaagatat gtactgctac tgttggaatt ctttagtata   2160
cctgatgatc atccatgctc ttgttacttg ttttggtata cttggatgat ggcatgctgc   2220
tgcttttgt  tgatttgagc ccatccatat ctgcatatgt cacatgatta agatgattac   2280
gctgttctg  tatgatgcca tagctttat  gtgagcaaca tgcatcctcc tggttatatg   2340
cattaataga tggaagatat ctattgctac aatttgatga ttattttgta catacgatga   2400
tcaagcatgc tcttcatact ttgttgatat acttggataa tgaaatgctg ctgcacgttc   2460
attctatagc actaatgatg tgatgaacac gcacgacctg tttgtggcat ctgtttgaat   2520
gtgttgttgc tgttcactag agactgtttt attaacctac tgctagatac ttacccttct   2580
gtctgtttat tcttttgcag                                                2600
```

<210> SEQ ID NO 18
<211> LENGTH: 1602
<212> TYPE: DNA
<213> ORGANISM: Zea mays

<400> SEQUENCE: 18

| | | | | | |
|---|---|---|---|---|---|
| atgcagatct | ttgtgaaaac | cctgactggc | aagactatca | ccctcgaggt | ggagtcgtct | 60 |
| gacaccattg | acaacgttaa | ggccaagatc | caggacaagg | agggcatccc | ccagaccag | 120 |
| cagcggctca | tctttgctgg | caaacagctt | gaggacgggc | gcacgcttgc | tgactacaac | 180 |
| atccagaagg | agagcaccct | ccaccttgtg | ctccgtctca | ggggaggcat | gcagatcttt | 240 |
| gtgaaaaccc | tgaccggcaa | gactatcacc | ctcgaggtgg | agtcctctga | caccattgac | 300 |
| aacgtcaagg | ccaagatcca | ggacaaggag | ggcatccctc | agaccagca | gcggctcatc | 360 |
| tttgctggga | agcagcttga | ggacgggcgc | acgcttgccg | actacaacat | ccagaaggag | 420 |
| agcaccctcc | acttggtgct | gcgcctcagg | ggaggcatgc | agatcttcgt | gaagaccctg | 480 |
| accggcaaga | ctatcaccct | cgaggtggag | tcttcagaca | ccatcgacaa | cgtcaaggcc | 540 |
| aagatccagg | acaaggaggg | cattcccca | gaccagcagc | ggctcatctt | gctggaaag | 600 |
| cagcttgagg | acgggcgcac | gcttgccgac | tacaacatcc | agaaggagag | caccctccac | 660 |
| ttggtgctgc | gcctcagggg | aggcatgcag | atcttcgtga | agaccctgac | cggcaagact | 720 |
| atcaccctcg | aggtggagtc | ttcagacacc | atcgacaatg | tcaaggccaa | gatccaggac | 780 |
| aaggagggca | tcccaccgga | ccagcagcgt | tgatcttcg | ctggcaagca | gctggaggat | 840 |
| ggccgcaccc | ttgcggatta | caacatccag | aaggagagca | cctccacct | ggtgctccgt | 900 |
| ctcaggggtg | gtatgcagat | ctttgtgaag | acactcactg | gcaagacaat | cacccttgag | 960 |
| gtggagtctt | cggataccat | tgacaatgtc | aaggccaaga | tccaggacaa | ggagggcatc | 1020 |
| ccacccgacc | agcagcgcct | catcttcgcc | ggcaagcagc | tggaggatgg | ccgcaccctg | 1080 |
| gcggattaca | acatccagaa | ggagagcact | ctccacctgg | tgctccgcct | caggggtggc | 1140 |
| atgcagattt | tgtgaagac | attgactggc | aagaccatca | ccttggaggt | ggagagctct | 1200 |
| gacaccattg | acaatgtgaa | ggccaagatc | caggacaagg | agggcattcc | cccagaccag | 1260 |
| cagcgtctga | tctttgcggg | caagcagctg | gaggatggcc | gcactctcgc | ggactacaac | 1320 |
| atccagaagg | agagcaccct | tcaccttgtt | ctccgcctca | gaggtggtat | gcagatcttt | 1380 |
| gtaaagaccc | tgactggaaa | aaccataacc | ctggaggttg | agagctcgga | caccatcgac | 1440 |
| aatgtgaagg | cgaagatcca | ggacaaggag | ggcatccccc | cggaccagca | gcgtctgatc | 1500 |
| ttcgccggca | acagctgga | ggatggccgc | accctagcag | actacaacat | ccaaaaggag | 1560 |
| agcaccctcc | accttgtgct | ccgtctccgt | ggtggtcagt | aa | | 1602 |

<210> SEQ ID NO 19
<211> LENGTH: 4249
<212> TYPE: DNA
<213> ORGANISM: Brachypodium distachyon

<400> SEQUENCE: 19

| | | | | | |
|---|---|---|---|---|---|
| ctgctcgttc | agcccacagt | aacacgccgt | gcgacatgca | gatgccctcc | accacgccga | 60 |
| ccaaccccaa | gtccgccgcg | ctcgtccacg | gcgccatccg | catccgcgcg | tcaacgtcat | 120 |
| ccggaggagg | cgagcgcgat | gtcgacggcc | acgcggcgg | cggacacgac | ggcgacgccc | 180 |
| cgactccgcg | cgcgcgtcaa | ggctgcagtg | gcgtcgtggt | ggccgtccgc | ctgcacgaga | 240 |
| tccccgcgtg | gacgagcgcc | gcctccaccc | agcccctata | tcgagaaatc | aacggtgggc | 300 |

```
tcgagctcct cagcaacctc cccacccccc cttccgacca cgctcccttc ccccgtgccc    360
ctcttctccg taaacccgag ccgccgagaa caacaccaac gaaagggcga agagaatcgc    420
catagagagg agatgggcgg aggcggatag tttcagccat tcacggagaa atggggagga    480
gagaacacga catcatacgg acgcgaccct ctagctggct ggctgtccta aagaatcgaa    540
cggaatcgct gcgccaggag aaaacgaacg gtcctgaagc atgtgcgccc ggttcttcca    600
aaacacttat ctttaagatt gaagtagtat atatgactga aattttttaca aggttttttcc   660 ccataaaaca ggtgagctta tctcatcctt ttgtttagga tgtacgtatt atatatgact    720 gaatatttttt tatttttcatt gaatgaagat tttcgacccc ccaaaaataa aaacggagg    780 gagtaccttt gtgccgtgta tatggactag agccatcggg acgtttccgg agactgcgtg    840
gtgggggcga tggacgcaca acgaccgcat tttcggttgc cgactcgccg ttcgcatctg    900
gtaggcacga ctcgtcgggt tcggctcttg cgtgagccgt gacgtaacag acccgttctc    960
ttcccccgtc tggccatcca taaatccccc ctccatcggc ttcccttttcc tcaatccagc   1020 accctgattc cgatcgaaaa gtccccgcaa gagcaagcga ccgatctcgt gaatctccgt   1080
caaggtatgc agcctcgctt cctcctcgct accgtttcaa ttctggagta ggtcgtagag   1140
gataccatgt tgatttgaca gagggagtag attagatact tgtagatcga agtgcggatg   1200
ttccatggta gatgatacca tgttgatttc gattagatcg gattaaatct ttgtagatcg   1260
aagtgcgcat gttccatgaa ttgcctgtta ccagtagatt caagtttttc tgtgttatag   1320
aggtgggatc tactcgttga gatgattagc tcctagagga caccatgccg ttttggaaaa   1380
tagatcagaa ccgtgtagat cgatgtgagc atgtgttcct gtagatccaa gttctttcgc   1440
atgttactag ttgtgatcta ttgttttgtgt aatacgctct cgatctatcc gtgtagattt   1500
cactcgatta ctgttactgt ggcttgatcg ttcatagttg ttcgttaggt ttgatcgaac   1560
agtgtctgaa cctaattgga tatgtattct tgatctatca acgtgtaggt ttcagtcatg   1620
tatttatgta ctccctccgt cccaaattaa ctgacgtgga ttttgtataa gaatctatac   1680
aaatccatgt cagttaattc gggatggagt accatattca ataatttgtt tattgctgtc   1740
cacttatgta ccatatgttt gttgttcctc atgtggattc tactaattat cattgattgg   1800
tgatcttcta ttttgctagt ttcctagctc aatctggtta ttcatgtaga gtgttgttg   1860 aaatcggaga ccatgcttgt tattagatag tttattgctt atcagtttca tgttctggtt   1920
gatgcaacac atattcatgt tcgctatctg gttgctgctt gatattctct gatttacatt   1980
cattataaga atatattctg ctctggttgt tgcttctcat gactttacct actcggtagg   2040
tgacttacct tttggtttac aattgtcaac tatgcagatg cagatctttg tgaagaccct   2100
caccggcaag accatcaccc ttgaggtcga gtcttctgat acgatcgaca atgtcaaggc   2160
aaagatccag gacaaggagg gcatcccccc ggaccagcag cgtctcatct tcgccgggaa   2220
gcagctggag gatggccgca ccctggcaga ttacaacatc cagaaggagt ccaccctcca   2280
tctggtgctc aggctcaggg gtggcatgca aatctttgtg aagacccttta ctggcaagac   2340 catcacactc gaggtcgagt cgtctgacac gatcgacaat gtgaaggcaa agatccagga   2400
caaggagggc atcccccccag accagcagcg cctcatcttt gctggcaagc aactggaaga   2460
cggtcgcacc ctggcagatt acaatatcca gaaggagtcc accttgcacc ttgtgcttcg   2520
cctccgtggt ggcatgcaaa tctttgtcaa gaccttgaca ggcaagacca ttactctgga   2580
ggtcgagtcg tctgacacaa tcgataatgt gaaggcgaag atccaggaca aggagggaat   2640
```

| | |
|---|---|
| tccaccggac cagcagcgcc taatctttgc tggcaaacag cttgaggatg gccgcaccct | 2700 |
| ggcagattac aacatccaga aagaatccac tctgcacctg gtgcttcgcc tccgtggtgg | 2760 |
| catgcagatc tttgtcaaga ccttgacagg aagacaatc acactggagg tcgagtcgtc | 2820 |
| tgacacaatc gataatgtga aggcgaagat ccaggacaag gagggcattc accggacca | 2880 |
| gcagcgcctt atcttcgccg gcaagcagct tgaggatggc cgcacccttg ctgattacaa | 2940 |
| tatccagaag gaatccaccc tgcacctggt gcttcgcctc cgtggtggca tgcagatctt | 3000 |
| tgtcaagact ttgaccggga agaccattac actggaggtt gaatcttcag acaccatcga | 3060 |
| caacgtgaag gcgaagatcc aggacaagga gggcatcccc ccagaccagc agcgcctgat | 3120 |
| cttttgctggt aagcagcttg aggatggacg cactctggcg gattataaca tccagaagga | 3180 |
| gtctacccta cacctggtgc tccgcctccg tggtggccag taagtttgtc aaaaactggc | 3240 |
| ctacagtctg ctgcccctgt tggtctgccc cttggaagta gtcgtgtcta tggttatgtg | 3300 |
| agaagtcgtt gtgttctttc taatcccgta ctgtttgtgt gaacatcgc tgctgtcgta | 3360 |
| ttgcatcgtg aagaatcctg ttatgaataa gtgaacatga accttgttct gtgattacgg | 3420 |
| cttcgtggtt atgcgaacgt tcttacaaac gcaattgcac ctgatgtaaa atcgttttg | 3480 |
| ctagctgtat ggaacaagtg ctcatgatgt tcatgcaaga tgcaattcca gcttttgttg | 3540 |
| gtttgtcatc tttgtactgt gcttaccgca cataaagatt gcatcttgct tattgctttg | 3600 |
| ttgctttggt gctcgtccgc ttctcccttgc accttatcaa acctttgttt agattctctt | 3660 |
| cttatagcac ttggtaactc tcagctttac aacgccagta ctgtttctga atttcatga | 3720 |
| ctgataaagc tgatagatgg agtactaata tatgacatct ttccataaat gttcgggtgc | 3780 |
| agagatatgg aggccccagg atcctattta caggatgaac ctacctgggc cgctgtacgc | 3840 |
| atgacatccg cgagcaagtc tgaggttctc aatgtacaca tgaaattgat ttttgctgcg | 3900 |
| tttggcttgg ctgatcgttg catttgttct gattcatcag agttaaataa cggatatatc | 3960 |
| agcaaatatc cgcagcatcc acaccgacca cacgtccggt taacagagtc cccctgcctt | 4020 |
| gctttaatta ttacggagta ctccgctatt aatccttaga tatgtttcga aggaactcaa | 4080 |
| accttcctcc atctgcaaat ctcagtgctt caaaactgga attagataat tgaaaccttc | 4140 |
| attcggttgc aattcacaac tgcaaattga acagcactgt caatttcaat ttcgggttca | 4200 |
| cgattccacc gataggttga catgatccat gatccaccca ttgtacaac | 4249 |

<210> SEQ ID NO 20
<211> LENGTH: 3729
<212> TYPE: DNA
<213> ORGANISM: Brachypodium distachyon

<400> SEQUENCE: 20

| | |
|---|---|
| ggcgtcagga ctggcgaagt ctggactctg cagggccgaa ctgctgaaga cgaagcagag | 60 |
| gaagagaaag ggaagtgttc gacttgtaat ttgtaggggt ttttttaga ggaacttgta | 120 |
| atttgtaggt gggctggcct cgttggaaaa acgatgctgg ctggttgggc tgggccgatg | 180 |
| tacgcttgca aacaacttgt ggcggcccgt tctggacgag caggagtttc ttttttgttc | 240 |
| tcactttctt ggtcttcttt agttacggag taccttttgt tttttaaagg agttaccttt | 300 |
| ttttttaggaa ttcttttagtt acctttcgct tgctctcaaa aaatatttaa cttttcgcttt | 360 |
| ttttcattttt aattttttgca actatttacg agtttcatga atgcttattt tccagcatat | 420 |
| cattatttgc aagtattttt atgccgtatg tattggacga gagccatcgg gactgttcca | 480 |
| gagactgcgt ggtggggacg gctcccaacc gccttttcta tctctgttcg catccggtgg | 540 |

```
ccgacttggc tcgcgcgtga gccgtgacgt aacagacttg gtctcttccc catctggcca    600
tctataaatt cccccatcga tcgaccctcc ctttccccaa tccagcaccc ccgatcccga    660
tcgaaaattc tccgcaacag caagcgatcg atctagcgaa tccccgtcaa ggtatgtagc    720
ctctcgattc ctcctcagcc ctgccctcga tttggtgtac gcgttgagat gatgatctcg    780
tagatgtcta gatgacacca tgtcgatttg aaatagatca gatccgtgta gatcgatgag    840
ctcctgtgta cctgtggatt caagttattt tcgcatgcta ttgttgtgat ctactagatc    900
tagtgtgtgt attctatgct atcgatttct ccgtgtagat ttcactcgat tactgttact    960
gtggcttgat cggccataga tgttggttaa ggtttgatcg gttagtgttt gaacctgcgt   1020
ggatatctag catccatcta ttatcgtgta ggtttcgaac aaacaagcac tattattgta   1080
ctgatggttc gtctatggtt ggttttgacc gttttagtgt tgaacgagcc ttctgtattt   1140
gtttattgct gtccagtgat gtaccatgtt cgttgagtgt cggattatac taattattgt   1200
tgattgataa tcttgtagtt tgcttttcct aatttattta tcgtagtcct gatttgcctc   1260
agctgtgcct cacccgtgcg atggtcaatc aacttgttag cccaatctgc ttaatcatgt   1320
acatttgttg ttagaatcag agatcaagcc aattagctat cttattgctt atctgttcca   1380
tgttctgatc gatgtaacag tctacacttt tgctctgtgc tacttgatta aaacattctg   1440 acttaaaattc atgattggaa gtttcagatc tgattgttgc cttacttgac taatatctat   1500
tcatgtgaca cctctctgtc ttggtaactt accgctgttt gtttgtaatt tctgactatg   1560
cagatgcaga tctttgtgaa gaccctcact ggcaaaacca tcacccttga ggtcgagtcg   1620
tccgacacga tcgacaacgt caaggcaaag atccaggaca aggagggcat tcctccagac   1680
cagcagcgcc tcatctttgc tggaaagcag cttgaggacg gccgcaccct cgccgactac   1740
aacatccaga aggagtccac cctccacctg gtcctgaggc tccgtggtgg catgcagatc   1800
ttcgtcaaga cccttaccgg caagaccatc acgctggagg tcgagtcctc tgacacgatc   1860
gacaatgtga aggcgaagat ccaggataag gagggcatcc ccccggacca gcagcgcctc   1920
atctttgccg gcaagcagct tgaggacggc cgtaccctcg ccgactacaa catccagaag   1980
gaatccacac tccatctggt gctcaggctg cgtggtggca tgcagatctt cgtcaagacc   2040
ctaaccggca agaccatcac tctggaggtt gagtcctctg acacgatcga caatgtgaag   2100
gcaaagatcc aggataagga gggcattccc ccggaccagc agcgcctcat cttcgctggc   2160
aagcagcttg aggatggccg caccctggca gattacaata tccagaagga atccaccttg   2220
cacctggtgc ttcgcctccg tggtggcatg cagatctttg taaagacctt gactggcaag   2280
acaattaccc tggaggttga gtcgtccgac acaattgaca atgtcaaggc gaagatccag   2340
gacaaggagg gcatcccacc ggaccagcag cgcctcatct tcgccggcaa gcagcttgag   2400
gatggtcgca cccttgcaga ttacaatatc cagaaggaat ccactctgca tctggtgctt   2460
cgtctccgcg gtggaatgca gatcttcgtt aagacgttga cagggaagac catcacactg   2520
gaggttgaat cttcggacac cattgacaac gtgaaggcaa agatccagga caaggagggc   2580
atccccccag accagcagcg cctcatcttt gctggtaagc agcttgagga tggccgcacc   2640
cttgcagatt acaacattca gaaggagtcc accctgcacc tggtgctccg tctccgtggt   2700
gggcagtaag cttctgccga actggttcac agtctgctgc ccttggtggt ctgccccttg   2760
gtggtcatgc cttttgttat gtgtcttgcg tcccaatcct gtatcgtttg tgtgaacatc   2820
tctgctgctg tatagcagct tgaatcctgt tatgaatttg tgaacctgaa ccttgttccg   2880
```

| | |
|---|---|
| tgaatcatgt tatgaataag tgaacctgaa ccttgttccg tgattattgt tacaatctgt | 2940 |
| tgtgccgtat ggttggtcgt gtgtgattta tgttgaactg agaaccaag ttcgttccag | 3000 |
| gacatattgc aacctaagct aaaccatgta gaactacttg ttctgggaga cataaaacgt | 3060 |
| catttttatg cattcgtaac atttaagcat actacaataa ttgtattgtc cttttcctac | 3120 |
| tcatccttga aaccatatgc ctcttctcag cgcctctaca tgcagtgtgc tcagaacaaa | 3180 |
| caggccctgc cagctgcttt tcaattttcc aattaataac cacaatagtc ggactatggc | 3240 |
| atctgtgggt gactatgcaa gatgttgctg tcaggtctct gaaacttttc ccatgtatct | 3300 |
| gttgaaatta cccagtaaat tcatgcctct atttaatctg gcatggttga ttttcaaaca | 3360 |
| gaatgtgttt ttttttgttc tggaagctat attggtaaat aaatacaaag ctggagtgtg | 3420 |
| attatatttc aacagatat tcaagaaaat ctcagttgat ttatttacta ctgtagtata | 3480 |
| tatatatatc ttacagttga cttctcatat ttcaaacgac atgtgagcac attgttcagt | 3540 |
| ttcttaggat gtgttgtgtg ctcaaaggtg taattttgca ttctgccctc cgagtaaaca | 3600 |
| ctacacgtat ttttttgagt ggcagtgcat ttgattacaa ggcaacaaca acaaaaacct | 3660 |
| atggcaagat atccttctta gaggctgcca ggatcatttt gactgaacta tgtaaggctg | 3720 |
| aagaaaagg | 3729 |

<210> SEQ ID NO 21
<211> LENGTH: 5234
<212> TYPE: DNA
<213> ORGANISM: Setaria italica

<400> SEQUENCE: 21

| | |
|---|---|
| tgcgtctgga cgcacaagtc atagcattat cggctaaaat ttcttaattt ctaaattagt | 60 |
| catatcggct aagaaagtgg ggagcactat catttcgtag aacaagaaca aggtatcata | 120 |
| tatatatata tatataatat ttaaactttg ttaagtggaa tcaaagtgct agtattaatg | 180 |
| gagtttcatg tgcattaaat tttatgtcac atcagcaatt ttgttgactt ggcaaggtca | 240 |
| tttagggtgt gtttggaaga caggggctat taggagtatt aaacatagtc taattacaaa | 300 |
| actaattgca caaccgctaa gctgaatcgc gagatggatc tattaagctt aattagtcca | 360 |
| tgatttgaca atgtggtgct acaataacca tttgctaatg atggattact taggtttaat | 420 |
| agattcgtct cgtgatttag cctatgggtt ctgctattaa ttttgtaatt agctcatatt | 480 |
| tagttcttat aattagtatc cgaacatcca atgtgacatg ctaaagttta accctggtat | 540 |
| ccaaatgaag tcttatgaga gtttcatcac tccggtggta tatgtactta ggctccgttt | 600 |
| tcttccaccg acttatttt agcacccgtc acattgaatg tttagatact aattagaagt | 660 |
| attaaacgta gactatttac aaaatccatt acataagacg aatctaaacg gcagacgaa | 720 |
| tctattaaac ctaattagtc catgatttga caatgtgttg ctacagtaaa catttgctaa | 780 |
| tgatggatta attaggctta atagattcgt ctcgccgttt agcctccact tatgtaatgg | 840 |
| gttttctaaa caatctacgt ttaatactcc taattagtat ctaaatattc aatgtgacac | 900 |
| gtgctaaaaa taagtcagtg gaaggaagag aacgtcccct tagttttcca tcttattaat | 960 |
| tgtacgatga aactgtgcag ccagatgatt gacaatcgca atacttcaac tagtgggcca | 1020 |
| tgcacatcag cgacgtgtaa cgtcgtgagt tgctgttccc gtagagaaat atcaactggt | 1080 |
| gggccacgca catcagcgtc gtgtaacgtg gacggaggag cccgtgacg gcgtcgacat | 1140 |
| cgaacggcca ccaaccacgg aaccaccgt ccccacctct cggaagctcc gctccacggc | 1200 |
| gtcgacatct aacggctacc agcaggcgta cgggttggag tggactcctt gcctcttttgc | 1260 |

-continued

```
gctggcggct tccggaaatt gcgtggcgga gacgaggcgg gctcgtctca cacggcacgg    1320
aagacgtcac gggttccttc cccacctctc ctcttcccca ccgccataaa tagccgaccc    1380
cctcgccttt ctccccaatc tcatctcgtc tcgtgttgtt cggagcacac cacccgcccc    1440
aaatcgttct tcccgcaagc ctcggcgatc cttcacccgc ttcaaggtac ggcgatcgtc    1500
ttcctcctct agatcggcgt gatctgcaag tagttgattt ggtagatggt taggatctgt    1560
gcactgaaga aatcatgtta gatccgcgat gtttctgttc gtagatggct gggaggtgga    1620
atttttgtgt agatctgata tgttctcctg tttatcttgt cacgctcctg cgatttgtgg    1680
ggattttagg tcgttgatct gggaatcgtg gggttgcttc taggctgttc gtagatgagg    1740
tcgttctcac ggtttactgg atcattgcct agtagatcag ctcgggcttt cgtctttgta    1800
tatggtgccc atacttgcat ctatgatctg gttccgtggt gttacctagg tttctgcgcc    1860
tgattcgtcc gatcgatttt gttagcatgt ggtaaacgtt tggtcatggt ctgatttaga    1920
ttagagtcga ataggatgat ctcgatctag ctcttgggat taatatgcat gtgtcaccaa    1980
tctgttccgt ggttaagatg atgaatctat gcttagttaa tgggtgtaga tatatatgct    2040
gctgttcctc aatgatgccg tagctttac ctgagcagca tggatcctcc tgttacttag    2100
gtagatgcac atgcttatag atcaagatat gtactgctac tgttggaatt ctttagtata    2160
cctgatgatc atccatgctc ttgttacttg ttttggtata cttggatgat ggcatgctgc    2220
tgctttttgt tgatttgagc ccatccatat ctgcatatgt cacatgatta agatgattac    2280 gctgttctg tatgatgcca tagcttttat gtgagcaaca tgcatcctcc tggttatatg    2340
cattaataga tggaagatat ctattgctac aatttgatga ttatttttgta catacgatga    2400 tcaagcatgc tcttcatact ttgttgatat acttggataa tgaaatgctg ctgcacgttc    2460
attctatagc actaatgatg tgatgaacac gcacgacctg tttgtggcat ctgtttgaat    2520
gtgttgttgc tgttcactag agactgtttt attaacctac tgctagatac ttacccttct    2580
gtctgtttat tcttttgcag atgcagatct ttgtcaagac cctcaccggc aagaccatca    2640
ccctcgaggt ggagtcttct gacaccattg acaacgtcaa ggccaagatc caggacaagg    2700
aaggcattcc cccggatcag cagcggctca tctttgccgg caagcagctt gaggatgggc    2760
gcaccctggc tgactacaac atccagaagg agagcaccct ccacctggtg ctccgtctca    2820
ggggaggcat gcagatcttt gtgaagacct tgactggcaa gaccatcacc cttgaggtgg    2880
agtcttccga caccatcgac aacgtcaagg ccaagatcca ggacaaggag gcatccccc    2940 cggaccagca gaggctcatc tttgcgggca agcagcttga ggatgacgc accctggctg    3000 actataacat ccagaaggag agcaccctcc atctggtgct ccgtctcagg ggaggcatgc    3060
agatcttcgt gaagactctc actggcaaga ccatcaccct cgaggtggag tcttccgaca    3120
ccatcgacaa cgtcaaggcc aagatccagg acaaggaggg catcccccca gaccagcaga    3180
ggctcatctt tgctggcaag cagcttgagg acggacgcac cctggctgac tataacatcc    3240
agaaggagag caccctccac ctggtgctcc gcctgagggg tgggatgcag atctttgtga    3300
agactttgac tggcaagacc attactttgg aggttgagag ctccgacacc atcgacaacg    3360
tgaaggccaa gatccaggac aaggaaggca tccccccgga ccagcagagg ctcatcttcg    3420
ccggcaagca gcttgaggac ggacgcaccc tggctgacta aacatccag aaggagagca    3480 ccctccacct ggtgctccgt ctcaggggag gcatgcagat cttcgtgaag accctcactg    3540
gcaagaccat caccttgag gtggagtctt ccgacaccat cgacaatgtc aaggccaaga    3600
```

```
tccaggacaa ggagggcatc cccccagacc agcagagact catctttgca ggcaagcagc   3660
ttgaggacgg acgcaccctg gctgactaca acatccagaa ggagagcacc ctccacctgg   3720
tgctccgtct caggggaggc atgcagatct tcgtgaagac cctcactggc aagaccatca   3780
ccctcgaggt ggagtcttct gacaccatcg acaacgtcaa ggccaagatc caggacaagg   3840
agggcatccc cccggaccag cagcgtctta tctttgccgg caagcagctg gaggatggcc   3900
gcacccttgc ggattacaat atccagaagg agagcaccct ccatctggtg ctccgtctga   3960
ggggtgggat gcagatattc gtgaagactt tgaccggcaa gaccatcact ttggaggttg   4020
agagctccga caccattgac aatgtgaagg ccaagatcca ggacaaggag ggtatccccc   4080
cggaccagca gcgtctgatc ttcgccggca agcaactgga ggatggccgc accctggcgg   4140
actacaatat ccagaaggag tccaccctcc acctggtgct ccgcctccgt ggtggtcagt   4200
aagcccatcg gtcatggatg cttctactgt acctgggtcg tctggtctct gcctgtgtca   4260
cctttgaagt acctgtgtcg ggattgtgtt tggtcatgaa ctgcagtttg tctttgatgt   4320
tcttttgtct ggtcttatga actggttgta tctgtatgtt tactgtaaac tgttgttgcg   4380
gtgcagcagt atggcatccg aatgaataaa tgatgtttgg acttaaatct gtactctgtt   4440
tgttttcggt tatgccagtt ctatattgcc tgagatcaga atgtttagct tttgagttct   4500
gtttggcttg tggtcgactc ctgtttctta cttgaggcgt aactctgttc tggcaaactc   4560
aaatgtctaa ctgaatgttt taggacttaa ttgttggaca gattaacgtg tttggtttgt   4620
ttctagattg tgattcggaa ggcttgttag ttgtggaatc aaggagagca gctaggtctg   4680
tgcagaacgt tattttggat ttaagccttc tcagattatg ccattactct aaacctaatg   4740
atatcatatt tcactcgggg atgttggagt agtcttttct ttctcctgca gacaaaatga   4800
ttttgctttc gtgtgtgtac atgattttgt gcaactgttg caacaactga agtagacaag   4860
ttttgacctc accagaagaa tgaaaaagat tttggaattt gttacatcga caaaccattg   4920
taacttggcc catcagaatg cacagaagag cggctacaaa ttgacatgcg ttgcaaactt   4980
tgcaatagtt gatgcacatg tttgccattg cctgccagtc ttaggaaaag tgtgtggttc   5040
gagaaatcta agcatatgtg ctctgctcac attgcgtgga acccacacag ctttgtcaca   5100
ctcttgtcca ctccagaagt cattcctggc gctgtttacc cctggtaaaa ggtaaccgaa   5160
aacttctcaa ggctgtaccc aaaactggaa ggaaatttgg aggaaatctt tgcttttgat   5220
cggctcactc tttc                                                    5234
```

<210> SEQ ID NO 22
<211> LENGTH: 685
<212> TYPE: PRT
<213> ORGANISM: Zea mays

<400> SEQUENCE: 22

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80
```

-continued

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
        130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
        210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
            275                 280                 285

Ile Gln Lys Glu Ser Thr Leu His Leu Val Leu Arg Leu Arg Gly Gly
        290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
            355                 360                 365

Ser Thr Leu His Leu Val Leu Arg Leu Arg Gly Gly Met Gln Ile Phe
        370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
        435                 440                 445

Leu Val Leu Arg Leu Arg Gly Gly Met Gln Ile Phe Val Lys Thr Leu
        450                 455                 460

Thr Gly Lys Thr Ile Thr Leu Glu Val Glu Ser Ser Asp Thr Ile Asp
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu

```
                500             505             510
Ala Asp Tyr Asn Ile Gln Lys Glu Ser Thr Leu His Leu Val Leu Arg
            515             520             525

Leu Arg Gly Gly Met Gln Ile Phe Val Lys Thr Leu Thr Gly Lys Thr
            530             535             540

Ile Thr Leu Glu Val Glu Ser Ser Asp Thr Ile Asp Asn Val Lys Ala
545             550             555             560

Lys Ile Gln Asp Lys Glu Gly Ile Pro Pro Asp Gln Gln Arg Leu Ile
            565             570             575

Phe Ala Gly Lys Gln Leu Glu Asp Gly Arg Thr Leu Ala Asp Tyr Asn
            580             585             590

Ile Gln Lys Glu Ser Thr Leu His Leu Val Leu Arg Leu Arg Gly Gly
            595             600             605

Met Gln Ile Phe Val Lys Thr Leu Thr Gly Lys Thr Ile Thr Leu Glu
            610             615             620

Val Glu Ser Ser Asp Thr Ile Asp Asn Val Lys Ala Lys Ile Gln Asp
625             630             635             640

Lys Glu Gly Ile Pro Pro Asp Gln Gln Arg Leu Ile Phe Ala Gly Lys
            645             650             655

Gln Leu Glu Asp Gly Arg Thr Leu Ala Asp Tyr Asn Ile Gln Lys Glu
            660             665             670

Ser Thr Leu His Leu Val Leu Arg Leu Arg Gly Gly Gln
            675             680             685

<210> SEQ ID NO 23
<211> LENGTH: 685
<212> TYPE: PRT
<213> ORGANISM: Setaria italica

<400> SEQUENCE: 23

Met Gln Ile Phe Val Lys Thr Leu Thr Gly Lys Thr Ile Thr Leu Glu
1               5               10              15

Val Glu Ser Ser Asp Thr Ile Asp Asn Val Lys Ala Lys Ile Gln Asp
            20              25              30

Lys Glu Gly Ile Pro Pro Asp Gln Gln Arg Leu Ile Phe Ala Gly Lys
            35              40              45

Gln Leu Glu Asp Gly Arg Thr Leu Ala Asp Tyr Asn Ile Gln Lys Glu
        50              55              60

Ser Thr Leu His Leu Val Leu Arg Leu Arg Gly Gly Met Gln Ile Phe
65              70              75              80

Val Lys Thr Leu Thr Gly Lys Thr Ile Thr Leu Glu Val Glu Ser Ser
            85              90              95

Asp Thr Ile Asp Asn Val Lys Ala Lys Ile Gln Asp Lys Glu Gly Ile
            100             105             110

Pro Pro Asp Gln Gln Arg Leu Ile Phe Ala Gly Lys Gln Leu Glu Asp
            115             120             125

Gly Arg Thr Leu Ala Asp Tyr Asn Ile Gln Lys Glu Ser Thr Leu His
        130             135             140

Leu Val Leu Arg Leu Arg Gly Gly Met Gln Ile Phe Val Lys Thr Leu
145             150             155             160

Thr Gly Lys Thr Ile Thr Leu Glu Val Glu Ser Ser Asp Thr Ile Asp
            165             170             175

Asn Val Lys Ala Lys Ile Gln Asp Lys Glu Gly Ile Pro Pro Asp Gln
            180             185             190
```

```
Gln Arg Leu Ile Phe Ala Gly Lys Gln Leu Glu Asp Gly Arg Thr Leu
            195                 200                 205
Ala Asp Tyr Asn Ile Gln Lys Glu Ser Thr Leu His Leu Val Leu Arg
    210                 215                 220
Leu Arg Gly Gly Met Gln Ile Phe Val Lys Thr Leu Thr Gly Lys Thr
225                 230                 235                 240
Ile Thr Leu Glu Val Glu Ser Ser Asp Thr Ile Asp Asn Val Lys Ala
            245                 250                 255
Lys Ile Gln Asp Lys Glu Gly Ile Pro Pro Asp Gln Gln Arg Leu Ile
                260                 265                 270
Phe Ala Gly Lys Gln Leu Glu Asp Gly Arg Thr Leu Ala Asp Tyr Asn
        275                 280                 285
Ile Gln Lys Glu Ser Thr Leu His Leu Val Leu Arg Leu Arg Gly Gly
    290                 295                 300
Met Gln Ile Phe Val Lys Thr Leu Thr Gly Lys Thr Ile Thr Leu Glu
305                 310                 315                 320
Val Glu Ser Ser Asp Thr Ile Asp Asn Val Lys Ala Lys Ile Gln Asp
            325                 330                 335
Lys Glu Gly Ile Pro Pro Asp Gln Gln Arg Leu Ile Phe Ala Gly Lys
                340                 345                 350
Gln Leu Glu Asp Gly Arg Thr Leu Ala Asp Tyr Asn Ile Gln Lys Glu
        355                 360                 365
Ser Thr Leu His Leu Val Leu Arg Leu Arg Gly Gly Met Gln Ile Phe
    370                 375                 380
Val Lys Thr Leu Thr Gly Lys Thr Ile Thr Leu Glu Val Glu Ser Ser
385                 390                 395                 400
Asp Thr Ile Asp Asn Val Lys Ala Lys Ile Gln Asp Lys Glu Gly Ile
            405                 410                 415
Pro Pro Asp Gln Gln Arg Leu Ile Phe Ala Gly Lys Gln Leu Glu Asp
                420                 425                 430
Gly Arg Thr Leu Ala Asp Tyr Asn Ile Gln Lys Glu Ser Thr Leu His
        435                 440                 445
Leu Val Leu Arg Leu Arg Gly Gly Met Gln Ile Phe Val Lys Thr Leu
    450                 455                 460
Thr Gly Lys Thr Ile Thr Leu Glu Val Glu Ser Ser Asp Thr Ile Asp
465                 470                 475                 480
Asn Val Lys Ala Lys Ile Gln Asp Lys Glu Gly Ile Pro Pro Asp Gln
            485                 490                 495
Gln Arg Leu Ile Phe Ala Gly Lys Gln Leu Glu Asp Gly Arg Thr Leu
                500                 505                 510
Ala Asp Tyr Asn Ile Gln Lys Glu Ser Thr Leu His Leu Val Leu Arg
        515                 520                 525
Leu Arg Gly Gly Met Gln Ile Phe Val Lys Thr Leu Thr Gly Lys Thr
    530                 535                 540
Ile Thr Leu Glu Val Glu Ser Ser Asp Thr Ile Asp Asn Val Lys Ala
545                 550                 555                 560
Lys Ile Gln Asp Lys Glu Gly Ile Pro Pro Asp Gln Gln Arg Leu Ile
            565                 570                 575
Phe Ala Gly Lys Gln Leu Glu Asp Gly Arg Thr Leu Ala Asp Tyr Asn
                580                 585                 590
Ile Gln Lys Glu Ser Thr Leu His Leu Val Leu Arg Leu Arg Gly Gly
        595                 600                 605
Met Gln Ile Phe Val Lys Thr Leu Thr Gly Lys Thr Ile Thr Leu Glu
```

```
                   610             615             620
Val Glu Ser Ser Asp Thr Ile Asp Asn Val Lys Ala Lys Ile Gln Asp
625                 630                 635                 640

Lys Glu Gly Ile Pro Pro Asp Gln Gln Arg Leu Ile Phe Ala Gly Lys
                645                 650                 655

Gln Leu Glu Asp Gly Arg Thr Leu Ala Asp Tyr Asn Ile Gln Lys Glu
            660                 665                 670

Ser Thr Leu His Leu Val Leu Arg Leu Arg Gly Gly Gln
        675                 680                 685

<210> SEQ ID NO 24
<211> LENGTH: 533
<212> TYPE: PRT
<213> ORGANISM: Brachypodium distachyon

<400> SEQUENCE: 24

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
                100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
        130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
        210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
        290                 295                 300
```

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
            325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
            355                 360                 365

Ser Thr Leu His Leu Val Leu Arg Leu Arg Gly Gly Met Gln Ile Phe
            370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
            435                 440                 445

Leu Val Leu Arg Leu Arg Gly Gly Met Gln Ile Phe Val Lys Thr Leu
450                 455                 460

Thr Gly Lys Thr Ile Thr Leu Glu Val Glu Ser Ser Asp Thr Ile Asp
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
            500                 505                 510

Ala Asp Tyr Asn Ile Gln Lys Glu Ser Thr Leu His Leu Val Leu Arg
            515                 520                 525

Leu Arg Gly Gly Gln
            530

<210> SEQ ID NO 25
<211> LENGTH: 533
<212> TYPE: PRT
<213> ORGANISM: Brachypodium distachyon

<400> SEQUENCE: 25

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
            85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
130                 135                 140

```
Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
            165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
            210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
            245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
            275                 280                 285

Ile Gln Lys Glu Ser Thr Leu His Leu Val Leu Arg Leu Arg Gly Gly
            290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
            325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
            355                 360                 365

Ser Thr Leu His Leu Val Leu Arg Leu Arg Gly Gly Met Gln Ile Phe
            370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
            435                 440                 445

Leu Val Leu Arg Leu Arg Gly Gly Met Gln Ile Phe Val Lys Thr Leu
            450                 455                 460

Thr Gly Lys Thr Ile Thr Leu Glu Val Glu Ser Ser Asp Thr Ile Asp
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
            500                 505                 510

Ala Asp Tyr Asn Ile Gln Lys Glu Ser Thr Leu His Leu Val Leu Arg
            515                 520                 525

Leu Arg Gly Gly Gln
    530

<210> SEQ ID NO 26
<211> LENGTH: 685
```

```
<212> TYPE: PRT
<213> ORGANISM: Artificial Sequence
<220> FEATURE:
<223> OTHER INFORMATION: consensus sequence

<400> SEQUENCE: 26

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Met Gln Ile Phe
    370                 375                 380
```

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
            435                 440                 445

Leu Val Leu Arg Leu Arg Gly Met Gln Ile Phe Val Lys Thr Leu
    450                 455                 460

Thr Gly Lys Thr Ile Thr Leu Glu Val Glu Ser Ser Asp Thr Ile Asp
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
            500                 505                 510

Ala Asp Tyr Asn Ile Gln Lys Glu Ser Thr Leu His Leu Val Leu Arg
    515                 520                 525

Leu Arg Gly Gly Met Gln Ile Phe Val Lys Thr Leu Thr Gly Lys Thr
    530                 535                 540

Ile Thr Leu Glu Val Glu Ser Ser Asp Thr Ile Asp Asn Val Lys Ala
545                 550                 555                 560

Lys Ile Gln Asp Lys Glu Gly Ile Pro Pro Asp Gln Gln Arg Leu Ile
            565                 570                 575

Phe Ala Gly Lys Gln Leu Glu Asp Gly Arg Thr Leu Ala Asp Tyr Asn
            580                 585                 590

Ile Gln Lys Glu Ser Thr Leu His Leu Val Leu Arg Leu Arg Gly Gly
            595                 600                 605

Met Gln Ile Phe Val Lys Thr Leu Thr Gly Lys Thr Ile Thr Leu Glu
    610                 615                 620

Val Glu Ser Ser Asp Thr Ile Asp Asn Val Lys Ala Lys Ile Gln Asp
625                 630                 635                 640

Lys Glu Gly Ile Pro Pro Asp Gln Gln Arg Leu Ile Phe Ala Gly Lys
            645                 650                 655

Gln Leu Glu Asp Gly Arg Thr Leu Ala Asp Tyr Asn Ile Gln Lys Glu
            660                 665                 670

Ser Thr Leu His Leu Val Leu Arg Leu Arg Gly Gly Gln
            675                 680                 685

<210> SEQ ID NO 27
<211> LENGTH: 1986
<212> TYPE: DNA
<213> ORGANISM: Zea mays

<400> SEQUENCE: 27
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg ttttttataga ctaatttttt tagtacatct attttattct attttagcct    420

```
ctaaattaag aaaactaaaa ctctatttta gttttttat ttaataattt agatataaaa    480
tagaataaaa taaagtgact aaaaattaaa caaatacct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctccccccc ccccctctc taccttctct   1020
agatcggcgt tccggtccat ggttagggcc cggtagttct acttctgttc atgtttgtgt   1080
tagatccgtg tttgtgttag atccgtgctg ctagcgttcg tacacggatg cgacctgtac   1140
gtcagacacg ttctgattgc taacttgcca gtgtttctct ttggggaatc ctgggatggc   1200
tctagccgtt ccgcagacgg gatcgatttc atgatttttt ttgtttcgtt gcatagggtt   1260
tggtttgccc ttttccttta tttcaatata tgccgtgcac ttgtttgtcg ggtcatcttt   1320
tcatgctttt ttttgtcttg gttgtgatga tgtggtctgg ttgggcggtc gttctagatc   1380
ggagtagaat tctgtttcaa actacctggt ggatttatta attttggatc tgtatgtgtg   1440
tgccatacat attcatagtt acgaattgaa gatgatggat ggaaatatcg atctaggata   1500
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattattttg atcttgatat   1860
acttggatga tggcatatgc agcagctata tgtggatttt tttagccctg ccttcatacg   1920
ctatttattt gcttggtact gtttcttttg tcgatgctca ccctgttgtt tggtgttact   1980
tctgca                                                              1986
```

<210> SEQ ID NO 28
<211> LENGTH: 21
<212> TYPE: DNA
<213> ORGANISM: Artificial Sequence
<220> FEATURE:
<223> OTHER INFORMATION: nucleotide primer

<400> SEQUENCE: 28
cgtgttggga aagaacttgg a                                              21

<210> SEQ ID NO 29
<211> LENGTH: 18
<212> TYPE: DNA
<213> ORGANISM: Artificial Sequence
<220> FEATURE:
<223> OTHER INFORMATION: nucleotide primer

<400> SEQUENCE: 29
ccgtggttgg cttggtct                                                  18

<210> SEQ ID NO 30
<211> LENGTH: 15
<212> TYPE: DNA
<213> ORGANISM: Artificial Sequence
<220> FEATURE:
<223> OTHER INFORMATION: nucleotide primer

<400> SEQUENCE: 30 cactcccac tgcct                                                       15

<210> SEQ ID NO 31
<211> LENGTH: 18
<212> TYPE: DNA
<213> ORGANISM: Artificial Sequence
<220> FEATURE:
<223> OTHER INFORMATION: nucleotide primer

<400> SEQUENCE: 31
tggcggacga cgacttgt                                                   18

<210> SEQ ID NO 32
<211> LENGTH: 19
<212> TYPE: DNA
<213> ORGANISM: Artificial Sequence
<220> FEATURE:
<223> OTHER INFORMATION: nucleotide primer

<400> SEQUENCE: 32
aaagtttgga ggctgccgt                                                  19

<210> SEQ ID NO 33
<211> LENGTH: 21
<212> TYPE: DNA
<213> ORGANISM: Artificial Sequence
<220> FEATURE:
<223> OTHER INFORMATION: nucleotide primer

<400> SEQUENCE: 33
cgagcagacc gccgtgtact t                                               21

<210> SEQ ID NO 34
<211> LENGTH: 4105
<212> TYPE: DNA
<213> ORGANISM: Panicum virgatum

<400> SEQUENCE: 34
ttgaatttta atttcaaatt ttgcagggta gtagtggaca tcacaataca tatttagaaa     60 aagtttata atttcctcc gttagtttc ataatttt gaactccaac gattaatcta        120
ttattaaata tcccgatcta tcaaataat gataaaaatt tatgattaat ttttctaaca    180
tgtgttatgg tgtgtactat cgtcttataa aatttcaact taaaactcca cctatacatg    240
gagaaatgaa aaagacgaat tacagtaggg agtaatttga accaaatgga atagtttgag    300
ggtaaaatga actaaacaat agtttaggag gttattcaga ttttagttat agttgagagg    360
agtaatttag actttttcct atcttgaatt gttgacggct ctcctatcgg atatcggatg    420
gagtctttca gcccaacata acttcattcg ggcccaaacg ttcgtccatc cagcctaggg    480
agaacatttt gcccatgata tctgtttttc tttttttcta ttttcactgg tattatagga    540
gggaaatata caacgtgttc acctttggtt tcattcttgt tccatctgaa tttatctaaa    600
actgtgtttg aacttcgtaa gaattttgtt cgatctgtcc ggtacatcgt gttgataggt    660
ggcctccgag attcttcttt ttaaccggca aagtaaaata atctcagctc cagcctaacg    720

```
tcaattatca gagagagaaa aaaatatttt tttatgattg atcggaaacc aaccgcctta    780
cgtgtcgatc ctggttcctg gccggcacgg cggaggaaag cgaccgacct cgcaacgccg    840
gcgcacggcg ccgccgtgtt ggacttggtc tcccgcgact ccgtgggcct cggcttatcg    900
ccgccgctcc atctcaaccg tccgcttgga cacgtgaaag ttgatccgtc gcgcaccagc    960
ctcggaggta acctaactgc ccgtactata atccgggat ccggcctctc caatccccat   1020
cgccacaagt tcgcgatctc tcgatttcac aaatcgccga gaagacccga gcagagaagt   1080
tccctccgat cgccttgcca aggtactcct acctaatcct ccttaactga tctctcctct   1140
atcacgttgg taatcttcga atgatctgct gcctggctcg ctgttccccc tcgttatgca   1200
ctgtttccat cacgagtttt ttttttcatc atctaatcta tgcggttgcg aagaattgt   1260
ggctagtgga gtagttttct gtgcttgatc ggtagattcg atgtgtgggt gtatggatgt   1320
tttctgaaaa gttgctggat tagtttacgc tttcaggccg caggtctgtt cgaaattgat   1380
tatgaagtct atatgctttg gatctatcga tttccagttt tattcagatg taggccaaaa   1440
aattgtcggc atttgtgtgg aattagttgg ccttttaggtc tgcacattca tggtgacggc   1500
acagttgctg ctggctgttg cgtgggacga gttattatag ttgttttttgt ttttccctga   1560
ttgattcaca ttttcaatga taactagcct ttgtcaccta accaagtcca ggttgatcct   1620
atctgtgttc ttcagctacc agtttgcata gatgatggtg tattcgattg ctttagtagg   1680
ccttctgatt tcacatctaa ttctgtcatg aatatagata actttacatg cttttgatat   1740
actttatatt tgaactgttc actgtccagc ctattttgga taattgagtg cattggcttt   1800
tgatgcctga attattcaca tgttcctgga taattgacct gtgtcaccta gttgactgtt   1860
ttttgaggtg ccacccgtct gttcagctga tttgtgtatt cgattgctct agttaatctt   1920
ttgattatgc agctagtgct ttgtcatatg tagctttata ggcttctgat gtccttggat   1980
atagttcagt ctacttgtca agttgcttta caagtagtag ctctgattct atttggcttc   2040
ctgagtcaga gctttgcaaa ttgcttgttg ttacattaca tcatattact tgaattgcag   2100
ttatttaatg gttggattgt tgctgtttac ttctacattt tttgctgttt tatattatac   2160
taaaatgttt gtgttgctgc ttttcagatg cagatctttg tgaagacact cactggcaag   2220
actatcaccc ttgaggtgga gtcttctgac acaattgaca atgtcaaggc aaagatccag   2280
gacaaggaag ggattcctcc agaccagcag cgccttatct tcgctggcaa gcagcttgag   2340
gatggccgta cacttgcaga ttacaacatt cagaaggagt ccacactgca ccttgtcctc   2400
aggctgcgtg gaggcatgca gattttcgtg aagaccctca ctggcaagac gatcacccta   2460
gaggtggagt catctgacac catcgacaat gtgaaggcaa agatccagga caaggagggc   2520
atcccccctg accagcagcg cctcatcttt gcaggcaagc agttggagga tgggcgaact   2580
ctggctgact ataatatcca gaaagagtcc acccttcacc tcgtcctccg cctgcgaggt   2640
ggcatgcaga tctttgtgaa gacgctgaca ggcaagacca tcacattgga agttgagtcc   2700
tccgatacaa tcgacaatgt gaaggccaag atccaggata aggagggtat cccccccggac   2760
cagcagcgcc tcatcttcgc cggcaagcag ctcgaggatg ccgcactct cgctgactac   2820
aacatccaga aggaatcaac cctgcacctg gtgctccgcc tgcgtggtgg aatgcagatc   2880
tttgtgaaga cgcttaccgg caagaccatc accttggagg tggagtcttc ggacaccatc   2940
gacaatgtga aggcgaagat tcaggacaag gagggcattc ctccggacca gcagcgcctc   3000
atctttgctg gcaagcagct agaggacggg cgtaccctgg cggattacaa catccagaag   3060
gagtccaccc tccaccttgt cctgcgcctc cgtggtggtt tctgagccta gtgctcctga   3120
```

```
gttgccttt    gtcgttatgg   tcaacctctg   gtttaagtcg   tgtgaactct   ctgcattgcg    3180
ttgctagtgt   ctggttgtgg   ttgtaataag   aacatgaaga   acatgttgct   gtggatcaca    3240
tgactttttt   ttttgaaccg   gaagatcaca   tgactttcat   ggctttaagt   tcctgaactc    3300
tgaaatctgg   acccctttt    aagctctgaa   ctcatcattc   ttgcatttac   atctggtgtt    3360
gatcttattg   atgtgatgca   gtcctgctga   aatagtcaat   gtagattcat   gactgactga    3420
ttgcgtttat   ggtgtgtatg   ttgttaacaa   gctgaaggtc   gtgtggtgtc   tttccagtta    3480
gacgaagtgt   gctttattgt   agcgtgtagt   gctgctggat   gattgatgaa   ctgaaacatt    3540
ctgcatttag   caactagcga   gccaaaggtg   atgactgagt   ttctgtagac   ctgttttttt    3600
atgcccatgg   tcgttcttca   attgcacttg   attttcacat   tagctggatc   ataatctgag    3660
cagactactc   aaaagtacaa   agttcatctt   cgctatgacg   ctttgccact   aggattttct    3720
ttgtatgatt   tgtttacaaa   tcctgtaatc   tagtcaaaag   aaaagccaaa   attttctttt    3780
gtatgatttg   tttacaaatc   ctctaatcta   gtcaaagaaa   agccaaattt   atccctcctg    3840
gtcccctaca   tcacgtagct   atgtggcccg   caagcagatg   aaagcagccc   cgtcagccga    3900
cgccgacgcc   gacgccaaca   catcctgctc   ctccctcgcc   ggcgccggcg   ccggcgaggc    3960
cgcaccgccg   ctgccccgtg   gccgcaggca   cacggtgccg   cactgccgcc   gccccgtggc    4020
cgcaggcaca   cggtgccgca   ctgccgccgc   ctccccttcc   ggcattgccg   gacggctggg    4080
ctactgtccc   cgccgccttc   ccaat                                                4105

<210> SEQ ID NO 35
<211> LENGTH: 1025
<212> TYPE: DNA
<213> ORGANISM: Panicum virgatum

<400> SEQUENCE: 35
ttgaatttta   atttcaaatt   ttgcagggta   gtagtggaca   tcacaataca   tatttagaaa      60
aagttttata   attttcctcc   gttagttttc   atataatttt   gaactccaac   gattaatcta    120
ttattaaata   tcccgatcta   tcaaaataat   gataaaaatt   tatgattaat   ttttctaaca    180
tgtgttatgg   tgtgtactat   cgtcttataa   aattcaact   taaaactcca   cctatacatg     240
gagaaatgaa   aaagacgaat   tacagtaggg   agtaatttga   accaaatgga   atagtttgag    300
ggtaaaatga   actaaacaat   agtttaggag   gttattcaga   ttttagttat   agttgagagg    360
agtaatttag   acttttttcct  atcttgaatt   gttgacggct   ctcctatcgg   atatcggatg    420
gagtctttca   gcccaacata   acttcattcg   ggcccaaacg   ttcgtccatc   cagcctaggg    480
agaacatttt   gcccatgata   tctgttttc    ttttttcta   ttttcactgg   tattataggga    540 gggaaatata   caacgtgttc   acctttggtt   tcattcttgt   tccatctgaa   tttatctaaa    600
actgtgtttg   aacttcgtaa   gaattttgtt   cgatctgtcc   ggtacatcgt   gttgataggt    660
ggcctccgag   attcttcttt   ttaaccgca   aagtaaaata   atctcagctc   cagcctaacg     720
tcaattatca   gagagagaaa   aaaatatttt   tttatgattg   atcggaaacc   aaccgcctta    780
cgtgtcgatc   ctggttcctg   gccggcacgg   cggaggaaag   cgaccgacct   cgcaacgccg    840
gcgcacggcg   ccgccgtgtt   ggacttggtc   tcccgcgact   ccgtgggcct   cggcttatcg    900
ccgccgctcc   atctcaaccg   tccgcttgga   cacgtggaag   ttgatccgtc   gcgcaccagc    960
ctcggaggta   acctaactgc   ccgtactata   aatccgggat   ccggcctctc   caatccccat   1020
cgcca                                                                        1025
```

<210> SEQ ID NO 36
<211> LENGTH: 1000
<212> TYPE: DNA
<213> ORGANISM: Panicum virgatum

<400> SEQUENCE: 36

| | | | | | |
|---|---|---|---|---|---|
| gcctagtgct | cctgagttgc | cttttgtcgt | tatggtcaac | ctctggttta | agtcgtgtga | 60 |
| actctctgca | ttgcgttgct | agtgtctggt | tgtggttgta | ataagaacat | gaagaacatg | 120 |
| ttgctgtgga | tcacatgact | tttttttttg | aaccggaaga | tcacatgact | ttcatggctt | 180 |
| taagttcctg | aactctgaaa | tctggacccc | ttttttaagct | ctgaactcat | cattcttgca | 240 |
| tttacatctg | gtgttgatct | tattgatgtg | atgcagtcct | gctgaaatag | tcaatgtaga | 300 |
| ttcatgactg | actgattgcg | tttatggtgt | gtatgttgtt | aacaagctga | aggtcgtgtg | 360 |
| gtgtctttcc | agttagacga | agtgtgcttt | attgtagcgt | gtagtgctgc | tggatgattg | 420 |
| atgaactgaa | acattctgca | tttagcaact | agcgagccaa | aggtgatgac | tgagtttctg | 480 |
| tagacctgtt | tttttatgcc | catggtcgtt | cttcaattgc | acttgatttt | cacattagct | 540 |
| ggatcataat | ctgagcagac | tactcaaaag | tacaaagttc | atcttcgcta | tgacgctttg | 600 |
| ccactaggat | tttctttgta | tgatttgttt | acaaatcctg | taatctagtc | aaagaaaag | 660 |
| ccaaaatttt | tctttgtatg | atttgtttac | aaatcctcta | atctagtcaa | agaaaagcca | 720 |
| aatttatccc | tcctggtccc | ctacatcacg | tagctatgtg | gcccgcaagc | agatgaaagc | 780 |
| agccccgtca | gccgacgccg | acgccgacgc | caacacatcc | tgctcctccc | tcgccggcgc | 840 |
| cggcgccggc | gaggccgcac | cgccgctgcc | cgtggccgc | aggcacacgg | tgccgcactg | 900 |
| ccgccgcccc | gtggccgcag | gcacacggtg | ccgcactgcc | gccgcctccc | cttccggcat | 960 |
| tgccggacgg | ctgggctact | gtccccgccg | ccttcccaat | | | 1000 |

<210> SEQ ID NO 37
<211> LENGTH: 1085
<212> TYPE: DNA
<213> ORGANISM: Panicum virgatum

<400> SEQUENCE: 37

| | | | | | |
|---|---|---|---|---|---|
| gtactcctac | ctaatcctcc | ttaactgatc | tctcctctat | cacgttggta | atcttcgaat | 60 |
| gatctgctgc | ctggctcgct | gttccccctc | gttatgcact | gtttccatca | cgagtttttt | 120 |
| ttttcatcat | ctaatctatg | cggttgcgga | agaattgtgg | ctagtggagt | agttttctgt | 180 |
| gcttgatcgg | tagattcgat | gtgtgggtgt | atggatgttt | tctgaaaagt | tgctggatta | 240 |
| gtttacgctt | tcaggccgca | ggtctgttcg | aaattgatta | tgaagtctat | atgctttgga | 300 |
| tctatcgatt | ccagttttta | ttcagatgta | ggccaaaaaa | ttgtcggcat | ttgtgtggaa | 360 |
| ttagttggcc | tttaggtctg | cacattcatg | gtgacggcac | agttgctgct | ggctgttgcg | 420 |
| tgggacgagt | tattatagtt | gttttgtttt | ttccctgatt | gattcacatt | ttcaatgata | 480 |
| actagccttt | gtcacctaac | caagtccagg | ttgatcctat | ctgtgttctt | cagctaccag | 540 |
| tttgcataga | tgatggtgta | ttcgattgct | ttagtaggcc | ttctgatttc | acatctaatt | 600 |
| ctgtcatgaa | tatagataac | tttacatgct | tttgatatac | tttatatttg | aactgttcac | 660 |
| tgtccagcct | attttggata | attgagtgca | ttggctttg | atgcctgaat | tattcacatg | 720 |
| ttcctggata | attgacctgt | gtcacctagt | tgactgtttt | ttgaggtgcc | acccgtctgt | 780 |
| tcagctgatt | tgtgtattcg | attgctctag | ttaatctttt | gattatgcag | ctagtgcttt | 840 |
| gtcatatgta | gctttatagg | cttctgatgt | ccttggatat | agttcagtct | acttgtcaag | 900 |

```
ttgctttaca agtagtagct ctgattctat ttggcttcct gagtcagagc tttgcaaatt    960
gcttgttgtt acattacatc atattacttg aattgcagtt atttaatggt tggattgttg   1020
ctgtttactt ctacatttt tgctgtttta tattatacta aaatgtttgt gttgctgctt   1080
ttcag                                                               1085

<210> SEQ ID NO 38
<211> LENGTH: 77
<212> TYPE: DNA
<213> ORGANISM: Panicum virgatum

<400> SEQUENCE: 38
caagttcgcg atctctcgat ttcacaaatc gccgagaaga cccgagcaga gaagttccct     60
ccgatcgcct tgccaag                                                   77

<210> SEQ ID NO 39
<211> LENGTH: 2187
<212> TYPE: DNA
<213> ORGANISM: Panicum virgatum

<400> SEQUENCE: 39
ttgaatttta atttcaaatt ttgcagggta gtagtggaca tcacaataca tatttagaaa     60
aagttttata attttcctcc gttagttttc atataatttt gaactccaac gattaatcta    120
ttattaaata tcccgatcta tcaaaataat gataaaaatt tatgattaat ttttctaaca    180
tgtgttatgg tgtgtactat cgtcttataa aatttcaact taaaactcca cctatacatg    240
gagaaatgaa aaagacgaat tacagtaggg agtaatttga accaaatgga atagtttgag    300
ggtaaaatga actaaacaat agtttaggag gttattcaga ttttagttat agttgagagg    360
agtaatttag actttttcct atcttgaatt gttgacggct ctcctatcgg atatcggatg    420
gagtctttca gcccaacata acttcattcg ggcccaaacg ttcgtccatc cagcctaggg    480
agaacatttt gcccatgata tctgttttc ttttttttcta ttttcactgg tattataggg    540
gggaaatata caacgtgttc accttttggt tcattcttgt tccatctgaa tttatctaaa    600
actgtgtttg aacttcgtaa gaattttgtt cgatctgtcc ggtacatcgt gttgataggt    660
ggcctccgag attcttcttt ttaaccggca aagtaaaata atctcagctc cagcctaacg    720
tcaattatca gagagagaaa aaaatatttt tttatgattg atcggaaacc aaccgcctta    780
cgtgtcgatc ctggttcctg gccggcacgg cggaggaaag cgaccgacct cgcaacgccg    840
gcgcacggcg ccgccgtgtt ggacttggtc tcccgcgact ccgtgggcct cggcttatcg    900
ccgccgctcc atctcaaccg tccgcttgga cacgtggaag ttgatccgtc gcgcaccagc    960
ctcggaggta acctaactgc ccgtactata aatccgggat ccggcctctc caatccccat   1020
cgccacaagt tcgcgatctc tcgatttcac aaatcgccga agagacccga gcagagaagt   1080
tccctccgat cgccttgcca aggtactcct acctaatcct ccttaactga tctctcctct   1140
atcacgttgg taatcttcga atgatctgct gcctggctcg ctgttccccc tcgttatgca   1200
ctgtttccat cacgagtttt ttttttcatc atctaatcta tgcggttgcg gaagaattgt   1260
ggctagtgga gtagttttct gtgcttgatc ggtagattcg atgtgtgggt gtatggatgt   1320
tttctgaaaa gttgctggat tagtttacgc tttcaggccg caggtctgtt cgaaattgat   1380
tatgaagtct atatgctttg gatctatcga tttccagttt tattcagatg taggccaaaa   1440
aattgtcggc atttgtgtgg aattagttgg cctttaggtc tgcacattca tggtgacggc   1500
```

-continued

```
acagttgctg ctggctgttg cgtgggacga gttattatag ttgttttgt ttttccctga    1560 ttgattcaca ttttcaatga taactagcct ttgtcaccta accaagtcca ggttgatcct    1620
atctgtgttc ttcagctacc agtttgcata gatgatggtg tattcgattg ctttagtagg    1680
ccttctgatt tcacatctaa ttctgtcatg aatatagata actttacatg cttttgatat    1740
actttatatt tgaactgttc actgtccagc ctattttgga taattgagtg cattggcttt    1800
tgatgcctga attattcaca tgttcctgga taattgacct gtgtcaccta gttgactgtt    1860
ttttgaggtg ccaccgtct gttcagctga tttgtgtatt cgattgctct agttaatctt    1920
ttgattatgc agctagtgct ttgtcatatg tagcttata ggcttctgat gtccttggat    1980
atagttcagt ctacttgtca agttgcttta caagtagtag ctctgattct atttggcttc    2040
ctgagtcaga gctttgcaaa ttgcttgttg ttacattaca tcatattact tgaattgcag    2100
ttatttaatg gttggattgt tgctgtttac ttctacattt tttgctgttt tatattatac    2160
taaaatgttt gtgttgctgc ttttcag                                         2187
```

<210> SEQ ID NO 40
<211> LENGTH: 711
<212> TYPE: DNA
<213> ORGANISM: Brachypodium distachyon

<400> SEQUENCE: 40

```
ggcgtcagga ctggcgaagt ctggactctg cagggccgaa ctgctgaaga cgaagcagag     60
gaagagaaag ggaagtgttc gacttgtaat ttgtaggggt ttttttttaga ggaacttgta    120 atttgtaggt gggctggcct cgttggaaaa acgatgctgg ctggttgggc tgggccgatg    180
tacgcttgca aacaacttgt ggcggcccgt tctggacgag caggagtttc ttttttgttc    240
tcacttttct ggtcttcttt agttacggag tacctttgt ttttttaaagg agttaccttt    300 tttttaggaa ttctttagtt acctttcgct tgctctcaaa aaatatttaa ctttcgcttt    360
ttttcatttt aattttttgca actatttacg agtttcatga atgcttattt tccagcatat    420
cattatttgc aagtattttt atgccgtatg tattggacga gagccatcgg gactgttcca    480
gagactgcgt ggtggggacg gctcccaacc gccttttcta tctctgttcg catccggtgg    540
ccgacttggc tcgcgcgtga gccgtgacgt aacagacttg gtctcttccc catctggcca    600
tctataaatt cccccatcga tcgaccctcc ctttccccaa tccagcaccc ccgatcccga    660
tcgaaaattc tccgcaacag caagcgatcg atctagcgaa tccccgtcaa g             711
```

CONSTRUCTS FOR EXPRESSING TRANSGENES USING REGULATORY ELEMENTS FROM BRACHYPODIUM UBIQUITIN GENES

CROSS REFERENCE TO RELATED APPLICATIONS

This application claims priority under 35 U.S.C. §119(e) of U.S. Provisional Application No. 61/872,134, filed Aug. 30, 2013, which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 63 KB ASCII (Text) file named 231402SubSeqListing.txt, created on Aug. 15, 2011 Sep. 7, 2016.

IN THE SEQUENCE LISTING

Please replace the Sequence Listing currently of record with the computer-readable form of the Substitute Sequence Listing (filename: 231402SubSeqListing.txt, created on Sep. 7, 2016) submitted herewith.

BACKGROUND

Plant transformation is an attractive technology for use in introducing agronomically desirable traits or characteristics into different crop plant species. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide resistance, enabling the production of industrially useful compounds and/or materials from the plant, and/or enabling the production of pharmaceuticals.

Transgenic plants comprising multiple transgenes stacked at a single genomic locus are produced via plant transformation technologies. Plant transformation technologies result in the introduction of transgene into a plant cell, recovery of a fertile transgenic plant that contains the stably integrated copy of the transgene in the plant genome, and subsequent transgene expression via transcription and translation of the transgene(s) results in transgenic plants that possess desirable traits and phenotypes. Each transgene in a stack typically requires an independent promoter for gene expression, and thus multiple promoters are used in a transgene stack.

The need for co-expression of multiple transgenes for regulating the same trait frequently results in the repeated use of the same promoter to drive expression of the multiple transgenes. However, the repeated use of promoters comprising sequences that share a high level of sequence identity may lead to homology-based gene silencing (HBGS). HBGS has been observed to occur frequently in transgenic plants (Peremarti et al., 2010) when repetitive DNA sequences are used within a transgene. In addition, repeated use of similar DNA sequences in transgene constructs has proven to be challenging in *Agrobacterium* due to recombination and instability of the plasmid.

Described herein are ubiquitin regulatory elements (e.g., promoters and 3'-UTR) that share low levels of sequence identity or homology with the Maize ubiquitin) promoter. Further described are constructs and methods utilizing ubiquitin regulatory elements.

SUMMARY

Disclosed herein are constructs and methods for expressing a transgene in plant cells and/or plant tissues. In one embodiment regulatory elements of a ubiquitin gene are purified from *Panicum virgatum, Brachypodium distachyon,* or *Setaria italica* genomes and recombined with sequences not natively linked to said regulatory elements to create an expression vector for expressing transgenes in plant cells not native to the ubiquitin regulatory sequences. In one embodiment an expression vector is provided wherein the regulatory elements of a ubiquitin gene are operably linked to a polylinker sequence. Such an expression vector eases the insertion of a gene or gene cassette into the vector in an operably linked state with the ubiquitin gene regulatory sequences.

In an embodiment, a construct is provided comprising a *Panicum virgatum, Brachypodium distachyon,* or *Setaria italica* ubiquitin promoter. In an embodiment, a gene expression cassette is provided comprising a *Panicum virgatum, Brachypodium distachyon* or *Setaria italica* ubiquitin promoter operably linked to a transgene. In an embodiment, a gene expression cassette includes a *Panicum virgatum, Brachypodium distachyon* or *Setaria italica* ubiquitin 5'-UTR operably linked to a transgene. In an embodiment, a gene expression cassette includes a *Panicum virgatum, Brachypodium distachyon* or *Setaria italica* ubiquitin 5'-UTR operably linked to a promoter. In an embodiment, a gene expression cassette includes a *Panicum virgatum, Brachypodium distachyon* or *Setaria italica* ubiquitin intron operably linked to a transgene. In an embodiment, a gene expression cassette includes a *Panicum virgatum, Brachypodium distachyon* or *Setaria italica* ubiquitin intron operably linked to a promoter. In an embodiment, a construct includes a gene expression cassette comprising *Panicum virgatum, Brachypodium distachyon* or *Setaria italica* ubiquitin 3'-UTR. In an embodiment, a gene expression cassette includes *Panicum virgatum, Brachypodium distachyon* or *Setaria italica* ubiquitin 3'-UTR operably linked to a transgene. In an embodiment, a gene expression cassette includes at least one, two, three, five, six, seven, eight, nine, ten, or more transgenes.

In an embodiment, a gene expression cassette includes independently a) a *Panicum virgatum, Brachypodium distachyon,* or *Setaria italica* ubiquitin promoter, b) a *Panicum virgatum, Brachypodium distachyon* or *Setaria italica* ubiquitin intron, c) a *Panicum virgatum, Brachypodium distachyon* or *Setaria italica* ubiquitin 5'-UTR, and d) a *Panicum virgatum, Brachypodium distachyon* or *Setaria italica* ubiquitin 3'-UTR.

In accordance with one embodiment a nucleic acid vector is provided comprising a promoter operably linked to a non-ubiquitin transgene, wherein the promoter consists of SEQ ID NO: 16 or a sequence having 90% sequence identity with SEQ ID NO: 16. In a further embodiment the nucleic acid vector comprises a gene cassette, wherein the gene cassette comprises a promoter, a non-ubiquitin transgene and a 3' untranslated region, wherein the promoter consists of SEQ ID NO: 16 operably linked to a first end of a transgene, wherein the second end of the transgene is operably linked to a 3' untranslated sequence consisting of SEQ ID NO: 5.

Methods of growing plants expressing a transgene using the *Panicum virgatum, Brachypodium distachyon,* or *Setaria italica* promoters, 5'-UTRs, introns, and 3'-UTRs are disclosed herein. Methods of culturing plant tissues and cells expressing a transgene using the *Panicum virgatum, Brachypodium distachyon* or *Setaria italica* promoters, 5'-UTRs, introns, and 3'-UTRs are also disclosed herein.

In accordance with one embodiment a plant, plant tissue, or plant cell is provided comprising a promoter operably linked to a non-ubiquitin transgene, wherein the promoter comprises SEQ ID NO: 2. In accordance with one embodiment a non-*Brachypodium* plant or plant cell is provided comprising SEQ ID NO: 2, or a sequence that has 90% sequence identity with SEQ ID NO: 2 operably linked to a transgene. In one embodiment the plant is a corn variety. In one embodiment a plant, plant tissue, or plant cell is provided comprising a promoter operably linked to a non-ubiquitin transgene, wherein the promoter consists of SEQ ID NO: 16 or 40. In one embodiment a non-*Brachypodium* plant or plant cell is provided comprising a gene cassette, wherein the gene cassette comprises a promoter operably linked to a transgene, further wherein the promoter consists SEQ ID NO: 16. In a further embodiment the promoter is operably linked to a first end of a transgene, wherein the second end of the transgene is operably linked to a 3' untranslated sequence consisting of SEQ ID NO: 5.

BRIEF DESCRIPTION OF THE DRAWINGS

Figure 1:
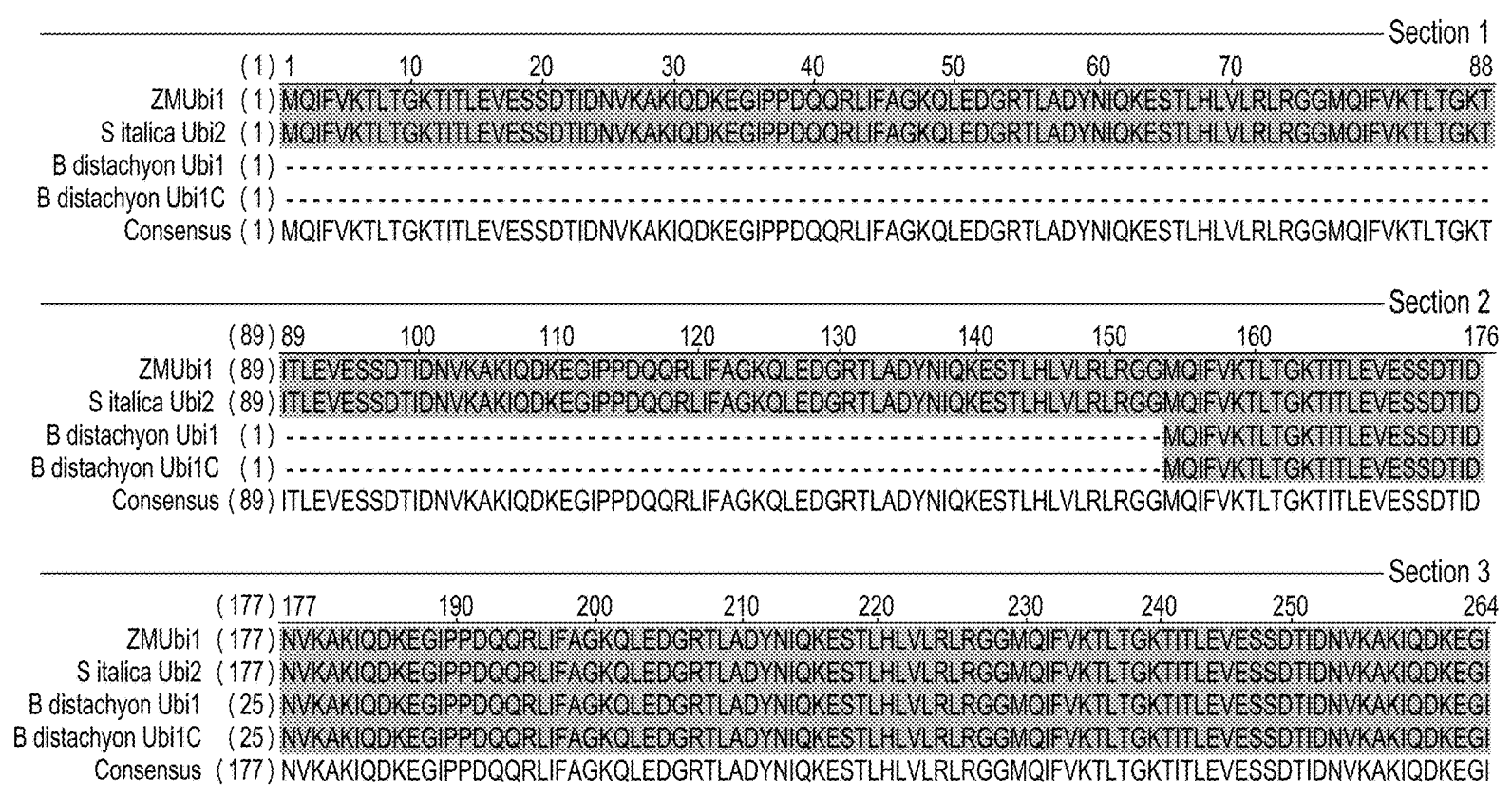
Figure 1:
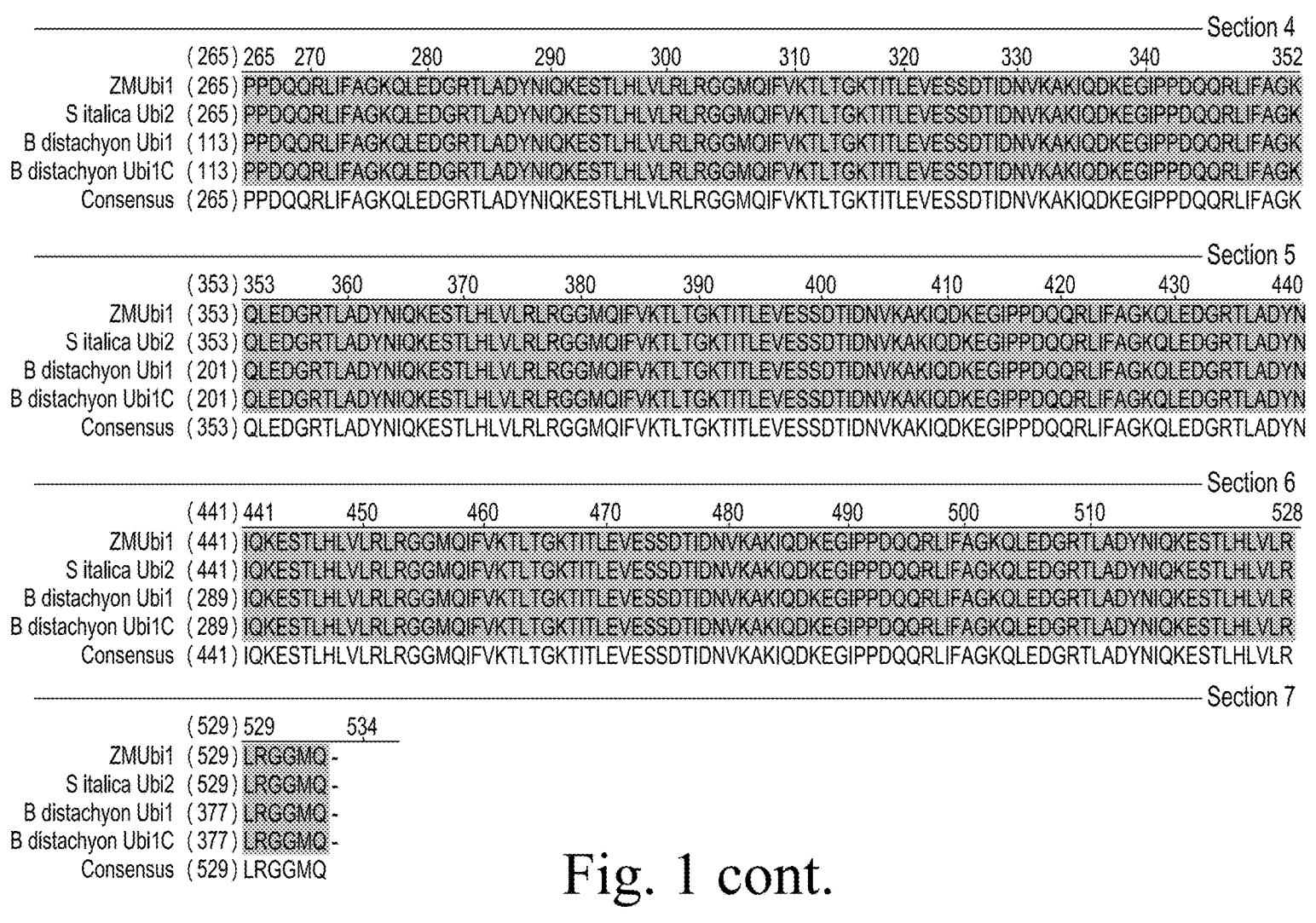

FIG. 1 shows the protein alignment of *Zea mays* ubiquitin (ZM Ubi1) protein sequence to *Brachypodium distachyon* and *Setaria italic* ubiquitin sequences used for promoter identification. The Zm Ubi1 protein sequence is disclosed herein as SEQ ID NO:22. The *S. italica* Ubi2 protein sequence is disclosed herein as SEQ ID NO:23. The *B. distachyon* Ubi1 promoter sequence is disclosed herein as SEQ ID NO:24. The *B. distachyon* Ubi1C protein sequence is disclosed herein as SEQ ID NO:25. The consensus sequence is disclosed herein as SEQ ID NO:26.

FIG. 35 presents the *Brachypodium distachyon* Ubiquitin1 C coding sequence and putative promoter (upstream sequence of ATG). The upstream promoter sequence is underlined, the 5'-UTR sequence is presented in uppercase, the intron is boxed, the Ubi1 CDS is in italics, the 3'-UTR and the transcription termination sequence is downstream of TAA (Translational Stop Codon).

FIG. 36 presents the *Brachypodium distachyon* Ubiquitin 1 coding sequence and putative promoter. The upstream promoter is underlined, the 5'UTR sequence is in uppercase, the intron is boxed, the CDS is in italics, the 3'-UTR and transcription termination sequence is downstream of TAA (Translational Stop Codon).

FIG. 37 presents the *Setaria italica* Ubiquitin2 coding sequence and putative promoter. The upstream promoter is underlined, the 5'UTR sequence is in uppercase, the intron is boxed, the CDS is in italics, the 3'-UTR and transcription termination sequence is downstream of TAA (Translational Stop Codon).

FIG. 38 presents the *Panicum virgatum* (Switchgrass) Ubiquitin 1 coding sequence and putative promoter. The upstream promoter is underlined, the 5'UTR sequence is in uppercase, the intron is boxed, the CDS is in italics, the 3'-UTR and transcription termination sequence is downstream of TAA (Translational Stop Codon).

DETAILED DESCRIPTION

Definitions

Figure 2:
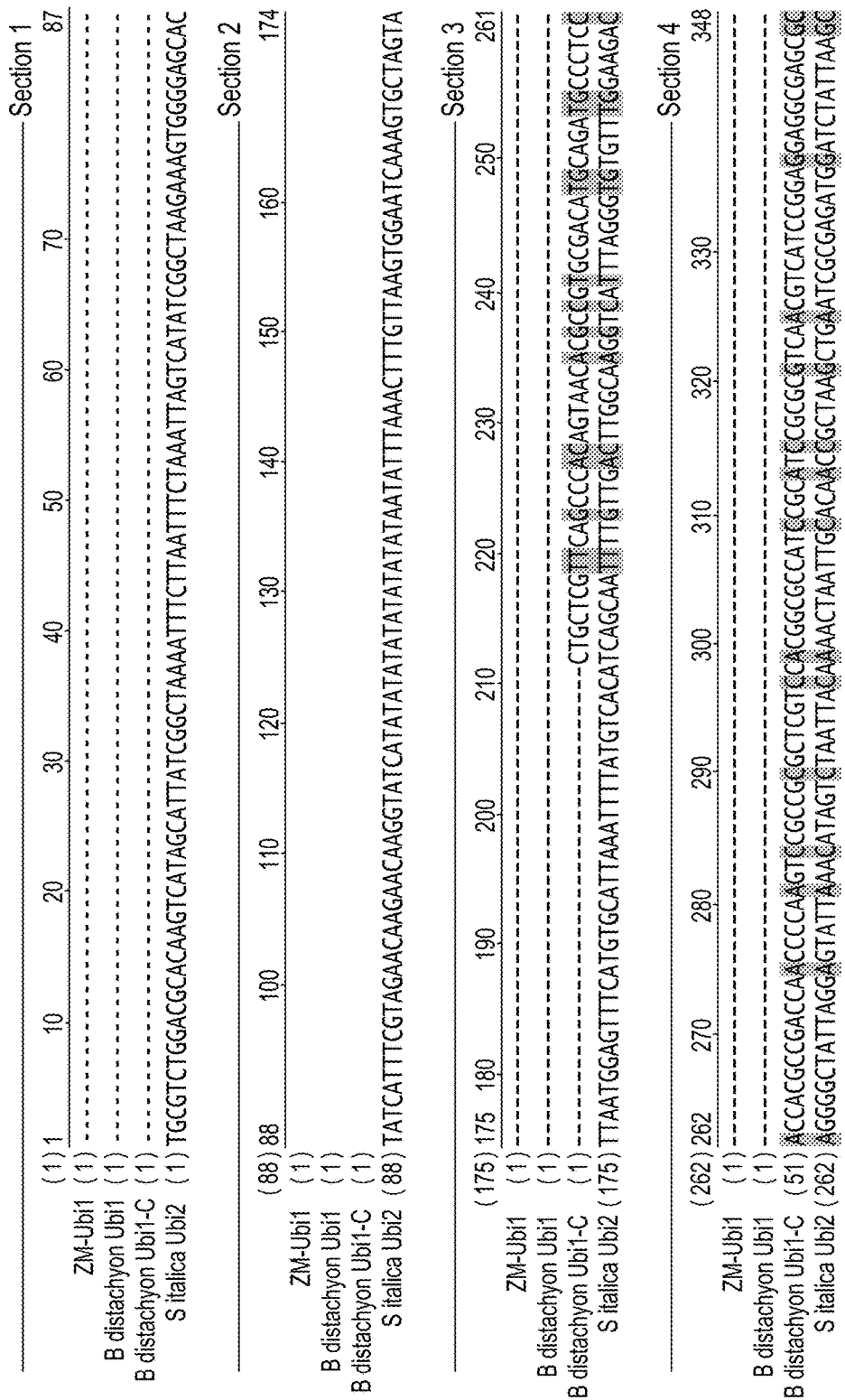
FIG. 2 shows the alignment of *Zea mays* ubiquitin (ZM Ubi1) promoter polynucleotide sequence to *Brachypodium distachyon* and *Setaria italica* ubiquitin promoter polynucleotides identified herein. The *Zea may* Ubiquitin 1 (Zm-Ubi) promoter sequence is disclosed herein as SEQ ID NO:27. The *B. distachyon* Ubi1 promoter sequence is disclosed herein as SEQ ID NO:16. The *B. distachyon* Ubi1-C promoter sequence is disclosed herein as SEQ ID NO:15. The *S. italica* Ubi2 promoter sequence is disclosed herein as SEQ ID NO:17.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "backcrossing" refers to a process in which a breeder crosses hybrid progeny back to one of the parents, for example, a first generation hybrid F1 with one of the parental genotypes of the F1 hybrid.

A "promoter" is a DNA regulatory region capable of binding RNA polymerase in a cell and initiating transcription of a downstream (3' direction) coding sequence. A promoter may contain specific sequences that are recognized by transcription factors. These factors may bind to a promoter DNA sequence, which results in the recruitment of RNA polymerase. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-ubiquitin transgene" is any transgene that has less than 80% sequence identity with the *Zea may* Ubiquitin 1 coding sequence (SEQ ID NO:27).

"Gene expression" as defined herein is the conversion of the information, contained in a gene, into a gene product.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "intron" is defined as any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains one or more transcription termination signals for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified," as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

As used herein, the terms "homology-based gene silencing" or "HBGS" are generic terms that include both transcriptional gene silencing and posttranscriptional gene silencing. Silencing of a target locus by an unlinked silencing locus can result from transcription inhibition (transcriptional gene silencing; TGS) or mRNA degradation (posttranscriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule", "nucleic acid", or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position," refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between an oligonucleotide and the DNA or RNA target. Oligonucleotides need not be 100% complementary to its target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize. In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, an oligonucleotide is typically referred to as a "primer," which allows a DNA polymerase to extend the oligonucleotide and replicate the complementary strand.

As used herein, the terms "Polymerase chain reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "sequence identity" or "identity" can be used interchangeably and refer to nucleic acid residues in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (which does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to two components that have been placed into a functional relationship with one another. The term, "operably linked," when used in reference to a regulatory sequence and a coding sequence, means that the regulatory sequence affects the expression of the linked coding sequence. "Regulatory sequences," "regulatory elements", or "control elements," refer to nucleic acid sequences that influence the timing and level/amount of transcription, RNA processing or stability, or translation of the associated coding sequence. Regulatory sequences may include promoters; translation leader sequences; 5' and 3' untranslated regions, introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. Linking can be accomplished by ligation at convenient restriction sites. If such sites do not exist, synthetic oligonucleotide adaptors or linkers are used in accordance with conventional practice. However, elements need not be contiguous to be operably linked.

As used herein, the term "transformation" encompasses all techniques by which a nucleic acid molecule can be introduced into such a cell. Examples include, but are not limited to: transfection with viral vectors; transformation with plasmid vectors; electroporation; lipofection; microinjection (Mueller et al. (1978) *Cell* 15:579-85); *Agrobacterium*-mediated transfer; direct DNA uptake; whiskers-mediated transformation; and microprojectile bombardment.

As used herein, the term "transduce" refers to a process where a virus transfers nucleic acid into a cell.

The terms "polylinker" or "multiple cloning site" as used herein defines a cluster of three or more Type-2 restriction enzyme sites located within 10 nucleotides of one another on a nucleic acid sequence. Constructs comprising a polylinker are utilized for the insertion and/or excision of nucleic acid sequences such as the coding region of a gene.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

The term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

The term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast," as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

Embodiments

As disclosed herein novel recombinant constructs are provided for expressing a non-ubiquitin transgene using the regulatory sequences of a ubiquitin gene from *Panicum virgatum*, *Brachypodium distachyon*, or *Setaria italica*. These constructs can be used to transform cells, including plant cells, to produce complete organisms that express the transgene gene product in their cells.

Regulatory Elements

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in transgenic crops to drive the expression of multiple genes.

Development of transgenic products is becoming increasingly complex, which requires stacking multiple transgenes into a single locus. Traditionally, each transgene usually requires a promoter for expression wherein multiple promoters are required to express different transgenes within one gene stack. This frequently leads to repetitive use of the same promoter within one transgene stack to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

It is desirable to use diversified promoters for the expression of different transgenes in a gene stack. In an embodiment, diversified constitutive ubiquitin obtained from different plant species can drive transcription of multiple transcription units, including RNAi, artificial miRNA, or hairpin-loop RNA sequences.

Provided are methods and constructs using a constitutive ubiquitin (Ubi1) promoter to express non-ubiquitin transgenes in plant. In an embodiment, a promoter can be the *Brachypodium distachyon* ubiquitin1 C (Ubi1C) promoter.

```
                                                (SEQ ID NO: 1)
CTGCTCGTTCAGCCCACAGTAACACGCCGTGCGACATGCAGATGCCC

TCCACCACGCCGACCAACCCCAAGTCCGCCGCGCTCGTCCACGGCGC

CATCCGCATCCGCGCGTCAACGTCATCCGGAGGAGGCGAGCGCGATG

TCGACGGCCACGGCGGCGGCGGACACGACGGCGACGCCCCGACTCC

GCGCGCGCGTCAAGGCTGCAGTGGCGTCGTGGTGGCCGTCCGCCTGC

ACGAGATCCCCGCGTGGACGAGCGCCGCCTCCACCCAGCCCCTATAT

CGAGAAATCAACGGTGGGCTCGAGCTCCTCAGCAACCTCCCCACCCC

CCCTTCCGACCACGCTCCCTTCCCCCGTGCCCCTCTTCTCCGTAAACC

CGAGCCGCCGAGAACAACACCAACGAAAGGGCGAAGAGAATCGCCA

TAGAGAGGAGATGGGCGGAGGCGGATAGTTTCAGCCATTCACGGAG

AAATGGGGAGGAGAGAACACGACATCATACGGACGCGACCCTCTAG

CTGGCTGGCTGTCCTAAAGAATCGAACGGAATCGCTGCGCCAGGAGA

AAACGAACGGTCCTGAAGCATGTGCGCCCGGTTCTTCCAAAACACTT

ATCTTTAAGATTGAAGTAGTATATATGACTGAAATTTTTACAAGGTTT

TTCCCCATAAAACAGGTGAGCTTATCTCATCCTTTTGTTTAGGATGTA

CGTATTATATATGACTGAATATTTTTTATTTTCATTGAATGAAGATTTT

CGACCCCCCAAAAATAAAAAACGGAGGGAGTACCTTTGTGCCGTGTA

TATGGACTAGAGCCATCGGGACGTTTCCGGAGACTGCGTGGTGGGGG

CGATGGACGCACAACGACCGCATTTTCGGTTGCCGACTCGCCGTTCG

CATCTGGTAGGCACGACTCGTCGGGTTCGGCTCTTGCGTGAGCCGTG

ACGTAACAGACCCGTTCTCTTCCCCCGTCTGGCCATCCATAAATCCCC

CCTCCATCGGCTTCCCTTTCCTCAATCCAGCACCCTGATT
```

In an embodiment, a promoter can be the *Brachypodium distachyon* ubiquitin 1 (Ubi1) promoter.

```
                                                (SEQ ID NO: 2)
GGCGTCAGGACTGGCGAAGTCTGGACTCTGCAGGGCCGAACTGCTGA

AGACGAAGCAGAGGAAGAGAAAGGGAAGTGTTCGACTTGTAATTTG

TAGGGGTTTTTTTAGAGGAACTTGTAATTTGTAGGTGGGCTGGCCTC

GTTGGAAAAACGATGCTGGCTGGTTGGGCTGGGCCGATGTACGCTTG

CAAACAACTTGTGGCGGCCCGTTCTGGACGAGCAGGAGTTTCTTTTTT

GTTCTCACTTTTCTGGTCTTCTTTAGTTACGGAGTACCTTTTGTTTTTT

AAAGGAGTTACCTTTTTTTAGGAATTCTTTAGTTACCTTTCGCTTGCT
```

-continued

```
CTCAAAAAATATTTAACTTTCGCTTTTTTTCATTTTAATTTTTGCAACT

ATTTACGAGTTTCATGAATGCTTATTTTCCAGCATATCATTATTTGCA

AGTATTTTTATGCCGTATGTATTGGACGAGAGCCATCGGGACTGTTCC

AGAGACTGCGTGGTGGGGACGGCTCCCAACCGCCTTTTCTATCTCTGT

TCGCATCCGGTGGCCGACTTGGCTCGCGCGTGAGCCGTGACGTAACA

GACTTGGTCTCTTCCCCATCTGGCCATCTATAAATTCCCCCATCGATC

GACCCTCCCTTTCC
```

In an embodiment, a promoter can be the *Setaria italica* ubiquitin 2 (Ubi2) promoter.

```
                                              (SEQ ID NO: 3)
TGCGTCTGGACGCACAAGTCATAGCATTATCGGCTAAAATTTCTTAAT

TTCTAAATTAGTCATATCGGCTAAGAAAGTGGGGAGCACTATCATTT

CGTAGAACAAGAACAAGGTATCATATATATATATATATAATATTT

AAACTTTGTTAAGTGGAATCAAAGTGCTAGTATTAATGGAGTTTCAT

GTGCATTAAATTTTATGTCACATCAGCAATTTTGTTGACTTGGCAAGG

TCATTTAGGGTGTGTTTGGAAGACAGGGGCTATTAGGAGTATTAAAC

ATAGTCTAATTACAAAACTAATTGCACAACCGCTAAGCTGAATCGCG

AGATGGATCTATTAAGCTTAATTAGTCCATGATTTGACAATGTGGTGC

TACAATAACCATTTGCTAATGATGGATTACTTAGGTTTAATAGATTCG

TCTCGTGATTTAGCCTATGGGTTCTGCTATTAATTTTGTAATTAGCTCA

TATTTAGTTCTTATAATTAGTATCCGAACATCCAATGTGACATGCTAA

AGTTTAACCCTGGTATCCAAATGAAGTCTTATGAGAGTTTCATCACTC

CGGTGGTATATGTACTTAGGCTCCGTTTTCTTCCACCGACTTATTTTA

GCACCCGTCACATTGAATGTTTAGATACTAATTAGAAGTATTAAACG

TAGACTATTTACAAAATCCATTACATAAGACGAATCTAAACGGCGAG

ACGAATCTATTAAACCTAATTAGTCCATGATTTGACAATGTGTTGCTA

CAGTAAACATTTGCTAATGATGGATTAATTAGGCTTAATAGATTCGTC

TCGCCGTTTAGCCTCCACTTATGTAATGGGTTTTCTAAACAATCTACG

TTTAATACTCCTAATTAGTATCTAAATATTCAATGTGACACGTGCTAA

AAATAAGTCAGTGGAAGGAAGAGAACGTCCCCTTAGTTTTCCATCTT

ATTAATTGTACGATGAAACTGTGCAGCCAGATGATTGACAATCGCAA

TACTTCAACTAGTGGGCCATGCACATCAGCGACGTGTAACGTCGTGA

GTTGCTGTTCCCGTAG
```

In an embodiment, a promoter can be the *Panicum virgatum* (Switchgrass) ubiquitin 1 promoter.

```
                                              (SEQ ID NO: 35)
TTGAATTTTAATTTCAAATTTTGCAGGGTAGTAGTGGACATCACAATA

CATATTTAGAAAAGTTTTATAATTTTCCTCCGTTAGTTTTCATATAAT

TTTGAACTCCAACGATTAATCTATTATTAAATATCCCGATCTATCAAA

ATAATGATAAAAATTTATGATTAATTTTTCTAACATGTGTTATGGTGT

GTACTATCGTCTTATAAAATTTCAACTTAAAACTCCACCTATACATGG

AGAAATGAAAAAGACGAATTACAGTAGGGAGTAATTTGAACCAAAT

GGAATAGTTTGAGGGTAAAATGAACTAAACAATAGTTTAGGAGGTTA

TTCAGATTTTAGTTATAGTTGAGAGGAGTAATTTAGACTTTTTCCTAT

CTTGAATTGTTGACGGCTCTCCTATCGGATATCGGATGGAGTCTTTCA

GCCCAACATAACTTCATTCGGGCCCAAACGTTCGTCCATCCAGCCTA

GGGAGAACATTTTGCCCATGATATCTGTTTTTCTTTTTTTCTATTTTCA

CTGGTATTATAGGAGGGAAATATACAACGTGTTCACCTTTGGTTTCAT

TCTTGTTCCATCTGAATTTATCTAAAACTGTGTTTGAACTTCGTAAGA

ATTTTGTTCGATCTGTCCGGTACATCGTGTTGATAGGTGGCCTCCGAG

ATTCTTCTTTTTAACCGGCAAAGTAAAATAATCTCAGCTCCAGCCTAA

CGTCAATTATCAGAGAGAGAAAAAAATATTTTTTATGATTGATCGG

AAACCAACCGCCTTACGTGTCGATCCTGGTTCCTGGCCGGCACGGCG

GAGGAAAGCGACCGACCTCGCAACGCCGGCGCACGGCGCCGCCGTG

TTGGACTTGGTCTCCCGCGACTCCGTGGGCCTCGGCTTATCGCCGCCG

CTCCATCTCAACCGTCCGCTTGGACACGTGGAAGTTGATCCGTCGCGC

ACCAGCCTCGGAGGTAACCTAACTGCCCGTACTATAAATCCGGGATC

CGGCCTCTCCAATCCCCATCGCCA
```

In an embodiment, a nucleic acid construct is provided comprising a ubiquitin promoter. In an embodiment, the ubiquitin promoter is a *Panicum virgatum, Brachypodium distachyon* or *Setaria italica* ubiquitin promoter. In an embodiment, a nucleic acid construct is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:35. In an embodiment, a nucleic acid construct is provided comprising a ubiquitin promoter that is operably linked to a polylinker. In an embodiment, a gene expression cassette is provided comprising a ubiquitin promoter that is operably linked to a non-ubiquitin transgene. In one embodiment the promoter consists of SEQ ID NO: 1, SEQ ID NO:2, SEQ ID NO:3, or SEQ ID NO:35. In an illustrative embodiment, a gene expression cassette comprises a ubiquitin promoter that is operably linked to the 5' end of a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In addition to a promoter, a 3'-untranslated gene region (i.e., 3'UTR) or terminator is needed for transcription termination and polyadenylation of the mRNA. Proper transcription termination and polyadenylation of mRNA is important for stable expression of transgene. The transcription termination becomes more critical for multigene stacks to avoid transcription read-through into next transgene. Similarly, non-polyadenylated aberrant RNA (aRNA) is a substrate for plant RNA-dependent RNA polymerases (RdRPs) to convert aRNA into double stranded RNA (dsRNA) leading to small RNA production and transgene silencing. Strong transcription terminators therefore are very useful both for single gene and multiple gene stacks. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene.

In accordance with one embodiment a nucleic acid construct is provided comprising a ubiquitin transcription terminator. In an embodiment, the ubiquitin transcription terminator is a *Panicum virgatum, Brachypodium distachyon* or *Setaria italica* ubiquitin transcription terminator. In an embodiment, a nucleic acid construct is provided comprising a transcription terminator, wherein the transcription terminator is at least 80%, 85%, 90%, 91%, 92%, 93%, 94%, 95%, 96%, 97%, 98%, 99%, 99.5%, 99.8%, or 100% identical to SEQ ID NO:4, SEQ ID NO:5, SEQ ID NO:6, or SEQ ID NO:36. In an embodiment, a nucleic acid construct is provided comprising a ubiquitin transcription terminator that is operably linked to a polylinker. In an embodiment, a gene expression cassette is provided comprising a ubiquitin transcription terminator that is operably linked to the 3' end of a non-ubiquitin transgene. In one embodiment the transcription terminator consists of SEQ ID NO: 4, SEQ ID NO:5, SEQ ID NO:6, or SEQ ID NO:36. In an illustrative embodiment, a gene expression cassette comprises a ubiquitin transcription terminator that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In one embodiment a nucleic acid vector is provided comprising a transcription terminator operably linked to either a polylinker sequence, a non-ubiquitin transgene or a combination of both, wherein the transcription terminator comprises SEQ ID NO: 5 or a sequence that has 90% sequence identity with SEQ ID NO: 5. In one embodiment the transcription terminator is less than 1 kb in length, and in a further embodiment the transcription terminator consists of the 3'UTR sequence of SEQ ID NO: 5.

In an embodiment, a nucleic acid construct is provided comprising a ubiquitin promoter as described herein and a 3'-UTR. In an embodiment, the nucleic acid construct comprises a ubiquitin 3'-UTR. In an embodiment, the ubiquitin 3'-UTR is a *Panicum virgatum, Brachypodium distachyon* or *Setaria italica* ubiquitin 3'-UTR. In an embodiment, a 3'-UTR can be the *Brachypodium distachyon* ubiquitin1 C (Ubi1C) 3'-UTR.

```
                                              (SEQ ID NO: 4)
GTTTGTCAAAAACTGGCCTACAGTCTGCTGCCCCTGTTGGTCTGCCCC

TTGGAAGTAGTCGTGTCTATGGTTATGTGAGAAGTCGTTGTGTTCTTT

CTAATCCCGTACTGTTTGTGTGAACATCTGCTGCTGTCGTATTGCATC

GTGAAGAATCCTGTTATGAATAAGTGAACATGAACCTTGTTCTGTGA

TTACGGCTTCGTGGTTATGCGAACGTTCTTACAAACGCAATTGCACCT

GATGTAAAATCGTTTTTGCTAGCTGTATGGAACAAGTGCTCATGATGT

TCATGCAAGATGCAATTCCAGCTTTTGTTGGTTTGTCATCTTTGTACT

GTGCTTACCGCACATAAAGATTGCATCTTGCTTATTGCTTTGTTGCTTT

GGTGCTCGTCCGCTTCTCCTTGCACCTTATCAAACCTTTGTTTAGATTC

TCTTCTTATAGCACTTGGTAACTCTCAGCTTTACAACGCCAGTACTGT

TTCTGAAATTTCATGACTGATAAAGCTGATAGATGGAGTACTAATAT

ATGACATCTTTCCATAAATGTTCGGGTGCAGAGATATGGAGGCCCCA
```

```
                                              -continued
GGATCCTATTTACAGGATGAACCTACCTGGGCCGCTGTACGCATGAC

ATCCGCGAGCAAGTCTGAGGTTCTCAATGTACACATGAAATTGATTTT

TGCTGCGTTTGGCTTGGCTGATCGTTGCATTTGTTCTGATTCATCAGA

GTTAAATAACGGATATATCAGCAAATATCCGCAGCATCCACACCGAC

CACACGTCCGGTTAACAGAGTCCCCCTGCCTTGCTTTAATTATTACGG

AGTACTCCGCTATTAATCCTTAGATATGTTTCGAAGGAACTCAAACCT

TCCTCCATCTGCAAATCTCAGTGCTTCAAAACTGGAATTAGATAATTG

AAACCTTCATTCGGTTGCAATTCACAACTGCAAATTGAACAGCACTG

TCAATTTCAATTTCGGGTTCACGATTCCACCGATAGGTTGACATGATC

CATGATCCACCCATTGTACAAC
```

In an embodiment, a 3'-UTR can be the *Brachypodium distachyon* ubiquitin 1 (Ubi1) 3'-UTR.

```
                                              (SEQ ID NO: 5)
GCTTCTGCCGAACTGGTTCACAGTCTGCTGCCCTTGGTGGTCTGCCCC

TTAGTGGTCATGCCTTTTGTTATGTGTCTTGCGTCCCAATCCTGTATCG

TTTGTGTGAACATCTCTGCTGCTGTATAGCAGCTTGAATCCTGTTATG

AATTTGTGAACCTGAACCTTGTTCCGTGAATCATGTTATGAATAAGTG

AACCTGAACCTTGTTCCGTGATTATTGTTACAATCTGTTGTGCCGTAT

GGTTGGTCGTGTGTGATTTATGTTGAACTGGAGAACCAAGTTCGTTCC

AGGACATATTGCAACCTAAGCTAAACCATGTAGAACTACTTGTTCTG

GGAGACATAAAACGTCATTTTTATGCATTCGTAACATTTAAGCATACT

ACAATAATTGTATTGTCCTTTTCCTACTCATCCTTGAAACCATATGCC

TCTTCTCAGCGCCTCTACATGCAGTGTGCTCAGAACAAACAGGCCCT

GCCAGCTGCTTTTCAATTTTCCAATTAATAACCACAATAGTCGGACTA

TGGCATCTGTGGGTGACTATGCAAGATGTTGCTGTCAGGTCTCTGAA

ACTTTTCCCATGTATCTGTTGAAATTACCCAGTAAATTCATGCCTCTA

TTTAATCTGGCATGGTTGATTTTCAAACAGAATGTGTTTTTTTTGTTC

TGGAAGCTATATTGGTAAATAAATACAAAGCTGGAGTGTGATTATAT

TTCCAACAGATATTCAAGAAAATCTCAGTTGATTTATTTACTACTGTA

GTATATATATATATCTTACAGTTGACTTCTCATATTTCAAACGACATG

TGAGCACATTGTTCAGTTTCTTAGGATGTGTTGTGTGCTCAAAGGTGT

AATTTTGCATTCTGCCCTCCGAGTAAACACTACACGTATTTTTTTGAG

TGGCAGTGCATTTGATTACAAGGCAACAACAACAAAAACCTATGGCA

AGATATCCTTCTTAGAGGCTGCCAGGATCATTTTGACTGAACTATGTA

AGGCTGAAGAAAAGG
```

In an embodiment, a 3'-UTR can be the *Setaria italica* ubiquitin 2 (Ubi2) 3'-UTR.

```
                                              (SEQ ID NO: 6)
GCCCATCGGTCATGGATGCTTCTACTGTACCTGGGTCGTCTGGTCTCT

GCCTGTGTCACCTTTGAAGTACCTGTGTCGGGATTGTGTTTGGTCATG

AACTGCAGTTTGTCTTTGATGTTCTTTTGTCTGGTCTTATGAACTGGTT
```

-continued

```
GTATCTGTATGTTTACTGTAAACTGTTGTTGCGGTGCAGCAGTATGGC

ATCCGAATGAATAAATGATGTTTGGACTTAAATCTGTACTCTGTTTGT

TTTCGGTTATGCCAGTTCTATATTGCCTGAGATCAGAATGTTTAGCTT

TTGAGTTCTGTTTGGCTTGTGGTCGACTCCTGTTTCTTACTTGAGGCGT

AACTCTGTTCTGGCAAACTCAAATGTCTAACTGAATGTTTTAGGACTT

AATTGTTGGACAGATTAACGTGTTTGGTTTGTTTCTAGATTGTGATTC

GGAAGGCTTGTTAGTTGTGGAATCAAGGAGAGCAGCTAGGTCTGTGC

AGAACGTTATTTTGGATTTAAGCCTTCTCAGATTATGCCATTACTCTA

AACCTAATGATATCATATTTCACTCGGGGATGTTGGAGTAGTCTTTTC

TTTCTCCTGCAGACAAAATGATTTTGCTTTCGTGTGTGTACATGATTTT

GTGCAACTGTTGCAACAACTGAAGTAGACAAGTTTTGACCTCACCAG

AAGAATGAAAAGATTTTGGAATTTGTTACATCGACAAACCATTGTA

ACTTGGCCCATCAGAATGCACAGAAGAGCGGCTACAAATTGACATGC

GTTGCAAACTTTGCAATAGTTGATGCACATGTTTGCCATTGCCTGCCA

GTCTTAGGAAAAGTGTGTGGTTCGAGAAATCTAAGCATATGTGCTCT

GCTCACATTGCGTGGAACCCACACAGCTTTGTCACACTCTTGTCCACT

CCAGAAGTCATTCCTGGCGCTGTTTACCCCTGGTAAAAGGTAACCGA

AAACTTCTCAAGGCTGTACCCAAAACTGGAAGGAAATTTGGAGGAAA

TCTTTGCTTTTGATCGGCTCACTCTTTC
```

In an embodiment, a 3'-UTR can be the *Panicum virgatum* (Switchgrass) ubiquitin 1 3'-UTR.

```
                                        (SEQ ID NO: 36)
GCCTAGTGCTCCTGAGTTGCCTTTTGTCGTTATGGTCAACCTCTGGTTT

AAGTCGTGTGAACTCTCTGCATTGCGTTGCTAGTGTCTGGTTGTGGTT

GTAATAAGAACATGAAGAACATGTTGCTGTGGATCACATGACTTTTT

TTTTTGAACCGGAAGATCACATGACTTTCATGGCTTTAAGTTCCTGAA

CTCTGAAATCTGGACCCCTTTTTAAGCTCTGAACTCATCATTCTTGCA

TTTACATCTGGTGTTGATCTTATTGATGTGATGCAGTCCTGCTGAAAT

AGTCAATGTAGATTCATGACTGACTGATTGCGTTTATGGTGTGTATGT

TGTTAACAAGCTGAAGGTCGTGTGGTGTCTTTCCAGTTAGACGAAGT

GTGCTTTATTGTAGCGTGTAGTGCTGCTGGATGATTGATGAACTGAAA

CATTCTGCATTTAGCAACTAGCGAGCCAAAGGTGATGACTGAGTTTC

TGTAGACCTGTTTTTTTATGCCCATGGTCGTTCTTCAATTGCACTTGAT

TTTCACATTAGCTGGATCATAATCTGAGCAGACTACTCAAAAGTACA

AAGTTCATCTTCGCTATGACGCTTTGCCACTAGGATTTTCTTTGTATG

ATTTGTTTACAAATCCTGTAATCTAGTCAAAAGAAAAGCCAAAATTTT

TCTTTGTATGATTTGTTTACAAATCCTCTAATCTAGTCAAAGAAAAGC

CAAATTTATCCCTCCTGGTCCCCTACATCACGTAGCTATGTGGCCCGC

AAGCAGATGAAAGCAGCCCCGTCAGCCGACGCCGACGCCGACGCCA

ACACATCCTGCTCCTCCCTCGCCGGCGCCGGCGCCGGCGAGGCCGCA

CCGCCGCTGCCCCGTGGCCGCAGGCACACGGTGCCGCACTGCCGCCG

CCCCGTGGCCGCAGGCACACGGTGCCGCACTGCCGCCGCCTCCCCTT

CCGGCATTGCCGGACGGCTGGGCTACTGTCCCCGCCGCCTTCCCAAT
```

In an embodiment, a nucleic acid construct is provided comprising a ubiquitin promoter as described herein and a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:4, SEQ ID NO:5, SEQ ID NO:6, or SEQ ID NO:36. In an embodiment, a nucleic acid construct is provided comprising a ubiquitin promoter as described herein and the 3'-UTR wherein the ubiquitin promoter and 3'-UTR are both operably linked to opposite ends of a polylinker. In an embodiment, a gene expression cassette is provided comprising a ubiquitin promoter as described herein and a 3'-UTR, wherein the ubiquitin promoter and 3'-UTR are both operably linked to opposite ends of a non-ubiquitin transgene. In one embodiment the a 3'-UTR, consists of SEQ ID NO:4, SEQ ID NO:5, SEQ ID NO:6, or SEQ ID NO:36. In one embodiment, a gene expression cassette is provided comprising a ubiquitin promoter as described herein and a 3'-UTR, wherein the ubiquitin promoter comprises SEQ ID NO: 2 and the 3'-UTR comprises SEQ ID NO: 5 wherein the promoter and 3'-UTR are operably linked to opposite ends of a non-ubiquitin transgene. In one embodiment the 3'-UTR, consists of SEQ ID NO:4, SEQ ID NO:5, SEQ ID NO:6, or SEQ ID NO:36. In one embodiment the promoter consists of SEQ ID NO: 2, 16 or 40 and the 3'-UTR, consists of SEQ ID NO:5. In an illustrative embodiment, a gene expression cassette comprises a ubiquitin 3'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In a further embodiment the transgene is operably linked to a ubiquitin promoter and a 3'-UTR from the same ubiquitin gene isolated from *Panicum virgatum, Brachypodium distachyon*, or *Setaria italica*.

In one embodiment a vector is provided comprising a first transgene and/or polylinker and a second transgene and/or polylinker wherein the first transgene and/or polylinker is operably linked to a promoter comprising a sequence selected from the group consisting of SEQ ID NO:1, SEQ ID NO:2, SEQ ID NO:3, and SEQ ID NO:35 and operably linked to a 3'-UTR, comprising a sequence selected from the group consisting of SEQ ID NO:4, SEQ ID NO:5, SEQ ID NO:6, or SEQ ID NO:36 and the second transgene and/or polylinker is operably linked to a promoter comprising a sequence selected from the group consisting of SEQ ID NO:1, SEQ ID NO:2, SEQ ID NO:3, and SEQ ID NO:35 and operably linked to a 3'-UTR, comprising a sequence selected from the group consisting of SEQ ID NO:4, SEQ ID NO:5, SEQ ID NO:6, or SEQ ID NO:36, further wherein the promoter of the first transgene and/or polylinker and second transgene and/or polylinker are derived from Ubi genes from different plant species. In a further embodiment the vector is provided with a third transgene and/or polylinker wherein the third transgene and/or polylinker polylinker is operably linked to a promoter comprising a sequence selected from the group consisting of SEQ ID NO:1, SEQ ID NO:2, SEQ ID NO:3, and SEQ ID NO:35 and operably linked to a 3'-UTR, comprising a sequence selected from the group consisting of SEQ ID NO:4, SEQ ID NO:5, SEQ ID NO:6, or SEQ ID NO:36, further wherein the promoter of the third transgene and/or polylinker is derived from Ubi genes from a different plant species from the promoter of the first and second transgene and/or polylinker.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene.

In an embodiment, a nucleic acid construct is provided comprising a ubiquitin promoter as described herein and an intron. In one embodiment the intron is operably linked to the 3' end of the promoter. In an embodiment, a nucleic acid construct is provided comprising a ubiquitin intron operably linked to the 3' end of a ubiquitin promoter isolated from *Panicum virgatum*, *Brachypodium distachyon* or *Setaria italica* or a derivative of such promoter sequence. In an embodiment, the ubiquitin intron is a *Panicum virgatum*, *Brachypodium distachyon* or *Setaria italica* ubiquitin intron, or a derivative of such intron sequence.

In an embodiment, an intron can be the *Brachypodium distachyon* ubiquitin1 C intron.

```
                                            (SEQ ID NO: 7)
GTATGCAGCCTCGCTTCCTCCTCGCTACCGTTTCAATTCTGGAGTAGGT

CGTAGAGGATACCATGTTGATTTGACAGAGGGAGTAGATTAGATACTTG

TAGATCGAAGTGCGGATGTTCCATGGTAGATGATACCATGTTGATTTCG

ATTAGATCGGATTAAATCTTTGTAGATCGAAGTGCGCATGTTCCATGAA

TTGCCTGTTACCAGTAGATTCAAGTTTTTCTGTGTTATAGAGGTGGGAT

CTACTCGTTGAGATGATTAGCTCCTAGAGGACACCATGCCGTTTTGGAA

AATAGATCAGAACCGTGTAGATCGATGTGAGCATGTGTTCCTGTAGATC

CAAGTTCTTTCGCATGTTACTAGTTGTGATCTATTGTTTGTGTAATACG

CTCTCGATCTATCCGTGTAGATTTCACTCGATTACTGTTACTGTGGCTT

GATCGTTCATAGTTGTTCGTTAGGTTTGATCGAACAGTGTCTGAACCTA

ATTGGATATGTATTCTTGATCTATCAACGTGTAGGTTTCAGTCATGTAT

TTATGTACTCCCTCCGTCCCAAATTAACTGACGTGGATTTTGTATAAGA

ATCTATACAAATCCATGTCAGTTAATTCGGGATGGAGTACCATATTCAA

TAATTTGTTTATTGCTGTCCACTTATGTACCATATGTTTGTTGTTCCTC

ATGTGGATTCTACTAATTATCATTGATTGGTGATCTTCTATTTTGCTAG

TTTCCTAGCTCAATCTGGTTATTCATGTAGATGTGTTGTTGAAATCGGA

GACCATGCTTGTTATTAGATAGTTTATTGCTTATCAGTTTCATGTTCTG

GTTGATGCAACACATATTCATGTTCGCTATCTGGTTGCTGCTTGATATT

CTCTGATTTACATTCATTATAAGAATATATTCTGCTCTGGTTGTTGCTT

CTCATGACTTTACCTACTCGGTAGGTGACTTACCTTTTGGTTTACAATT

GTCAACTATGCAG
```

In an embodiment, an intron can be the *Brachypodium distachyon* ubiquitin 1 (Ubi1) intron

```
                                            (SEQ ID NO: 8)
GTATGTAGCCTCTCGATTCCTCCTCAGCCCTGCCCTCGATTTGGTGTAC

GCGTTGAGATGATGATCTCGTAGATGTCTAGATGACACCATGTCGATTT

GAAATAGATCAGATCCGTGTAGATCGATGAGCTCCTGTGTACCTGTGGA

TTCAAGTTATTTTCGCATGCTATTGTTGTGATCTACTAGATCTAGTGTG

TGTATTCTATGCTATCGATTTCTCCGTGTAGATTTCACTCGATTACTGT

TACTGTGGCTTGATCGGCCATAGATGTTGGTTAAGGTTTGATCGGTTAG

TGTTTGAACCTGCGTGGATATCTAGCATCCATCTATTATCGTGTAGGTT

TCGAACAAACAAGCACTATTATTGTACTGATGGTTCGTCTATGGTTGGT

TTTGACCGTTTTAGTGTTGAACGAGCCTTCTGTATTTGTTTATTGCTGT

CCAGTGATGTACCATGTTCGTTGAGTGTCGGATTATACTAATTATTGTT

GATTGATAATCTTGTAGTTTGCTTTTCCTAATTTATTTATCGTAGTCCT

GATTTGCCTCAGCTGTGCCTCACCCGTGCGATGGTCAATCAACTTGTTA

GCCCAATCTGCTTAATCATGTACATTTGTTGTTAGAATCAGAGATCAAG

CCAATTAGCTATCTTATTGCTTATCTGTTCCATGTTCTGATCGATGTAA

CAGTCTACACTTTTGCTCTGTGCTACTTGATTAAAACATTCTGACTTAA

ATTCATGATTGGAAGTTTCAGATCTGATTGTTGCCTTACTTGACTAATA

TCTATTCATGTGACACCTCTCTGTCTTGGTAACTTACCGCTGTTTGTTT

GTAATTTCTGACTATGCAG
```

In an embodiment, an intron can be the *Setaria italica* ubiquitin 2 (Ubi2) intron 1

```
                                            (SEQ ID NO: 9)
GTCACGGGTTCCTTCCCCACCTCTCCTCTTCCCCACCGCCATAAATAG
```

In an embodiment, an intron can be the *Setaria italica* ubiquitin 2 (Ubi2) intron 2

```
                                            (SEQ ID NO: 10)
GTACGGCGATCGTCTTCCTCCTCTAGATCGGCGTGATCTGCAAGTAGTT

GATTTGGTAGATGGTTAGGATCTGTGCACTGAAGAAATCATGTTAGATC

CGCGATGTTTCTGTTCGTAGATGGCTGGGAGGTGGAATTTTTGTGTAGA

TCTGATATGTTCTCCTGTTTATCTTGTCACGCTCCTGCGATTTGTGGGG

ATTTTAGGTCGTTGATCTGGGAATCGTGGGGTTGCTTCTAGGCTGTTCG

TAGATGAGGTCGTTCTCACGGTTTACTGGATCATTGCCTAGTAGATCAG

CTCGGGCTTTCGTCTTTGTATATGGTGCCCATACTTGCATCTATGATCT

GGTTCCGTGGTGTTACCTAGGTTTCTGCGCCTGATTCGTCCGATCGATT

TTGTTAGCATGTGGTAAACGTTTGGTCATGGTCTGATTTAGATTAGAGT

CGAATAGGATGATCTCGATCTAGCTCTTGGGATTAATATGCATGTGTCA

CCAATCTGTTCCGTGGTTAAGATGATGAATCTATGCTTAGTTAATGGGT

GTAGATATATATGCTGCTGTTCCTCAATGATGCCGTAGCTTTTACCTGA

GCAGCATGGATCCTCCTGTTACTTAGGTAGATGCACATGCTTATAGATC

AAGATATGTACTGCTACTGTTGGAATTCTTTAGTATACCTGATGATCAT

CCATGCTCTTGTTACTTGTTTTGGTATACTTGGATGATGGCATGCTGCT

GCTTTTTGTTGATTTGAGCCCATCCATATCTGCATATGTCACATGATTA

AGATGATTACGCTGTTTCTGTATGATGCCATAGCTTTTATGTGAGCAAC
```

-continued
```
ATGCATCCTCCTGGTTATATGCATTAATAGATGGAAGATATCTATTGCT

ACAATTTGATGATTATTTTGTACATACGATGATCAAGCATGCTCTTCAT

ACTTTGTTGATATACTTGGATAATGAAATGCTGCTGCACGTTCATTCTA

TAGCACTAATGATGTGATGAACACGCACGACCTGTTTGTGGCATCTGTT

TGAATGTGTTGTTGCTGTTCACTAGAGACTGTTTTATTAACCTACTGCT

AGATACTTACCCTTCTGTCTGTTTATTCTTTTGCAG
```

In an embodiment, an intron can be the *Panicum virgatum* (Switchgrass) ubiquitin intron.

```
                                          (SEQ ID NO: 37)
GTACTCCTACCTAATCCTCCTTAACTGATCTCTCCTCTATCACGTTGGT

AATCTTCGAATGATCTGCTGCCTGGCTCGCTGTTCCCCCTCGTTATGCA

CTGTTTCCATCACGAGTTTTTTTTTCATCATCTAATCTATGCGGTTGC

GGAAGAATTGTGGCTAGTGGAGTAGTTTTCTGTGCTTGATCGGTAGATT

CGATGTGTGGGTGTATGGATGTTTTCTGAAAAGTTGCTGGATTAGTTTA

CGCTTTCAGGCCGCAGGTCTGTTCGAAATTGATTATGAAGTCTATATGC

TTTGGATCTATCGATTTCCAGTTTTATTCAGATGTAGGCCAAAAAATTG

TCGGCATTTGTGTGGAATTAGTTGGCCTTTAGGTCTGCACATTCATGGT

GACGGCACAGTTGCTGCTGGCTGTTGCGTGGGACGAGTTATTATAGTTG

TTTTTGTTTTTCCCTGATTGATTCACATTTTCAATGATAACTAGCCTTT

GTCACCTAACCAAGTCCAGGTTGATCCTATCTGTGTTCTTCAGCTACCA

GTTTGCATAGATGATGGTGTATTCGATTGCTTTAGTAGGCCTTCTGATT

TCACATCTAATTCTGTCATGAATATAGATAACTTTACATGCTTTTGATA

TACTTTATATTTGAACTGTTCACTGTCCAGCCTATTTTGGATAATTGAG

TGCATTGGCTTTTGATGCCTGAATTATTCACATGTTCCTGGATAATTGA

CCTGTGTCACCTAGTTGACTGTTTTTTGAGGTGCCACCCGTCTGTTCAG

CTGATTTGTGTATTCGATTGCTCTAGTTAATCTTTTGATTATGCAGCTA

GTGCTTTGTCATATGTAGCTTTATAGGCTTCTGATGTCCTTGGATATAG

TTCAGTCTACTTGTCAAGTTGCTTTACAAGTAGTAGCTCTGATTCTATT

TGGCTTCCTGAGTCAGAGCTTTGCAAATTGCTTGTTGTTACATTACATC

ATATTACTTGAATTGCAGTTATTTAATGGTTGGATTGTTGCTGTTTACT

TCTACATTTTTTGCTGTTTTATATTATACTAAAATGTTTGTGTTGCTGC

TTTTCAG
```

In an embodiment, a nucleic acid construct is provided comprising a ubiquitin promoter as described herein and an intron, wherein the intron is at least 80%, 85%, 90%, 91%, 92%, 93%, 94%, 95%, 96%, 97%, 98%, 99%, 99.5%, 99.8%, or 100% identical to SEQ ID NO:7, SEQ ID NO:8, SEQ ID NO:9, SEQ ID NO:10, or SEQ ID NO:37. In an embodiment, a nucleic acid construct is provided comprising a ubiquitin promoter as described herein, an intron sequence and a polylinker wherein the promoter and intron are operably linked to a polylinker. In an embodiment, a gene expression cassette is provided comprising a ubiquitin promoter as described herein, an intron sequence and a non-ubiquitin transgene wherein the promoter and intron are operably linked to the 5' end of the transgene. Optionally the construct further comprises a 3'-UTR that is operably linked to the 3' end of the non-ubiquitin transgene or polylinker. In one embodiment the promoter and 3'-UTR sequences are selected from those described herein and the intron sequence consists of SEQ ID NO:7, SEQ ID NO:8, SEQ ID NO:9, SEQ ID NO:10, or SEQ ID NO:37. In an embodiment, a gene expression cassette comprises a ubiquitin intron that is operably linked to a promoter, wherein the promoter is a *Panicum virgatum*, *Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a ubiquitin intron that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

Transgene expression may also be regulated by a 5'-UTR region located downstream of the promoter sequence. Both a promoter and a 5'-UTR can regulate transgene expression. While a promoter is necessary to drive transcription, the presence of a 5'-UTR can increase expression levels resulting in mRNA transcript for translation and protein synthesis. A 5'-UTR gene region aids stable expression of a transgene.

In an embodiment, a nucleic acid construct is provided comprising a ubiquitin promoter as described herein and a 5'-UTR. In one embodiment the 5'-UTR is operably linked to the 3' end of the promoter. In an embodiment, a nucleic acid construct is provided comprising a ubiquitin a 5'-UTR operably linked to the 3' end of a ubiquitin promoter isolated from *Panicum virgatum*, *Brachypodium distachyon* or *Setaria italica* or a derivative of such promoter sequence. In a further embodiment the 3' end of the 5'-UTR is operably linked to the 5' end of a ubiquitin intron from *Panicum virgatum*, *Brachypodium distachyon* or *Setaria italica*, as described herein.

```
In an embodiment, a 5'-UTR can be the
Brachypodium distachyon ubiquitin1 C (Ubi1C)
5'-UTR.
                                        (SEQ ID NO: 11)
CCGATCGAAAAGTCCCCGCAAGAGCAAGCGACCGATCTCGTGAATCTCC
GTCAAG In an embodiment, a 5'-UTR can be the
Brachypodium distachyon ubiquitin 1 (Ubi1) 5'-
UTR.
                                        (SEQ ID NO: 12)
CCAATCCAGCACCCCCGATCCCGATCGAAAATTCTCCGCAACAGCAAGC
GATCGATCTAGCGAATCCCCGTCAAG In an embodiment, a 5'-UTR can be the Setaria
italica ubiquitin 2 (Ubi2) 5'-UTR1
                                        (SEQ ID NO: 13)
AGAAATATCAACTGGTGGGCCACGCACATCAGCGTCGTGTAACGTGGAC
GGAGGAGCCCCGTGACGGCGTCGACATCGAACGGCCACCAACCACGGAA
CCACCCGTCCCCACCTCTCGGAAGCTCCGCTCCACGGCGTCGACATCTA
ACGGCTACCAGCAGGCGTACGGGTTGGAGTGGACTCCTTGCCTCTTTGC
GCTGGCGGCTTCCGGAAATTGCGTGGCGGAGACGAGGCGGGCTCGTCTC
ACACGGCACGGAAGAC In an embodiment, a 5'-UTR can be the Setaria
italica ubiquitin 2 (Ubi2) 5'-UTR2
                                        (SEQ ID NO: 14)
CCGACCCCCTCGCCTTTCTCCCCAATCTCATCTCGTCTCGTGTTGTTCG
GAGCACACCACCCGCCCCAAATCGTTCTTCCCGCAAGCCTCGGCGATCC
TTCACCCGCTTCAAG
```

-continued

In an embodiment, a 5'-UTR can be the *Panicum virgatum* (Switchgrass) ubiquitin 5'-UTR.

(SEQ ID NO: 38)
CAAGTTCGCGATCTCTCGATTTCACAAATCGCCGAGAAGACCCGAGCAG
AGAAGTTCCCTCCGATCGCCTTGCCAAG.

In an embodiment, a nucleic acid construct is provided comprising a ubiquitin promoter as disclosed herein and a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:11, SEQ ID NO:12, SEQ ID NO:13, SEQ ID NO:14, or SEQ ID NO:38. In an embodiment, a nucleic acid construct is provided comprising ubiquitin promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:35, and a 5'-UTR operably linked to a polylinker. In an embodiment, a gene expression cassette is provided comprising a ubiquitin promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:35, and a 5'-UTR sequences operably linked to a non-ubiquitin transgene. Optionally, the construct can further comprise a ubiquitin intron as disclosed herein operably linked to the 3' end of the 5'-UTR and the 5' end of the non-ubiquitin transgene and optionally further comprising a 3'-UTR that is operably linked to the 3' end of the non-ubiquitin transgene. In one embodiment the promoter, intron and 3'-UTR sequences are selected from those described herein and the 5'-UTR sequence consists of SEQ ID NO:11, SEQ ID NO:12, SEQ ID NO:13, SEQ ID NO:14, or SEQ ID NO:38. In one embodiment the 3'-UTR consists of SEQ ID NO:12.

In an embodiment, a gene expression cassette comprises a ubiquitin 5'-UTR that is operably linked to a promoter, wherein the promoter is a *Panicum virgatum, Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a ubiquitin 5'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In one embodiment a nucleic acid construct is provided comprising a promoter and a polylinker and optionally one or more of the following elements:
  a) a 5' untranslated region;
  b) an intron; and
  c) a 3' untranslated region,
wherein
  the promoter consists of SEQ ID NO:1, SEQ ID NO:2, SEQ ID NO:3, or SEQ ID NO:35 or a sequence having 98% sequence identity with SEQ ID NO:1, SEQ ID NO:2, SEQ ID NO:3, or SEQ ID NO:35;
  the 5' untranslated region consists of SEQ ID NO:11, SEQ ID NO:12, SEQ ID NO:13, SEQ ID NO:14, or SEQ ID NO:38 or a sequence having 98% sequence identity with SEQ ID NO:11, SEQ ID NO:12, SEQ ID NO:13, SEQ ID NO:14, or SEQ ID NO:38
  the intron consists of SEQ ID NO:7, SEQ ID NO:8, SEQ ID NO:9, SEQ ID NO:10, or SEQ ID NO:37 or a sequence having 98% sequence identity with SEQ ID NO:7, SEQ ID NO:8, SEQ ID NO:9, SEQ ID NO:10, or SEQ ID NO:37
  the 3' untranslated region consists of SEQ ID NO:4, SEQ ID NO:5, SEQ ID NO:6, or SEQ ID NO:36 or a sequence having 98% sequence identity with SEQ ID NO:4, SEQ ID NO:5, SEQ ID NO:6, or SEQ ID NO:36; further wherein said promoter is operably linked to said polylinker and each optional element, when present, is also operably linked to both the promoter and the polylinker.

In one embodiment a nucleic acid construct is provided comprising a promoter and a non-ubiquitin transgene and optionally one or more of the following elements:
  a) a 5' untranslated region;
  b) an intron; and
  c) a 3' untranslated region,
wherein
  the promoter consists of SEQ ID NO:1, SEQ ID NO:2, SEQ ID NO:3, or SEQ ID NO:35 or a sequence having 98% sequence identity with SEQ ID NO:1, SEQ ID NO:2, SEQ ID NO:3, or SEQ ID NO:35;
  the 5' untranslated region consists of SEQ ID NO:11, SEQ ID NO:12, SEQ ID NO:13, SEQ ID NO:14, or SEQ ID NO:38 or a sequence having 98% sequence identity with SEQ ID NO:11, SEQ ID NO:12, SEQ ID NO:13, SEQ ID NO:14, or SEQ ID NO:38
  the intron consists of SEQ ID NO:7, SEQ ID NO:8, SEQ ID NO:9, SEQ ID NO:10, or SEQ ID NO:37 or a sequence having 98% sequence identity with SEQ ID NO:7, SEQ ID NO:8, SEQ ID NO:9, SEQ ID NO:10, or SEQ ID NO:37
  the 3' untranslated region consists of SEQ ID NO:4, SEQ ID NO:5, SEQ ID NO:6, or SEQ ID NO:36 or a sequence having 98% sequence identity with SEQ ID NO:4, SEQ ID NO:5, SEQ ID NO:6, or SEQ ID NO:36; further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In accordance with one embodiment transgene expression is regulated by a promoter operably linked to an intron and 5'-UTR region, wherein the intron and 5'-UTR region are located downstream of the promoter sequence. A promoter operably linked to an intron and 5'-UTR region can be used to drive transgene expression. While a promoter is necessary to drive transcription, the presence of the intron and 5'-UTR can increase expression levels resulting in mRNA transcript for translation and protein synthesis.

In an embodiment, a gene expression cassette comprises a promoter operably linked to a 5'-UTR and intron region. In an embodiment, a gene expression cassette comprises a ubiquitin promoter operably linked to a ubiquitin 5'-UTR and ubiquitin intron. In an embodiment, the ubiquitin promoter operably linked to a 5'-UTR and intron region is a *Panicum virgatum, Brachypodium distachyon* or *Setaria italica* ubiquitin promoter operably linked to an intron and 5'-UTR.

In an embodiment, a promoter operably linked to a 5'-UTR and intron can be the *Brachypodium distachyon* ubiquitin1 C (Ubi1C) promoter operably linked to an intron and 5'-UTR. In one embodiment the promoter comprises or consists of SEQ ID NO: 15:

(SEQ ID NO: 15)
```
CTGCTCGTTCAGCCCACAGTAACACGCCGTGCGACATGCAGATGCCCTC
CACCACGCCGACCAACCCCAAGTCCGCCGCGCTCGTCCACGGCGCCATC
CGCATCCGCGCGTCAACGTCATCCGGAGGAGGCGAGCGCGATGTCGACG
GCCACGGCGGCGGCGGACACGACGGCGACGCCCCGACTCCGCGCGCGCG
TCAAGGCTGCAGTGGCGTCGTGGTGGCCGTCCGCCTGCACGAGATCCCC
GCGTGGACGAGCGCCGCCTCCACCCAGCCCCTATATCGAGAAATCAACG
GTGGGCTCGAGCTCCTCAGCAACCTCCCCACCCCCCTTCCGACCACGC
TCCCTTCCCCCGTGCCCCTCTTCTCCGTAAACCCGAGCCGCCGAGAACA
ACACCAACGAAAGGGCGAAGAGAATCGCCATAGAGAGGAGATGGGCGGA
GGCGGATAGTTTCAGCCATTCACGGAGAAATGGGGAGGAGAGAACACGA
CATCATACGGACGCGACCCTCTAGCTGGCTGGCTGTCCTAAAGAATCGA
ACGGAATCGCTGCGCCAGGAGAAAACGAACGGTCCTGAAGCATGTGCGC
CCGGTTCTTCCAAAACACTTATCTTTAAGATTGAAGTAGTATATATGAC
TGAAATTTTTACAAGGTTTTTCCCCATAAAACAGGTGAGCTTATCTCAT
CCTTTTGTTTAGGATGTACGTATTATATATGACTGAATATTTTTTATTT
TCATTGAATGAAGATTTTCGACCCCCCAAAAATAAAAAACGGAGGGAGT
ACCTTTGTGCCGTGTATATGGACTAGAGCCATCGGGACGTTTCCGGAGA
CTGCGTGGTGGGGCGATGGACGCACAACGACCGCATTTTCGGTTGCCG
ACTCGCCGTTCGCATCTGGTAGGCACGACTCGTCGGGTTCGGCTCTTGC
GTGAGCCGTGACGTAACAGACCCGTTCTCTTCCCCGTCGGCCATCCA
TAAATCCCCCCTCCATCGGCTTCCCTTTCCTCAATCCAGCACCCTGATT
CCGATCGAAAAGTCCCCGCAAGAGCAAGCGACCGATCTCGTGAATCTCC
GTCAAGGTATGCAGCCTCGCTTCCTCCTCGCTACCGTTTCAATTCTGGA
GTAGGTCGTAGAGGATACCATGTTGATTTGACAGAGGGAGTAGATTAGA
TACTTGTAGATCGAAGTGCGGATGTTCCATGGTAGATGATACCATGTTG
ATTTCGATTAGATCGGATTAAATCTTTGTAGATCGAAGTGCGCATGTTC
CATGAATTGCCTGTTACCAGTAGATTCAAGTTTTTCTGTGTTATAGAGG
TGGGATCTACTCGTTGAGATGATTAGCTCCTAGAGGACACCATGCCGTT
TTGGAAAATAGATCAGAACCGTGTAGATCGATGTGAGCATGTGTTCCTG
TAGATCCAAGTTCTTTCGCATGTTACTAGTTGTGATCTATTGTTTGTGT
AATACGCTCTCGATCTATCCGTGTAGATTTCACTCGATTACTGTTACTG
TGGCTTGATCGTTCATAGTTGTTCGTTAGGTTTGATCGAACAGTGTCTG
AACCTAATTGGATATGTATTCTTGATCTATCAACGTGTAGGTTTCAGTC
ATGTATTTATGTACTCCCTCCGTCCCAAATTAACTGACGTGGATTTTGT
ATAAGAATCTATACAAATCCATGTCAGTTAATTCGGGATGGAGTACCAT
ATTCAATAATTTGTTTATTGCTGTCCACTTATGTACCATATGTTTGTTG
TTCCTCATGTGGATTCTACTAATTATCATTGATTGGTGATCTTCTATTT
TGCTAGTTTCCTAGCTCAATCTGGTTATTCATGTAGATGTGTTGTTGAA
ATCGGAGACCATGCTTGTTATTAGATAGTTTATTGCTTATCAGTTTCAT
GTTCTGGTTGATGCAACACATATTCATGTTCGCTATCTGGTTGCTGCTT
GATATTCTCTGATTTACATTCATTATAAGAATATATTCTGCTCTGGTTG
TTGCTTCTCATGACTTTACCTACTCGGTAGGTGACTTACCTTTTGGTTT
ACAATTGTCAACTATGCAG
```

In an embodiment, a promoter operably linked to 5'-UTR and intron can be the *Brachypodium distachyon* ubiquitin 1 (Ubi1) promoter operably linked to a 5'-UTR and intron. In one embodiment the promoter comprises or consists of SEQ ID NO: 16:

(SEQ ID NO: 16)
```
GGCGTCAGGACTGGCGAAGTCTGGACTCTGCAGGGCCGAACTGCTGAAG
ACGAAGCAGAGGAAGAGAAAGGGAAGTGTTCGACTTGTAATTTGTAGGG
GTTTTTTTAGAGGAACTTGTAATTTGTAGGTGGGCTGGCCTCGTTGGA
AAAACGATGCTGGCTGGTTGGGCTGGGCCGATGTACGCTTGCAAACAAC
TTGTGGCGGCCCGTTCTGGACGAGCAGGAGTTTCTTTTTTGTTCTCACT
TTTCTGGTCTTCTTTAGTTACGGAGTACCTTTTGTTTTTTAAAGGAGTT
ACCTTTTTTTTAGGAATTCTTTAGTTACCTTTCGCTTGCTCTCAAAAAA
TATTTAACTTTCGCTTTTTTTCATTTTAATTTTTGCAACTATTTACGAG
TTTCATGAATGCTTATTTTCCAGCATATCATTATTTGCAAGTATTTTTA
TGCCGTATGTATTGGACGAGAGCCATCGGGACTGTTCCAGAGACTGCGT
GGTGGGACGGCTCCCAACCGCCTTTTCTATCTCTGTTCGCATCCGGTG
GCCGACTTGGCTCGCGCGTGAGCCGTGACGTAACAGACTTGGTCTCTTC
CCCATCTGGCCATCTATAAATTCCCCCATCGATCGACCCTCCCTTTCCC
CAATCCAGCACCCCCGATCCCGATCGAAAATTCTCCGCAACAGCAAGCG
ATCGATCTAGCGAATCCCCGTCAAGGTATGTAGCCTCTCGATTCCTCCT
CAGCCCTGCCCTCGATTTGGTGTACGCGTTGAGATGATGATCTCGTAGA
TGTCTAGATGACACCATGTCGATTTGAAATAGATCAGATCCGTGTAGAT
CGATGAGCTCCTGTGTACCTGTGGATTCAAGTTATTTTCGCATGCTATT
GTTGTGATCTACTAGATCTAGTGTGTGTATTCTATGCTATCGATTTCTC
CGTGTAGATTTCACTCGATTACTGTTACTGTGGCTTGATCGGCCATAGA
TGTTGGTTAAGGTTTGATCGGTTAGTGTTTGAACCTGCGTGGATATCTA
GCATCCATCTATTATCGTGTAGGTTTCGAACAAACAAGCACTATTATTG
TACTGATGGTTCGTCTATGGTTGGTTTTGACCGTTTTAGTGTTGAACGA
GCCTTCTGTATTTGTTTATTGCTGTCCAGTGATGTACCATGTTCGTTGA
GTGTCGGATTATACTAATTATTGTTGATTGATAATCTTGTAGTTTGCTT
TTCCTAATTTATTTATCGTAGTCCTGATTTGCCTCAGCTGTGCCTCACC
CGTGCGATGGTCAATCAACTTGTTAGCCCAATCTGCTTAATCATGTACA
TTTGTTGTTAGAATCAGAGATCAAGCCAATTAGCTATCTTATTGCTTAT
CTGTTCCATGTTCTGATCGATGTAACAGTCTACACTTTTGCTCTGTGCT
ACTTGATTAAAACATTCTGACTTAAATTCATGATTGGAAGTTTCAGATC
TGATTGTTGCCTTACTTGACTAATATCTATTCATGTGACACCTCTCTGT
CTTGGTAACTTACCGCTGTTTGTTTGTAATTTCTGACTATGCAG
```

In an embodiment, a promoter operably linked to a 5'-UTR and intron can be the *Setaria italica* ubiquitin 2 (Ubi2)

promoter operably linked to a 5'-UTR and intron. In one embodiment the promoter comprises or consists of SEQ ID NO: 17:

(SEQ ID NO: 17)
TGCGTCTGGACGCACAAGTCATAGCATTATCGGCTAAAATTTCTTAATT

TCTAAATTAGTCATATCGGCTAAGAAAGTGGGGAGCACTATCATTTCGT

AGAACAAGAACAAGGTATCATATATATATATATATATAATATTTAAACT

TTGTTAAGTGGAATCAAAGTGCTAGTATTAATGGAGTTTCATGTGCATT

AAATTTTATGTCACATCAGCAATTTTGTTGACTTGGCAAGGTCATTTAG

GGTGTGTTTGGAAGACAGGGGCTATTAGGAGTATTAAACATAGTCTAAT

TACAAAACTAATTGCACAACCGCTAAGCTGAATCGCGAGATGGATCTAT

TAAGCTTAATTAGTCCATGATTTGACAATGTGGTGCTACAATAACCATT

TGCTAATGATGGATTACTTAGGTTTAATAGATTCGTCTCGTGATTTAGC

CTATGGGTTCTGCTATTAATTTTGTAATTAGCTCATATTTAGTTCTTAT

AATTAGTATCCGAACATCCAATGTGACATGCTAAAGTTTAACCCTGGTA

TCCAAATGAAGTCTTATGAGAGTTTCATCACTCCGGTGGTATATGTACT

TAGGCTCCGTTTTCTTCCACCGACTTATTTTTAGCACCCGTCACATTGA

ATGTTTAGATACTAATTAGAAGTATTAAACGTAGACTATTTACAAAATC

CATTACATAAGACGAATCTAAACGGCGAGACGAATCTATTAAACCTAAT

TAGTCCATGATTTGACAATGTGTTGCTACAGTAAACATTTGCTAATGAT

GGATTAATTAGGCTTAATAGATTCGTCTCGCCGTTTAGCCTCCACTTAT

GTAATGGGTTTTCTAAACAATCTACGTTTAATACTCCTAATTAGTATCT

AAATATTCAATGTGACACGTGCTAAAAATAAGTCAGTGGAAGGAAGAGA

ACGTCCCCTTAGTTTTCCATCTTATTAATTGTACGATGAAACTGTGCAG

CCAGATGATTGACAATCGCAATACTTCAACTAGTGGGCCATGCACATCA

GCGACGTGTAACGTCGTGAGTTGCTGTTCCCGTAGAGAAATATCAACTG

GTGGGCCACGCACATCAGCGTCGTGTAACGTGGACGGAGGAGCCCCGTG

ACGGCGTCGACATCGAACGGCCACCAACCACGGAACCACCCGTCCCCAC

CTCTCGGAAGCTCCGCTCCACGGCGTCGACATCTAACGGCTACCAGCAG

GCGTACGGGTTGGAGTGGACTCCTTGCCTCTTTGCGCTGGCGGCTTCCG

GAAATTGCGTGGCGGAGACGAGGCGGGCTCGTCTCACACGGCACGGAAG

ACGTCACGGGTTCCTTCCCCACCTCTCCTCTTCCCCACCGCCATAAATA

GCCGACCCCCTCGCCTTTCTCCCCAATCTCATCTCGTCTCGTGTTGTTC

GGAGCACACCACCCGCCCCAAATCGTTCTTCCCGCAAGCCTCGGCGATC

CTTCACCCGCTTCAAGGTACGGCGATCGTCTTCCTCCTCTAGATCGGCG

TGATCTGCAAGTAGTTGATTTGGTAGATGGTTAGGATCTGTGCACTGAA

GAAATCATGTTAGATCCGCGATGTTTCTGTTCGTAGATGGCTGGGAGGT

GGAATTTTGTGTAGATCTGATATGTTCTCCTGTTTATCTTGTCACGCT

CCTGCGATTTGTGGGGATTTTAGGTCGTTGATCTGGGAATCGTGGGGTT

GCTTCTAGGCTGTTCGTAGATGAGGTCGTTCTCACGGTTTACTGGATCA

TTGCCTAGTAGATCAGCTCGGGCTTTCGTCTTTGTATATGGTGCCCATA

CTTGCATCTATGATCTGGTTCCGTGGTGTTACCTAGGTTTCTGCGCCTG

ATTCGTCCGATCGATTTTGTTAGCATGTGGTAAACGTTTGGTCATGGTC

TGATTTAGATTAGAGTCGAATAGGATGATCTCGATCTAGCTCTTGGGAT

TAATATGCATGTGTCACCAATCTGTTCCGTGGTTAAGATGATGAATCTA

TGCTTAGTTAATGGGTGTAGATATATATGCTGCTGTTCCTCAATGATGC

CGTAGCTTTTACCTGAGCAGCATGGATCCTCCTGTTACTTAGGTAGATG

CACATGCTTATAGATCAAGATATGTACTGCTACTGTTGGAATTCTTTAG

TATACCTGATGATCATCCATGCTCTTGTTACTTGTTTTGGTATACTTGG

ATGATGGCATGCTGCTGCTTTTTGTTGATTTGAGCCCATCCATATCTGC

ATATGTCACATGATTAAGATGATTACGCTGTTTCTGTATGATGCCATAG

CTTTTATGTGAGCAACATGCATCCTCCTGGTTATATGCATTAATAGATG

GAAGATATCTATTGCTACAATTTGATGATTATTTTGTACATACGATGAT

CAAGCATGCTCTTCATACTTTGTTGATATACTTGGATAATGAAATGCTG

CTGCACGTTCATTCTATAGCACTAATGATGTGATGAACACGCACGACCT

GTTTGTGGCATCTGTTTGAATGTGTTGTTGCTGTTCACTAGAGACTGTT

TTATTAACCTACTGCTAGATACTTACCCTTCTGTCTGTTTATTCTTTTG

CAG

In an embodiment, a promoter operably linked to a 5'-UTR and intron can be the *Panicum virgatum* (Switchgrass) ubiquitin promoter operably linked to a 5'-UTR and intron. In one embodiment the promoter comprises or consists of SEQ ID NO: 39:

(SEQ ID NO: 39)
TTGAATTTTAATTTCAAATTTTGCAGGGTAGTAGTGGACATCACAATAC

ATATTTAGAAAAGTTTTATAATTTTCCTCCGTTAGTTTTCATATAATT

TTGAACTCCAACGATTAATCTATTATTAAATATCCCGATCTATCAAAAT

AATGATAAAAATTTATGATTAATTTTTCTAACATGTGTTATGGTGTGTA

CTATCGTCTTATAAAATTTCAACTTAAAACTCCACCTATACATGGAGAA

ATGAAAAAGACGAATTACAGTAGGGAGTAATTTGAACCAAATGGAATAG

TTTGAGGGTAAAATGAACTAAACAATAGTTTAGGAGGTTATTCAGATTT

TAGTTATAGTTGAGAGGAGTAATTTAGACTTTTTCCTATCTTGAATTGT

TGACGGCTCTCCTATCGGATATCGGATGGAGTCTTTCAGCCCAACATAA

CTTCATTCGGGCCCAAACGTTCGTCCATCCAGCCTAGGGAGAACATTTT

GCCCATGATATCTGTTTTTCTTTTTTTCTATTTTCACTGGTATTATAGG

AGGGAAATATACAACGTGTTCACCTTTGGTTTCATTCTTGTTCCATCTG

AATTTATCTAAAACTGTGTTTGAACTTCGTAAGAATTTTGTTCGATCTG

TCCGGTACATCGTGTTGATAGGTGGCCTCCGAGATTCTTCTTTTTAACC

GGCAAAGTAAAATAATCTCAGCTCCAGCCTAACGTCAATTATCAGAGAG

AGAAAAAAATATTTTTTATGATTGATCGGAAACCAACCGCCTTACGTG

TCGATCCTGGTTCCTGGCCGGCACGGCGGAGGAAAGCGACCGACCTCGC

AACGCCGGCGCACGGCGCCGCCGTGTTGGACTTGGTCTCCCGCGACTCC

GTGGGCCTCGGCTTATCGCCGCCGCTCCATCTCAACCGTCCGCTTGGAC

-continued
```
ACGTGGAAGTTGATCCGTCGCGCACCAGCCTCGGAGGTAACCTAACTGC

CCGTACTATAAATCCGGGATCCGGCCTCTCCAATCCCCATCGCCACAAG

TTCGCGATCTCTCGATTTCACAAATCGCCGAGAAGACCCGAGCAGAGAA

GTTCCCTCCGATCGCCTTGCCAAGGTACTCCTACCTAATCCTCCTTAAC

TGATCTCTCCTCTATCACGTTGGTAATCTTCGAATGATCTGCTGCCTGG

CTCGCTGTTCCCCCTCGTTATGCACTGTTTCCATCACGAGTTTTTTTTT

TCATCATCTAATCTATGCGGTTGCGGAAGAATTGTGGCTAGTGGAGTAG

TTTTCTGTGCTTGATCGGTAGATTCGATGTGTGGGTGTATGGATGTTTT

CTGAAAAGTTGCTGGATTAGTTTACGCTTTCAGGCCGCAGGTCTGTTCG

AAATTGATTATGAAGTCTATATGCTTTGGATCTATCGATTTCCAGTTTT

ATTCAGATGTAGGCCAAAAAATTGTCGGCATTTGTGTGGAATTAGTTGG

CCTTTAGGTCTGCACATTCATGGTGACGGCACAGTTGCTGCTGGCTGTT

GCGTGGGACGAGTTATTATAGTTGTTTTTGTTTTTCCCTGATTGATTCA

CATTTTCAATGATAACTAGCCTTTGTCACCTAACCAAGTCCAGGTTGAT

CCTATCTGTGTTCTTCAGCTACCAGTTTGCATAGATGATGGTGTATTCG

ATTGCTTTAGTAGGCCTTCTGATTTCACATCTAATTCTGTCATGAATAT

AGATAACTTTACATGCTTTTGATATACTTTATATTTGAACTGTTCACTG

TCCAGCCTATTTTGGATAATTGAGTGCATTGGCTTTTGATGCCTGAATT

ATTCACATGTTCCTGGATAATTGACCTGTGTCACCTAGTTGACTGTTTT

TTGAGGTGCCACCCGTCTGTTCAGCTGATTTGTGTATTCGATTGCTCTA

GTTAATCTTTTGATTATGCAGCTAGTGCTTTGTCATATGTAGCTTTATA

GGCTTCTGATGTCCTTGGATATAGTTCAGTCTACTTGTCAAGTTGCTTT

ACAAGTAGTAGCTCTGATTCTATTTGGCTTCCTGAGTCAGAGCTTTGCA

AATTGCTTGTTGTTACATTACATCATATTACTTGAATTGCAGTTATTTA

ATGGTTGGATTGTTGCTGTTTACTTCTACATTTTTTGCTGTTTTATATT

ATACTAAAATGTTTGTGTTGCTGCTTTTCAG
```

In an embodiment, a nucleic acid construct is provided comprising a promoter operably linked to an intron and 5'-UTR. In one embodiment the construct comprises at least 80%, 85%, 90%, 91%, 92%, 93%, 94%, 95%, 96%, 97%, 98%, 99%, 99.5%, 99.8%, or 100% identical to SEQ ID NO:15, SEQ ID NO:16, SEQ ID NO:17, or SEQ ID NO:39. In one embodiment, a nucleic acid construct is provided comprising a ubiquitin promoter sequence comprising or consisting of a sequence at least 80%, 85%, 90%, 91%, 92%, 93%, 94%, 95%, 96%, 97%, 98%, 99%, 99.5%, 99.8%, or 100% identical to SEQ ID NO:15, SEQ ID NO:16, SEQ ID NO:17, or SEQ ID NO:39 operably linked to a polylinker. Optionally, the construct can further comprise 3'-UTR that is operably linked to the 3' end of the polylinker. In an embodiment, a gene expression cassette is provided comprising a ubiquitin promoter sequence wherein the promoter sequence comprises or consists of a sequence at least 80%, 85%, 90%, 91%, 92%, 93%, 94%, 95%, 96%, 97%, 98%, 99%, 99.5%, 99.8%, or 100% identical to SEQ ID NO:15, SEQ ID NO:16, SEQ ID NO:17, or SEQ ID NO:39. operably linked to a non-ubiquitin transgene. Optionally, the construct can further comprise 3'-UTR that is operably linked to the 3' end of the non-ubiquitin transgene. In one embodiment the 3'-UTR sequence consists of SEQ ID NO:4, SEQ ID NO:5, SEQ ID NO:6, or SEQ ID NO:36. In an illustrative embodiment, the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In one embodiment the transgene is an herbicide resistance gene. In one embodiment a vector is provided comprising 1, 2, 3 or 4 promoter sequences independently selected from the group consisting of SEQ ID NO:4, SEQ ID NO:5, SEQ ID NO:6, or SEQ ID NO:36.

In an embodiment, a gene expression cassette comprises a ubiquitin promoter, a ubiquitin 5'-UTR, a ubiquitin intron, and a ubiquitin 3'-UTR. In an embodiment, a ubiquitin promoter, a ubiquitin 5'-UTR, a ubiquitin intron, and a ubiquitin 3'-UTR can each be independently a *Panicum virgatum*, *Brachypodium distachyon* or *Setaria italica* ubiquitin promoter; *Panicum virgatum Brachypodium distachyon* or *Setaria italica* ubiquitin 5'-UTR; *Panicum virgatum*, *Brachypodium distachyon* or *Setaria italica* ubiquitin intron; and, a *Panicum virgatum*, *Brachypodium distachyon* or *Setaria italica* ubiquitin 3'-UTR. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:36; b) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:4, SEQ ID NO:5, SEQ ID NO:6, or SEQ ID NO:37; c) a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:11, SEQ ID NO:12, SEQ ID NO:13, SEQ ID NO:14, or SEQ ID NO:38; or, d) an intron, wherein the intron is at least 80%, 85%, 90%, 91%, 92%, 93%, 94%, 95%, 96%, 97%, 98%, 99%, 99.5%, 99.8%, or 100% identical to SEQ ID NO:15, SEQ ID NO:16, SEQ ID NO:17, or SEQ ID NO:39.

For example, a gene expression cassette may include both a promoter, an intron, and a 5'-UTR wherein the promoter is a polynucleotide of SEQ ID NO:2, the intron is a polynucleotide of SEQ ID NO:8, and the 5'-UTR is a polynucleotide of SEQ ID NO:12. Likewise, a gene expression cassette may include both a promoter, an intron, and a 5'-UTR wherein the promoter is a polynucleotide of SEQ ID NO:2, the intron is a polynucleotide of SEQ ID NO:8, and the 5'-UTR is a polynucleotide of SEQ ID NO:12. Furthermore, a gene expression cassette may include both a promoter, an intron, and a 5'-UTR wherein the promoter is a polynucleotide of SEQ ID NO:3, the intron is a polynucleotide of SEQ ID NO:9 and/or SEQ ID NO:10, and the 5'-UTR is a polynucleotide of SEQ ID NO:13. In addition, a gene expression cassette may include both a promoter, an intron, and a 5'-UTR wherein the promoter is a polynucleotide of SEQ ID NO:35, the intron is a polynucleotide of SEQ ID NO:37, and the 5'-UTR is a polynucleotide of SEQ ID NO:38.

For example, a gene expression cassette may include both a promoter, an intron, a 5'-UTR, and a 3'-UTR wherein the promoter is a polynucleotide of SEQ ID NO:2, the intron is a polynucleotide of SEQ ID NO:8, the 5'-UTR is a polynucleotide of SEQ ID NO:12, and the 3'-UTR is a polynucleotide of SEQ ID No:5. Likewise, a gene expression cassette may include both a promoter, an intron, a 5'-UTR, and a 3'-UTR wherein the promoter is a polynucleotide of SEQ ID NO:2, the intron is a polynucleotide of SEQ ID NO:8, the 5'-UTR is a polynucleotide of SEQ ID NO:12, and the 3'-UTR is a polynucleotide of SEQ ID NO:5. Furthermore, a gene expression cassette may include both a promoter, an intron, a 5'-UTR, and a 3'-UTR wherein the promoter is a polynucleotide of SEQ ID NO:3, the intron is a polynucleotide of SEQ ID NO:9 and/or SEQ ID NO:10, the 5'-UTR is a polynucleotide of SEQ ID NO:13 or 14, and the 3'-UTR is a polynucleotide of SEQ ID NO:6. In addition, a gene expression cassette may include both a promoter, an intron, a 5'-UTR, and a 3'-UTR wherein the promoter is a polynucleotide of SEQ ID NO:35, the intron is a polynucleotide of SEQ ID NO:37, the 5'-UTR is a polynucleotide of SEQ ID NO:38, and the 3'-UTR is a polynucleotide of SEQ ID NO:36.

In addition, a gene expression cassette may include both a promoter, and a 3'-UTR wherein the promoter is a polynucleotide of SEQ ID NO:2 and a 3'-UTR of SEQ ID NO:6. In an embodiment, a gene expression cassette may include both a promoter and a 3'-UTR wherein the promoter is a polynucleotide of SEQ ID NO:2 and a 3'-UTR of SEQ ID NO:5. In an embodiment, a gene expression cassette may include both a promoter and a 3'-UTR wherein the promoter is a polynucleotide of SEQ ID NO:2 and a 3'-UTR of SEQ ID NO:5. In an embodiment, a gene expression cassette may include both a promoter and a 3'-UTR wherein the promoter is a polynucleotide of SEQ ID NO:35 and a 3'-UTR of SEQ ID NO:36.

In an embodiment, a gene expression cassette comprises a ubiquitin promoter, ubiquitin 5'-UTR, and a ubiquitin 3'-UTR that are operably linked to a non-ubiquitin transgene. In an embodiment, a gene expression cassette comprises a ubiquitin promoter, a ubiquitin intron, ubiquitin 5'-UTR, and a ubiquitin 3'-UTR that are operably linked to a non-ubiquitin transgene.

A promoter, an intron, a 5'-UTR, and 3'-UTR can be operably linked to different transgenes within a gene expression cassette when a gene expression cassette includes one or more transgenes. In an illustrative embodiment, a gene expression cassette comprises a ubiquitin promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a ubiquitin promoter, an intron, and a 5'-UTR that are operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a ubiquitin 3'-UTR that is operably linked to a transgene, wherein the transgene encodes for a gene product that enhances insecticidal resistance, herbicide tolerance, nitrogen use efficiency, water us efficiency, nutritional quality or combinations thereof.

A ubiquitin intron and a 5'-UTR can be operably linked to different promoters within a gene expression cassette. In an illustrative embodiment, the promoters originate from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a ubiquitin promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

In accordance with one embodiment a nucleic acid vector is provided comprising a recombinant gene cassette wherein the recombinant gene cassette comprises a ubiquitin based promoter operably linked to a polylinker sequence, a non-ubiquitin transgene or combination thereof. In one embodiment the recombinant gene cassette comprises a ubiquitin based promoter operably linked to a non-ubiquitin transgene. In one embodiment the recombinant gene cassette comprises a ubiquitin based promoter as disclosed herein operably linked to a polylinker sequence. The polylinker is operably linked to the ubiquitin based promoter in a manner such that insertion of a coding sequence into one of the restriction sites of the polylinker will operably link the coding sequence allowing for expression of the coding sequence when the vector is transfected into a host cell.

In accordance with one embodiment the ubiquitin based promoter comprises SEQ ID NO: 2 or a sequence that has 90, 95 or 99% sequence identity with SEQ ID NO: 2. In accordance with one embodiment the promoter sequence has a total length of no more than 1.5, 2, 2.5, 3 or 4 kb. In accordance with one embodiment the ubiquitin based promoter consists of SEQ ID NO: 2 or a 636 bp sequence that has 90, 95 or 99% sequence identity with SEQ ID NO: 2.

In accordance with one embodiment a nucleic acid vector is provided comprising a gene cassette that consists of SEQ ID NO: 16, a non-ubiquitin transgene and a 3'-UTR, wherein SEQ ID NO: 16 is operably linked to the 5' end of the non-ubiquitin transgene and the 3'-UTR is operably linked to the 3' end of the non-ubiquitin transgene. In a further embodiment the 3' untranslated sequence comprises SEQ ID NO: 5 or a sequence that has 90, 95, 99 or 100% sequence identity with SEQ ID NO: 5. In accordance with one embodiment a nucleic acid vector is provided comprising a gene cassette that consists of SEQ ID NO: 16, or a 1563 bp sequence that has 90, 95, or 99% sequence identity with SEQ ID NO: 16, a non-ubiquitin transgene and a 3'-UTR, wherein SEQ ID NO: 16 is operably linked to the 5' end of the non-ubiquitin transgene and the 3'-UTR is operably linked to the 3' end of the non-ubiquitin transgene. In a further embodiment the 3' untranslated sequence comprises SEQ ID NO: 5 or a sequence that has 90, 95, 99 or 100% sequence identity with SEQ ID NO: 5. I a further embodiment the 3' untranslated sequence consists of SEQ ID NO: 5, or a 1020 bp sequence that has 90, 95, or 99% sequence identity with SEQ ID NO: 5.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein first T-DNA border is operably linked to one end of the gene construct, and said second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacte-*

*rium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO: 2, SEQ ID NO: 16 or a sequence having 90, 95, or 99% sequence identity with SEQ ID NO: 2 or SEQ ID NO: 16.

Transgenes of interest and suitable for use in the present disclosed constructs include, but are not limited to, coding sequences that confer (1) resistance to pests or disease, (2) resistance to herbicides, and (3) value added traits as disclosed in WO2013116700 (DGT-28), US20110107455 (DSM-2), U.S. Pat. No. 8,283,522 (AAD-12); U.S. Pat. No. 7,838,733 (AAD-1); U.S. Pat. Nos. 5,188,960; 5,691,308; 6,096,708; and 6,573,240 (Cry1F); U.S. Pat. Nos. 6,114,138; 5,710,020; and 6,251,656 (Cry1Ac); U.S. Pat. Nos. 6,127,180; 6,624,145 and 6,340,593 (Cry34Ab1); U.S. Pat. Nos. 6,083,499; 6,548,291 and 6,340,593 (Cry35Ab1), the disclosures of which are incorporated herein. In accordance with one embodiment the transgene encodes a selectable marker or a gene product conferring insecticidal resistance, herbicide tolerance, nitrogen use efficiency, water use efficiency, or nutritional quality.

In accordance with one embodiment a nucleic acid vector is provided comprising a gene cassette wherein the gene cassette comprises a promoter region operably linked to the 5' end of a transgene wherein the 3' end of the transgene is linked to a 3' untranslated region. In one embodiment the promoter region comprises SEQ ID NO: 2 or a sequence that has 90, 95 or 99% sequence identity with SEQ ID NO: 2. In accordance with one embodiment the promoter region consists of SEQ ID NO: 2 or SEQ ID NO: 16. In one embodiment the 3' untranslated sequence comprises SEQ ID NO: 5 or a sequence that has 90, 95 or 99% sequence identity with SEQ ID NO: 5, and in one embodiment the 3' untranslated sequence consists of SEQ ID NO: 5 or a 1020 bp sequence having 90, 95 or 99% sequence identity with SEQ ID NO: 5.

In accordance with one embodiment a nucleic acid vector is provided comprising a gene cassette wherein the gene cassette comprises a promoter region operably linked to the 5' end of a 5' untranslated sequence, wherein the 3' end of the 5' untranslated sequence is operably linked to the 5' end of the transgene wherein the 3' end of the transgene is linked to a 3' untranslated region. In one embodiment the promoter region comprises or consists of SEQ ID NO: 2 or a sequence that has 90, 95 or 99% sequence identity with SEQ ID NO: 2. In one embodiment the promoter region consists of SEQ ID NO: 2 or a 636 bp sequence that has 90, 95 or 99% sequence identity with SEQ ID NO: 2. In accordance with one embodiment the 5' untranslated sequence comprises or consists of SEQ ID NO: 12 or a sequence that has 90% sequence identity with SEQ ID NO: 12. In accordance with one embodiment the 5' untranslated sequence consists of SEQ ID NO: 12 or a 75 bp sequence that has 90% sequence identity with SEQ ID NO: 12. In one embodiment the 3' untranslated sequence comprises or consists of SEQ ID NO: 5 or a sequence that has 90, 95 or 99% sequence identity with SEQ ID NO: 5. In one embodiment the 3' untranslated sequence consists of SEQ ID NO: 5 or a 1020 bp sequence that has 90, 95 or 99% sequence identity with SEQ ID NO: 5. In a further embodiment the nucleic acid vector further comprises a ubiquitin intron inserted between the 5' untranslated region and the transgene, and operably linked to the promoter and transgene. In one embodiment the ubiquitin intron comprises or consists of SEQ ID NO: 8 or a sequence that has 90, 95 or 99% sequence identity with SEQ ID NO: 8. In one embodiment the ubiquitin intron consists of SEQ ID NO: 8 or a 852 bp sequence that has 90, 95 or 99% sequence identity with SEQ ID NO: 8.

In accordance with one embodiment a nucleic acid vector is provided comprising a gene cassette wherein the gene cassette comprises a promoter region operably linked to the 5' end of a transgene wherein the 3' end of the transgene is linked to a 3' untranslated region. In one embodiment the promoter region comprises SEQ ID NO: 40 or a sequence that has 90, 95 or 99% sequence identity with SEQ ID NO: 40.

```
                                                 (SEQ ID NO: 40)
GGCGTCAGGACTGGCGAAGTCTGGACTCTGCAGGGCCGAACTGCTGAAG

ACGAAGCAGAGGAAGAGAAAGGGAAGTGTTCGACTTGTAATTTGTAGGG

GTTTTTTTTAGAGGAACTTGTAATTTGTAGGTGGGCTGGCCTCGTTGGA

AAAACGATGCTGGCTGGTTGGGCTGGGCCGATGTACGCTTGCAAACAAC

TTGTGGCGGCCCGTTCTGGACGAGCAGGAGTTTCTTTTTTGTTCTCACT

TTTCTGGTCTTCTTTAGTTACGGAGTACCTTTTGTTTTTTAAAGGAGTT

ACCTTTTTTTAGGAATTCTTTAGTTACCTTTCGCTTGCTCTCAAAAAA

TATTTAACTTTCGCTTTTTTTCATTTTAATTTTTGCAACTATTTACGAG

TTTCATGAATGCTTATTTTCCAGCATATCATTATTTGCAAGTATTTTTA

TGCCGTATGTATTGGACGAGAGCCATCGGGACTGTTCCAGAGACTGCGT

GGTGGGGACGGCTCCCAACCGCCTTTTCTATCTCTGTTCGCATCCGGTG

GCCGACTTGGCTCGCGCGTGAGCCGTGACGTAACAGACTTGGTCTCTTC

CCCATCTGGCCATCTATAAATTCCCCCATCGATCGACCCTCCCTTTCCC

CAATCCAGCACCCCCGATCCCGATCGAAAATTCTCCGCAACAGCAAGCG

ATCGATCTAGCGAATCCCCGTCAAG
```

In accordance with one embodiment the promoter region consists of SEQ ID NO: 40 or a 711 bp sequence having 90, 95 or 99% sequence identity with SEQ ID NO: 40. In accordance with one embodiment the promoter region consists of SEQ ID NO: 40. In one embodiment the 3' untranslated sequence consists of SEQ ID NO: 5 or a 1020 bp sequence that has 90, 95 or 99% sequence identity with SEQ ID NO: 5, and in one embodiment the 3' untranslated sequence consists of SEQ ID NO: 5.

In an embodiment, a cell or plant is provided comprising a gene expression cassette as disclosed herein. In an embodiment, a cell or plant comprises a vector comprising a gene expression cassette as disclosed herein. In an embodiment, a vector can be a plasmid, a cosmid, a bacterial artificial chromosome (BAC), a bacteriophage, or a virus. Thereby, a cell or plant comprising a gene expression cassette as disclosed herein is a transgenic cell or transgenic plant, respectively. In an embodiment, a transgenic plant can be a monocotyledonous plant. In an embodiment, a transgenic monocotyledonous plant can be, but is not limited to maize, wheat, rice, sorghum, oats, rye, bananas, sugar cane, and millet. In an embodiment, a transgenic plant can be a dicotyledonous plant. In an embodiment, a transgenic dicotyledonous plant can be, but is not limited to soybean, cotton, sunflower, and canola. An embodiment also includes a transgenic seed from a transgenic plant as disclosed herein.

In an embodiment, a gene expression cassette includes two or more transgenes. The two or more transgenes may not be operably linked to the same promoter, intron, or 5'-UTR or 3'-UTR as disclosed herein. In an embodiment, a gene expression cassette includes one or more transgenes. In an embodiment with one or more transgenes, at least one transgene is operably linked to a promoter, intron, 5'-UTR, or 3'-UTR or the subject disclosure.

Selectable Markers

Various selectable markers also described as reporter genes can be incorporated into a chosen expression vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1, or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from Streptomyces species, including Streptomyces hygroscopicus and Streptomyces viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)—Accl-S1, Accl-S2 and Accl-S3. In an embodiment, herbicides can inhibit photosynthesis, including triazine (psbA and 1s+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. No. 6,166,302, and U.S. Pat. No. 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); Agrobacterium-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-Agrobacterium bacteria or viruses such as Rhizobium sp. NGR234, Sinorhizoboium meliloti, Mesorhizobium loti, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming Brassica plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and northern blotting and PCR; biochemical assays, such as detecting the presence of a protein product, e.g., by immunological means (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a ubiquitin promoter operably linked to at least one transgene. In an embodiment, a method of expressing at least one transgene in a plant comprising growing a plant comprising a ubiquitin 5'-UTR operably linked to at least one transgene. In an embodiment, a method of expressing at least one transgene in a plant comprising growing a plant comprising a ubiquitin intron operably linked to at least one transgene. In an embodiment, a method of expressing at least one transgene in a plant comprising growing a plant comprising a ubiquitin promoter, a ubiquitin 5'-UTR, and a ubiquitin intron operably linked to at least one transgene. In an embodiment, a method of expressing at least one transgene in a plant comprising growing a plant comprising a ubiquitin 3'-UTR operably linked to at least one transgene. In an embodiment, a method of expressing at least one transgene in a plant tissue or plant cell comprising culturing a plant tissue or plant cell comprising a ubiquitin promoter operably linked to at least one transgene. In an embodiment, a method of expressing at least one transgene in a plant tissue or plant cell comprising culturing a plant tissue or plant cell comprising a ubiquitin 5'-UTR operably linked to at least one transgene. In an embodiment, a method of expressing at least one transgene in a plant tissue or plant cell comprising culturing a plant tissue or plant cell comprising a ubiquitin intron operably linked to at least one transgene. In an embodiment, a method of expressing at least one transgene in a plant tissue or plant cell comprising culturing a plant tissue or plant cell comprising a ubiquitin promoter, a ubiquitin 5'-UTR, and a ubiquitin intron operably linked to at least one transgene. In an embodiment, a method of expressing at least one transgene in a plant tissue or plant cell comprising culturing a plant tissue or plant cell comprising a ubiquitin 3'-UTR operably linked to at least one transgene.

In an embodiment, a method of expressing at least one transgene in a plant comprises growing a plant comprising a gene expression cassette comprising a ubiquitin promoter operably linked to at least one transgene. In one embodiment the ubiquitin promoter consists of a sequence selected from SEQ ID NO:1, SEQ ID NO:2, SEQ ID NO:3, SEQ ID NO:35, SEQ ID NO:15, SEQ ID NO:16, SEQ ID NO:17, and SEQ ID NO:39 or a sequence that has 90, 95 or 995 sequence identity with a sequence selected from SEQ ID NO:1, SEQ ID NO:2, SEQ ID NO:3, SEQ ID NO:35, SEQ ID NO:15, SEQ ID NO:16, SEQ ID NO:17, and SEQ ID NO:39. In an embodiment, a method of expressing at least one transgene in a plant comprises growing a plant comprising a gene expression cassette comprising a ubiquitin intron operably linked to at least one transgene. In an embodiment, a method of expressing at least one transgene in a plant comprises growing a plant comprising a gene expression cassette comprising a ubiquitin 5'-UTR operably linked to at least one transgene. In an embodiment, a method of expressing at least one transgene in a plant comprises growing a plant comprising a gene expression cassette comprising a ubiquitin promoter, a ubiquitin 5'-UTR, and a ubiquitin intron operably linked to at least one transgene. In an embodiment, a method of expressing at least one transgene in a plant comprises growing a plant comprising a gene expression cassette comprising a ubiquitin 3'-UTR operably linked to at least one transgene. In an embodiment, a method of expressing at least one transgene in a plant tissue or plant cell comprises culturing a plant tissue or plant cell comprising a gene expression cassette a ubiquitin promoter operably linked to at least one transgene. In an embodiment, a method of expressing at least one transgene in a plant tissue or plant cell comprises culturing a plant tissue or plant cell comprising a gene expression cassette a ubiquitin intron operably linked to at least one transgene. In an embodiment, a method of expressing at least one transgene in a plant tissue or plant cell comprises culturing a plant tissue or plant cell comprising a gene expression cassette a ubiquitin 5'-UTR operably linked to at least one transgene. In an embodiment, a method of expressing at least one transgene in a plant tissue or plant cell comprises culturing a plant tissue or plant cell comprising a gene expression cassette a ubiquitin promoter, a ubiquitin 5'-UTR, and a ubiquitin intron operably linked to at least one transgene. In an embodiment, a method of expressing at least one transgene in a plant tissue or plant cell comprises culturing a plant tissue or plant cell comprising a gene expression cassette comprising a ubiquitin 3'-UTR operably linked to at least one transgene.

Transgenic Plants

In an embodiment, a plant, plant tissue, or plant cell comprises a ubiquitin promoter. In an embodiment, a ubiquitin promoter can be a *Panicum virgatum, Brachypodium distachyon* or *Setaria italica* ubiquitin promoter. In an embodiment, a plant, plant tissue, or plant cell comprises a gene expression cassette comprises a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3 or SEQ ID NO:35 wherein the promoter is operably linked to a non-ubiquitin transgene. In an embodiment, a plant, plant tissue, or plant cell comprises a gene expression cassette comprising a sequence selected from SEQ ID NO:1, SEQ ID NO:2, SEQ ID NO:3, SEQ ID NO:35, SEQ ID NO:15, SEQ ID NO:16, SEQ ID NO:17, and SEQ ID NO:39 or a sequence that has 90, 95 or 995 sequence identity with a sequence selected from SEQ ID NO:1, SEQ ID NO:2, SEQ ID NO:3, SEQ ID NO:35, SEQ ID NO:15, SEQ ID NO:16, SEQ ID NO:17, and SEQ ID NO:39 that is operably linked to a non-ubiquitin transgene. In an illustrative embodiment, a plant, plant tissue, or plant cell comprises a gene expression cassette comprising a ubiquitin promoter that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a gene expression cassette comprising a 3'-UTR. In an embodiment, a plant, plant tissue, or plant cell comprises a gene expression cassette comprising a ubiquitin 3'-UTR. In an embodiment, the ubiquitin 3'-UTR is a *Panicum virgatum, Brachypodium distachyon* or *Setaria italica* ubiquitin 3'-UTR. In an embodiment, a 3'-UTR can be the *Brachypodium distachyon* ubiquitin1 C (Ubi1C) 3'-UTR, *Brachypodium distachyon* ubiquitin1 3'-UTR, or *Setaria italica* ubiquitin 3'-UTR.

In an embodiment, a plant, plant tissue, or plant cell comprises a gene expression cassette comprising an intron, wherein the intron is at least 80%, 85%, 90%, 91%, 92%, 93%, 94%, 95%, 96%, 97%, 98%, 99%, 99.5%, 99.8%, or 100% identical to SEQ ID NO:7, SEQ ID NO:8, SEQ ID NO:9, SEQ ID NO:10, or SEQ ID NO:37. In an embodiment, a gene expression cassette comprises a ubiquitin intron that is operably linked to a promoter, wherein the promoter is a *Panicum virgatum, Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a ubiquitin intron that is operably linked to a transgene. In an illustrative embodiment, a plant, plant tissue, or plant cell comprising a gene expression cassette comprising a ubiquitin intron that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a gene expression cassette comprising a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:11, SEQ ID NO:12, SEQ ID NO:13, SEQ ID NO:14, or SEQ ID NO:38. In an embodiment, a gene expression cassette comprises a ubiquitin intron that is operably linked to a promoter, wherein the promoter is a *Panicum virgatum, Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a ubiquitin 5'-UTR that is operably linked to a transgene. In an illustrative embodiment, a plant, plant tissue, or plant cell comprising a gene expression cassette comprising a ubiquitin 5'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a gene expression cassette comprising a ubiquitin promoter and a ubiquitin 3'-UTR. In an embodiment, a plant, plant tissue, or plant cell comprises a ubiquitin promoter and 3'-UTR can each be independently a *Panicum virgatum, Brachypodium distachyon* or *Setaria italica* ubiquitin promoter and a *Panicum virgatum, Brachypodium distachyon* or *Setaria italica* ubiquitin promoter. In an embodiment, a plant, plant tissue, or plant cell comprises a gene expression cassette comprising a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:35 and b) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:4, SEQ ID NO:5, SEQ ID NO:6, or SEQ ID NO:36.

In an embodiment, a plant, plant tissue, or plant cell comprises a gene expression cassette comprising a ubiquitin promoter, ubiquitin 5'-UTR, ubiquitin intron, and a ubiquitin 3'-UTR that are operably linked to a transgene. The promoter, intron, 5'-UTR, and 3'-UTR can be operably linked to different transgenes within a gene expression cassette when a gene expression cassette includes two or more transgenes. In an illustrative embodiment, a gene expression cassette comprises a ubiquitin promoter that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an illustrative embodiment, a gene expression cassette comprises a ubiquitin intron that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an embodiment, a gene expression cassette comprises a ubiquitin intron that is operably linked to a promoter, wherein the promoter is a *Panicum virgatum, Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a ubiquitin 5'-UTR that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an embodiment, a gene expression cassette comprises a ubiquitin 5'-UTR that is operably linked to a promoter, wherein the promoter is a *Panicum virgatum, Brachypodium distachyon* or *Setaria italica* ubiquitin promoter, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a ubiquitin 3'-UTR that is operably linked to a transgene, wherein the 3'-UTR can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a plant, plant tissue, or plant cell comprises a vector comprising a ubiquitin promoter, 5'-UTR, intron, and/or 3'-UTR as disclosed herein. In an embodiment, a plant, plant tissue, or plant cell comprises a vector comprising a ubiquitin promoter, 5'-UTR, intron, and/or 3'-UTR as disclosed herein operably linked to a non-ubiquitin transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus.

In accordance with one embodiment a plant, plant tissue, or plant cell is provided wherein the plant, plant tissue, or plant cell comprises a non-endogenous ubiquitin derived promoter sequence operably linked to a transgene, wherein the ubiquitin derived promoter sequence comprises a sequence SEQ ID NO:1, SEQ ID NO:2, SEQ ID NO:3, or SEQ ID NO:35 or a sequence having 90. 95, 98 or 99% sequence identity with SEQ ID NO:1, SEQ ID NO:2, SEQ ID NO:3, or SEQ ID NO:35. In one embodiment a plant, plant tissue, or plant cell is provided wherein the plant, plant tissue, or plant cell comprises SEQ ID NO: 2, or a sequence that has 90% sequence identity with SEQ ID NO: 2 operably linked to a non-ubiquitin transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*. In accordance with one embodiment the plant, plant tissue, or plant cell comprises SEQ ID NO: 2, SEQ ID NO: 16 or a sequence having 90. 95, 98 or 99% sequence identity with SEQ ID NO: 2 or SEQ ID NO: 16 operably linked to a non-ubiquitin transgene. In one embodiment the plant, plant tissue, or plant cell comprises a promoter operably linked to a transgene wherein the promoter consists of SEQ ID NO: 2, SEQ ID NO: 16 or a sequence having 90. 95, 98 or 99% sequence identity with SEQ ID NO: 2 or SEQ ID NO: 16. In accordance with one embodiment the gene construct comprising non-endogenous ubiquitin derived promoter sequence operably linked to a transgene is incorporated into the genome of the plant, plant tissue, or plant cell.

In one embodiment a non-*Brachypodium* plant, plant tissue, or plant cell is provided comprising SEQ ID NO: 2, or a sequence that has 90, 95, 98 or 99% sequence identity with SEQ ID NO: 2, operably linked to a transgene. In accordance with one embodiment the non-*Brachypodium plant, plant tissue, or plant cell is a dicotyledonous or monocotyledonous plant or plant cell or tissue derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is Zea mays.* In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO: 12 or a sequence that has 90% sequence identity with SEQ ID NO: 12, wherein the 5' untranslated sequence is inserted between, and operably linked to, said promoter and said transgene. In a further embodiment the plant, plant tissue, or plant cell further comprises an intron sequence inserted after the 5' untranslated sequence. In one embodiment the intron sequence is an intron sequence isolated from a ubiquitin gene of *Panicum virgatum, Brachypodium distachyon*, or *Setaria italica*. In one embodiment the sequence comprises or consists of SEQ ID NO: 8.

In one embodiment a non-*Brachypodium* plant, plant tissue, or plant cell is provided that comprises SEQ ID NO: 2, or a sequence that has 90. 95, 98 or 99% sequence identity with SEQ ID NO: 2, operably linked to the 5' end of a transgene and a 3' untranslated sequence comprising SEQ ID NO: 5 or a sequence that has 90% sequence identity with SEQ ID NO: 5, wherein the 3' untranslated sequence is operably linked to said transgene. In accordance with one embodiment the non-*Brachypodium* plant, plant tissue, or plant cell is a dicotyledonous or monocotyledonous plant or is a plant issue or cell derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*. In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO: 12 or a sequence that has 90% sequence identity with SEQ ID NO: 12, wherein the 5' untranslated sequence is inserted between, and operably linked to, said promoter and said transgene. In a further embodiment the plant, plant tissue, or plant cell further comprises an intron sequence inserted after the 5' untranslated sequence. In one embodiment the intron sequence is an intron sequence isolated from a ubiquitin gene of *Panicum virgatum, Brachypodium distachyon*, or *Setaria italica*. In one embodiment the 5' untranslated sequence consists of SEQ ID NO: 12.

In one embodiment a non-*Brachypodium* plant, plant tissue, or plant cell is provided that comprises SEQ ID NO: 16, or a sequence having 90% sequence identity with SEQ ID NO: 16 operably linked to a transgene. In one embodiment a non-*Brachypodium* plant, plant tissue, or plant cell is provided that comprises a promoter operably linked to a transgene, wherein the promoter consists of SEQ ID NO: 16, or a sequence having 90% sequence identity with SEQ ID NO: 16. In a further embodiment non-*Brachypodium* plant, plant tissue, or plant cell further comprises a 3' untranslated sequence of a ubiquitin gene of *Panicum virgatum, Brachypodium distachyon*, or *Setaria italica*. In one embodiment the 3' untranslated sequence comprises or consists of SEQ ID NO: 5 or a sequence that has 90% sequence identity with SEQ ID NO: 5, wherein the 3' untranslated sequence is operably linked to 3' end of the transgene.

In an embodiment, a plant, plant tissue, or plant cell according to the methods disclosed herein can be a monocotyledonous plant. The monocotyledonous plant, plant tissue, or plant cell can be, but not limited to corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be a dicotyledonous plant. The dicotyledonous plant, plant tissue, or plant cell can be, but not limited to rapeseed, canola, indian mustard, ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) Next Generation Sequencing analysis; 5) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase), EC 2.3.1.183) proteins using an ELISA assay is described in U.S. Patent Publication No. 20090093366 which is herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

While the invention has been described with reference to specific methods and embodiments, it will be appreciated that various modifications and changes may be made without departing from the invention.

Example 1

Transformation of *Agrobacterium tumefaciens*

The binary expression vectors were transformed into *Agrobacterium tumefaciens* strain DAt13192 (RecA minus ternary strain) (Int'l. Pat. Pub. No. WO2012016222). Bacterial colonies were isolated, and binary plasmid DNA was isolated and confirmed via restriction enzyme digestion.

Corn Transformation

*Agrobacterium* Culture Initiation.

*Agrobacterium* cultures were streaked from glycerol stocks onto *Agrobacterium* (AB) minimal medium (as disclosed in WO 2013090734, the disclosure of which is incorporated herein by reference) and incubated at 20° C. in the dark for 3 days. *Agrobacterium* cultures were then streaked onto a plate of YEP (see WO 2013090734) medium and incubated at 20° C. in the dark for 1 day.

On the day of the experiment, a mixture of inoculation medium (see WO 2013090734) and acetosyringone were prepared in a volume appropriate to the number of bacterial strains comprising plant transformation constructs in the experiment. Inoculation medium was pipetted into a sterile, disposable 250 ml flask. Next, a 1 M stock solution of acetosyringone in 100% dimethyl sulfoxide was added to the flask containing inoculation medium in a volume appropriate to make a final acetosyringone concentration of 200 µM. The required volumes of Inoculation medium and 1 M acetosyringone stock solution are listed in TABLE 1.

TABLE 1

The amount of inoculation medium/acetosyringone mixture to make according to the number of constructs being prepared

| Number of constructs to prepare | Inoculation medium (mL) | 1M acetosyringone stock (µL) |
|---|---|---|
| 1 | 50 | 10 |
| 2 | 100 | 20 |
| 3 | 150 | 30 |
| 4 | 200 | 40 |
| 5 | 250 | 50 |

For each construct, 1-2 loops of *Agrobacterium* from the YEP plate were suspended in 15 ml of the inoculation medium/acetosyringone mixture inside a sterile, disposable 50 ml centrifuge tube, and the optical density of the solution at 600 nm ($OD_{600}$) was measured in a spectrophotometer. The suspension was then diluted down to 0.25-0.35 $OD_{600}$ using additional inoculation medium/acetosyringone mixture. The tube of *Agrobacterium* suspension was then placed horizontally on a platform shaker set at about 75 rpm at room temperature and incubated between 1 and 4 hours before use.

Ear Sterilization and Embryo Isolation.

Ears from *Zea mays* cultivar B104 were harvested 10-12 days post pollination. Harvested ears were de-husked and surface-sterilized by immersion in a 20% solution of commercial bleach (Ultra Clorox® Germicidal Bleach, 6.15% sodium hypochlorite) and two drops of Tween® 20, for 20 minutes, followed by three rinses in sterile, deionized water inside a laminar flow hood. Immature zygotic embryos (1.8-2.2 mm long) were aseptically excised from each ear and distributed into one or more micro-centrifuge tubes containing 2.0 ml of *Agrobacterium* suspension into which 2 µl of 10% Break-Thru® S233 surfactant had been added.

*Agrobacterium* Co-Cultivation.

Upon completion of the embryo isolation activity, the tube of embryos was closed and placed on a rocker platform for 5 minutes. The contents of the tube were then poured out onto a plate of co-cultivation medium, and the liquid *Agrobacterium* suspension was removed with a sterile, disposable transfer pipette. The co-cultivation plate containing embryos was placed at the back of the laminar flow hood with the lid ajar for 30 minutes; after which time the embryos were oriented with the scutellum facing up using a microscope. The co-cultivation plate with embryos was then returned to the back of the laminar flow hood with the lid ajar for a further 15 minutes. The plate was then closed, sealed with 3M® Micropore® tape, and placed in an incubator at 25° C. with 24 hours/day light at approximately 60 µmol $m^{-2}$ $s^{-1}$ light intensity Callus Selection and Regeneration of Transgenic Events.

Following the co-cultivation period, embryos were transferred to Resting medium (see WO 2013090734). No more than 36 embryos were moved to each plate. The plates were placed in clear boxes and incubated at 27° C. with 24 hours/day light at approximately 50 µmol $m^{-2}$ $s^{-1}$ light intensity for 7-10 days. Callused embryos were then transferred onto Selection I medium (see WO 2013090734). No more than 18 callused embryos were moved to each plate of Selection I. The plates were placed in clear boxes and incubated at 27° C. with 24 hours/day light at approximately 50 µmol $m^{-2}$ $s^{-1}$ light intensity for 7 days. Callused embryos were then transferred to Selection II medium (see WO 2013090734). No more than 12 callused embryos were moved to each plate of Selection II media. The plates were placed in clear boxes and incubated at 27° C. with 24 hours/day light at approximately 50 µmol $m^{-2}$ $s^{-1}$ light intensity for 14 days.

At this stage resistant calli were moved to Pre-Regeneration medium (see WO 2013090734). No more than 9 calli were moved to each plate of Pre-Regeneration media. The plates were placed in clear boxes and incubated at 27° C. with 24 hours/day light at approximately 50 µmol $m^{-2}$ $s^{-1}$ light intensity for 7 days. Regenerating calli were then transferred to Regeneration medium in Phytatrays™ (see WO 2013090734). and incubated at 28° C. with 16 hours light/8 hours dark per day at approximately 150 µmol $m^{-2}$ $s^{-1}$ light intensity for 7-14 days or until shoots develop. No more than 5 calli were placed in each Phytatray™. Small shoots with primary roots were then isolated and transferred to Shoot Elongation medium (see WO 2013090734). Rooted plantlets about 6 cm or taller were transplanted into soil and moved out to a growth chamber for hardening off.

YFP Transient Expression.

Transient YFP expression was observed in transformed embryos and after 3 days of co-cultivation with *Agrobacterium*. The embryos were observed under a stereomicroscope (Leica Microsystems, Buffalo Grove, Ill.) using a YFP filter and 500 nm light source.

Transfer and Establishment of T₀ Plants in the Greenhouse.

Transgenic plants were transferred on a regular basis to the greenhouse. Plants were transplanted from Phytatrays™ to small pots (T. O. Plastics, 3.5" SVD, 700022C) filled with growing media (Premier Tech Horticulture, ProMix BX, 0581 P) and covered with humidomes to help acclimate the plants. Plants were placed in a Conviron growth chamber (28° C./24° C., 16-hour photoperiod, 50-70% RH, 200 μmol m$^{-2}$ s$^{-1}$ light intensity) until reaching V3-V4 stage. This aided in acclimating the plants to soil and harsher temperatures. Plants were then moved to the greenhouse (Light Exposure Type: Photo or Assimilation; High Light Limit: 1200 μmol m$^{-2}$ s$^{-1}$ photosynthetically active radiation (PAR); 16-hour day length; 27° C. Day/24° C. Night) and transplanted from the small pots to 5.5 inch pots. Approximately 1-2 weeks after transplanting to larger pots plants were sampled for bioassay. One plant per event was assayed.

Example 2

Identification of the Promoters

The maize ubiquitin coding sequence was BLASTx searched in the Phytozome (Goodstein et al., 2012) database using *Brachypodium distachyon* and *Setaria italica* as target genomes.

```
Maize Ubiquitin (ZM Ubi1) Coding Sequence
                                        (SEQ ID NO: 18)
ATGCAGATCTTTGTGAAAACCCTGACTGGCAAGACTATCACCCTCGAGG

TGGAGTCGTCTGACACCATTGACAACGTTAAGGCCAAGATCCAGGACAA

GGAGGGCATCCCCCCAGACCAGCAGCGGCTCATCTTTGCTGGCAAACAG

CTTGAGGACGGGCGCACGCTTGCTGACTACAACATCCAGAAGGAGAGCA

CCCTCCACCTTGTGCTCCGTCTCAGGGGAGGCATGCAGATCTTTGTGAA

AACCCTGACCGGCAAGACTATCACCCTCGAGGTGGAGTCCTCTGACACC

ATTGACAACGTCAAGGCCAAGATCCAGGACAAGGAGGGCATCCCTCCAG

ACCAGCAGCGGCTCATCTTTGCTGGGAAGCAGCTTGAGGACGGGCGCAC

GCTTGCCGACTACAACATCCAGAAGGAGAGCACCCTCCACTTGGTGCTG

CGCCTCAGGGGAGGCATGCAGATCTTCGTGAAGACCCTGACCGGCAAGA

CTATCACCCTCGAGGTGGAGTCTTCAGACACCATCGACAACGTCAAGGC

CAAGATCCAGGACAAGGAGGGCATTCCCCCAGACCAGCAGCGGCTCATC

TTTGCTGGAAAGCAGCTTGAGGACGGGCGCACGCTTGCCGACTACAACA

TCCAGAAGGAGAGCACCCTCCACTTGGTGCTGCGCCTCAGGGGAGGCAT

GCAGATCTTCGTGAAGACCCTGACCGGCAAGACTATCACCCTCGAGGTG

GAGTCTTCAGACACCATCGACAATGTCAAGGCCAAGATCCAGGACAAGG

AGGGCATCCCACCGGACCAGCAGCGTTTGATCTTCGCTGGCAAGCAGCT

GGAGGATGGCCGCACCCTTGCGGATTACAACATCCAGAAGGAGAGCACC

CTCCACCTGGTGCTCCGTCTCAGGGGTGGTATGCAGATCTTTGTGAAGA

CACTCACTGGCAAGACAATCACCCTTGAGGTGGAGTCTTCGGATACCAT

TGACAATGTCAAGGCCAAGATCCAGGACAAGGAGGGCATCCCACCCGAC

CAGCAGCGCCTCATCTTCGCCGGCAAGCAGCTGGAGGATGGCCGCACCC

TGGCGGATTACAACATCCAGAAGGAGAGCACTCTCCACCTGGTGCTCCG

CCTCAGGGGTGGCATGCAGATTTTTGTGAAGACATTGACTGGCAAGACC

ATCACCTTGGAGGTGGAGAGCTCTGACACCATTGACAATGTGAAGGCCA

AGATCCAGGACAAGGAGGGCATTCCCCCAGACCAGCAGCGTCTGATCTT

TGCGGGCAAGCAGCTGGAGGATGGCCGCACTCTCGCGGACTACAACATC

CAGAAGGAGAGCACCCTTCACCTTGTTCTCCGCCTCAGAGGTGGTATGC

AGATCTTTGTAAAGACCCTGACTGGAAAAACCATAACCCTGGAGGTTGA

GAGCTCGGACACCATCGACAATGTGAAGGCGAAGATCCAGGACAAGGAG

GGCATCCCCCCGGACCAGCAGCGTCTGATCTTCGCCGGCAAACAGCTGG

AGGATGGCCGCACCCTAGCAGACTACAACATCCAAAAGGAGAGCACCCT

CCACCTTGTGCTCCGTCTCCGTGGTGGTCAGTAA
```

The protein alignments are shown in FIG. 1. Two sequences that aligned with the *Zea mays* Ubiquitin 1 protein were identified from *Brachypodium distachyon*. Only one sequence that aligned with the *Zea mays* Ubiquitin 1 protein was identified each from *Setaria italic* and *Panicum virgatum*. An approximately 2 kb DNA sequence upstream from a predicted translational start site (ATG) was determined to be the beginning of the putative promoter sequence and used for expression characterization. The polynucleotide sequence alignments of the novel promoters that were isolated from *Panicum virgatum*, *Brachypodium distachyon* and *Setaria italica* were aligned to the ZM Ubi1 promoter and found to share low levels of sequence similarity across the 2 kb DNA region (FIGS. 2A-C).

The UBI coding sequence and putative promoter for the *Panicum virgatum*, *Brachypodium distachyon* and *Setaria italica* ubiquitin genes are indicated in FIGS. 35-38.

Example 3

Vector Construction

Figure 3:
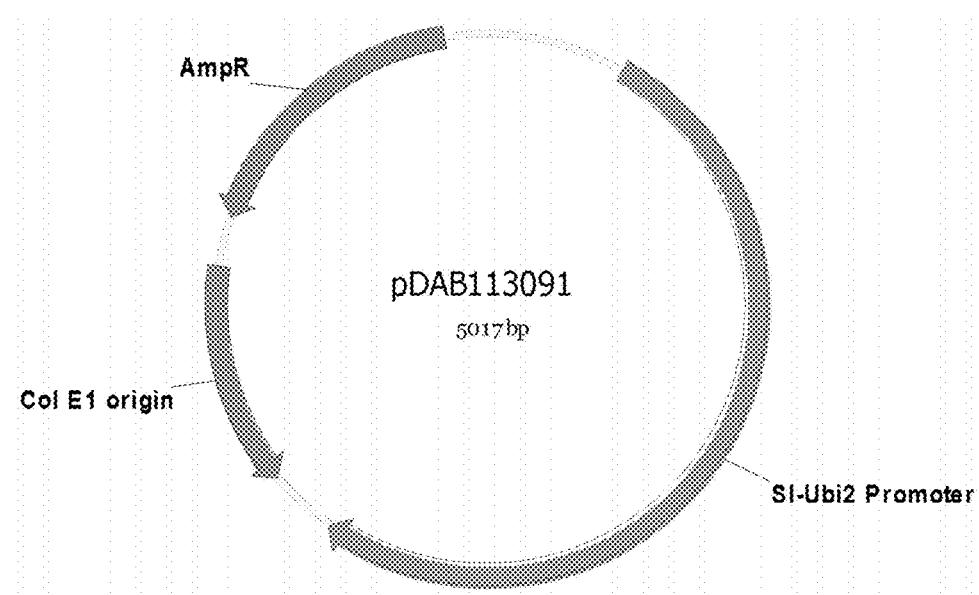
FIG. 3 is a plasmid map showing the synthesized *Setaria italica* Ubiquitin2 promoter genetic element.
Figure 4:
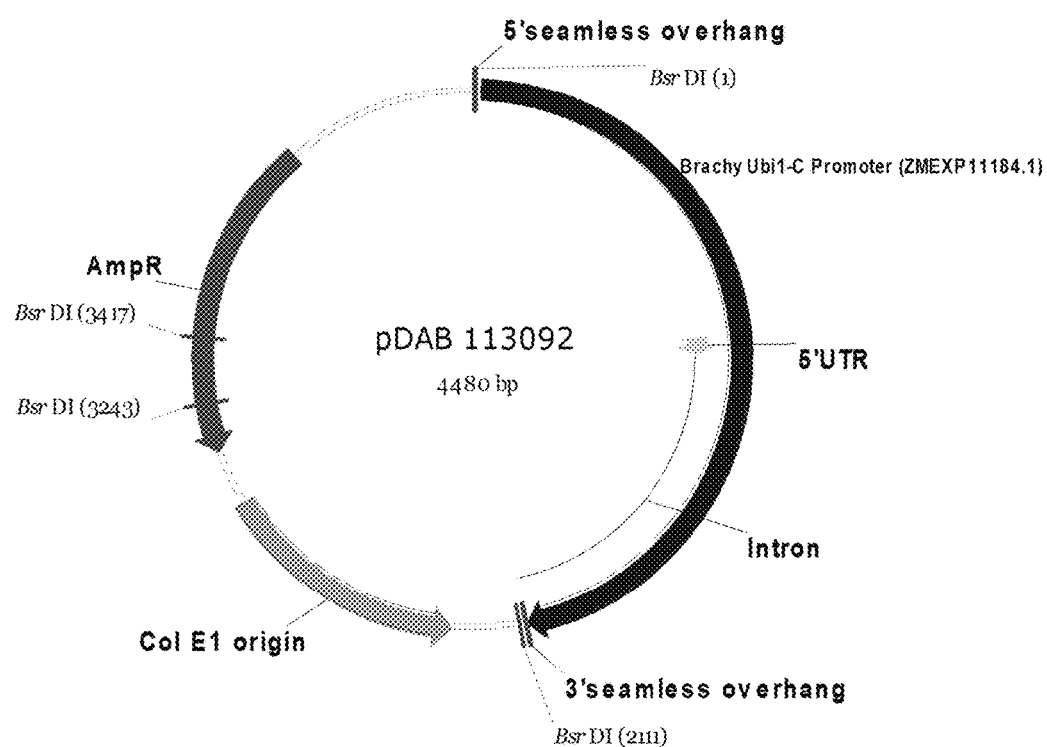
FIG. 4 is a plasmid map showing the synthesized *Brachypodium distachyon* Ubiquitin1 C promoter genetic element and flanking seamless cloning overhang location.
Figure 5:
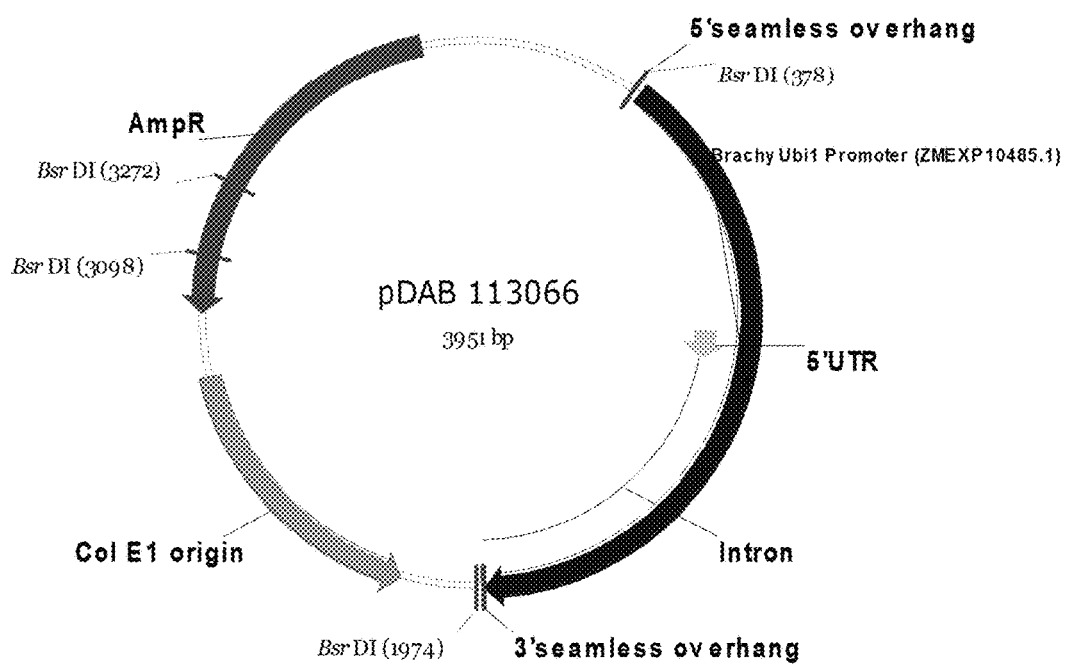
FIG. 5 is a plasmid map showing the synthesized *Brachypodium distachyon* Ubiquitin1 promoter genetic element and flanking seamless cloning overhang location.
Figure 6:
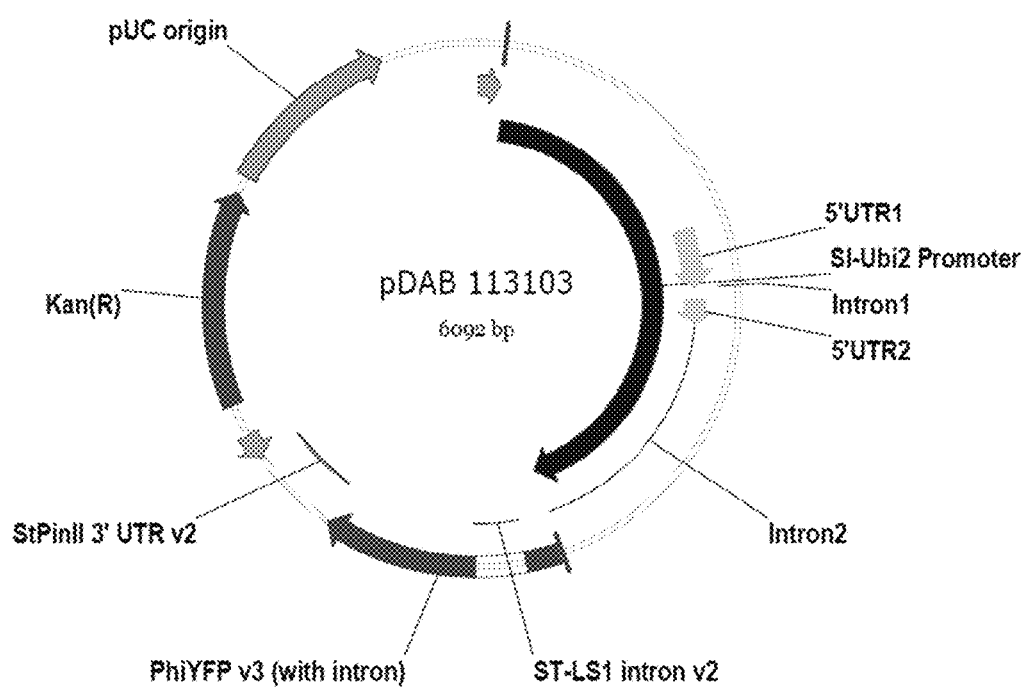
FIG. 6 is a plasmid map showing the expression vector containing *Setaria italica* ubiquitin2 (SI-Ubi2) promoter fused to PhiYFP reporter gene.
Figure 7:
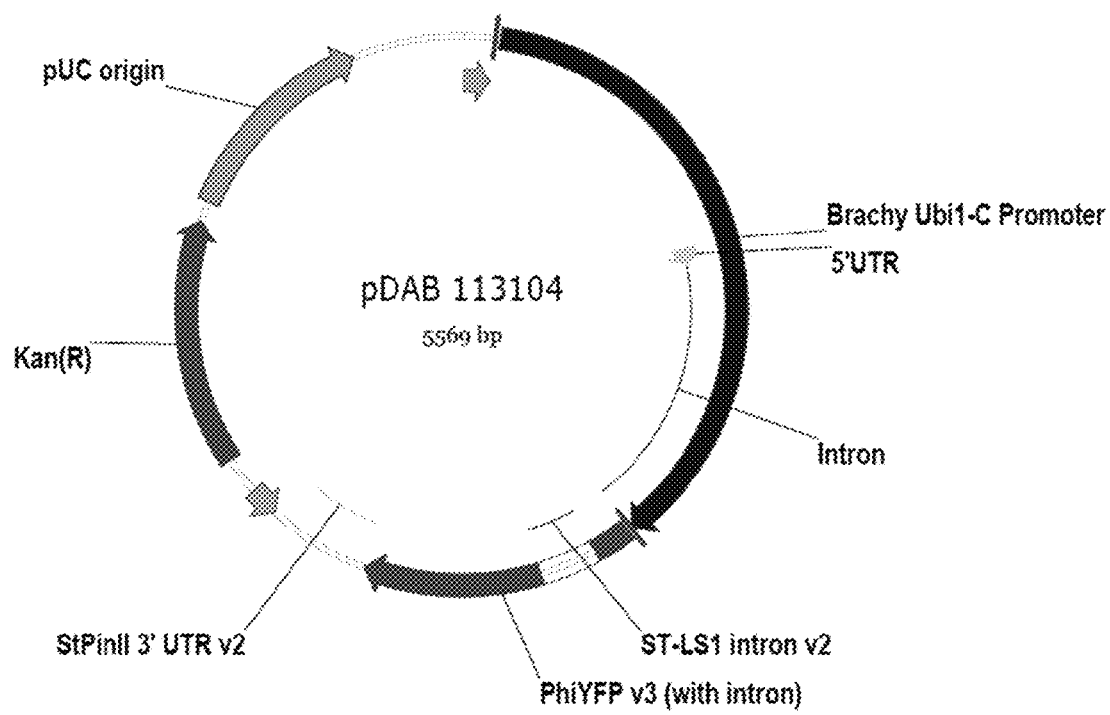
FIG. 7 is a plasmid map showing the expression vector containing *Brachypodium distachyon* Ubiquitin1 C promoter fused to PhiYFP reporter gene.
Figure 8:
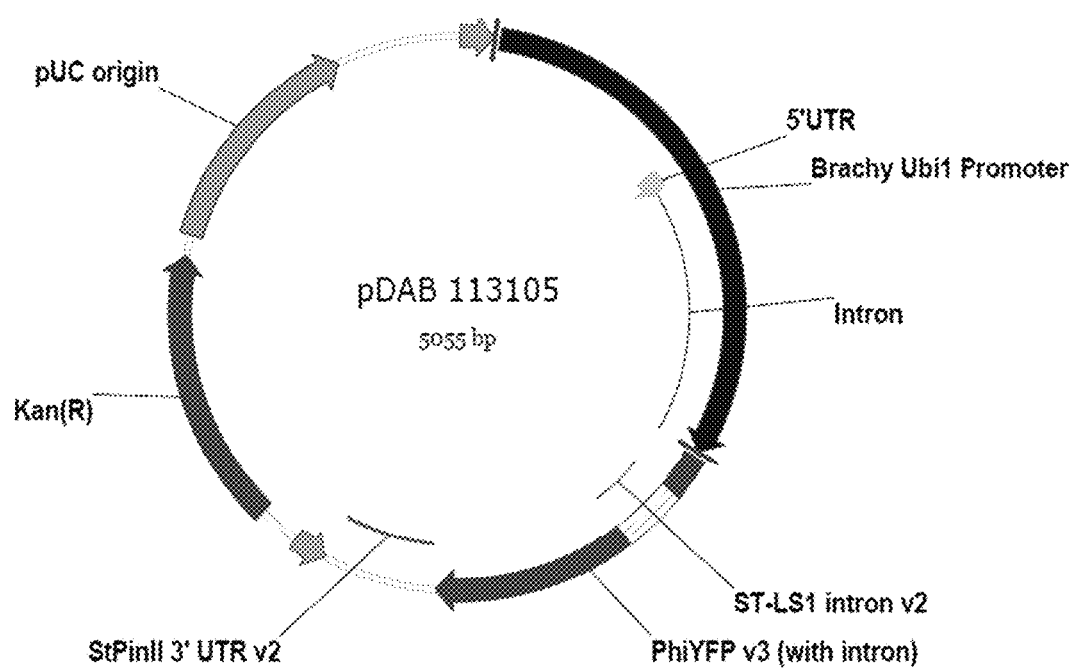
FIG. 8 is a plasmid map showing the expression vector containing *Brachypodium distachyon* Ubiquitin1 promoter fused to PhiYFP reporter gene.
Figure 9:
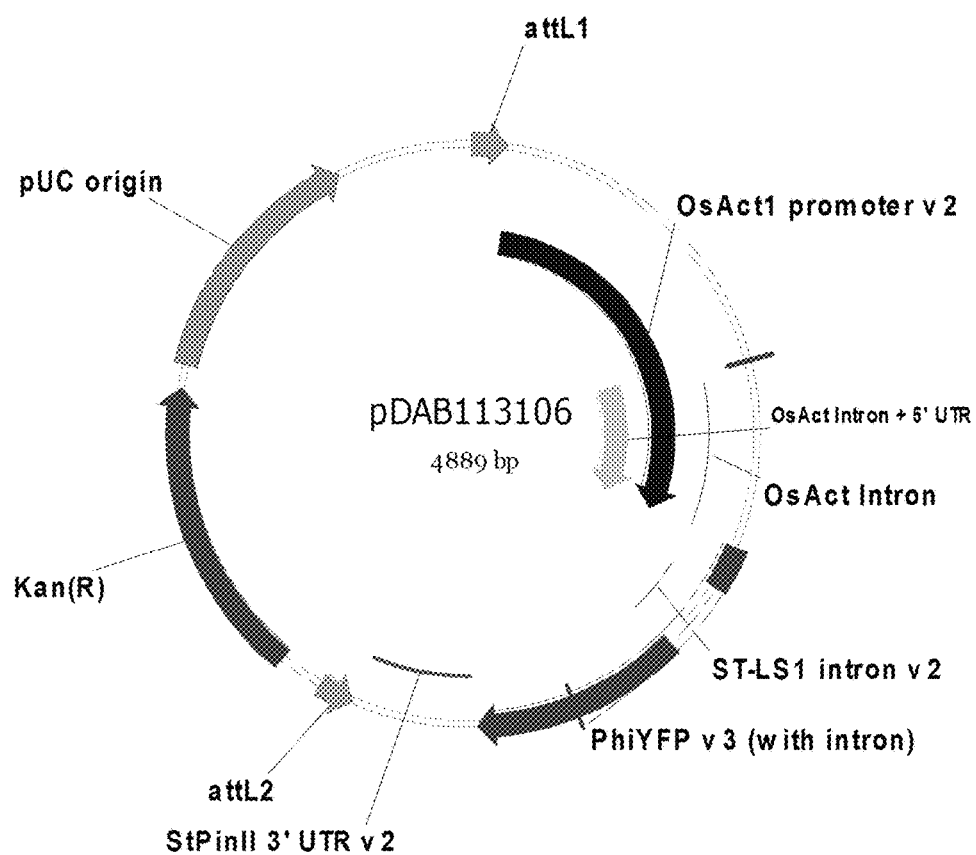
FIG. 9 is a plasmid map showing the expression vector containing OS Act1 (Rice Actin1) promoter fused to PhiYFP reporter gene.
Figure 10:
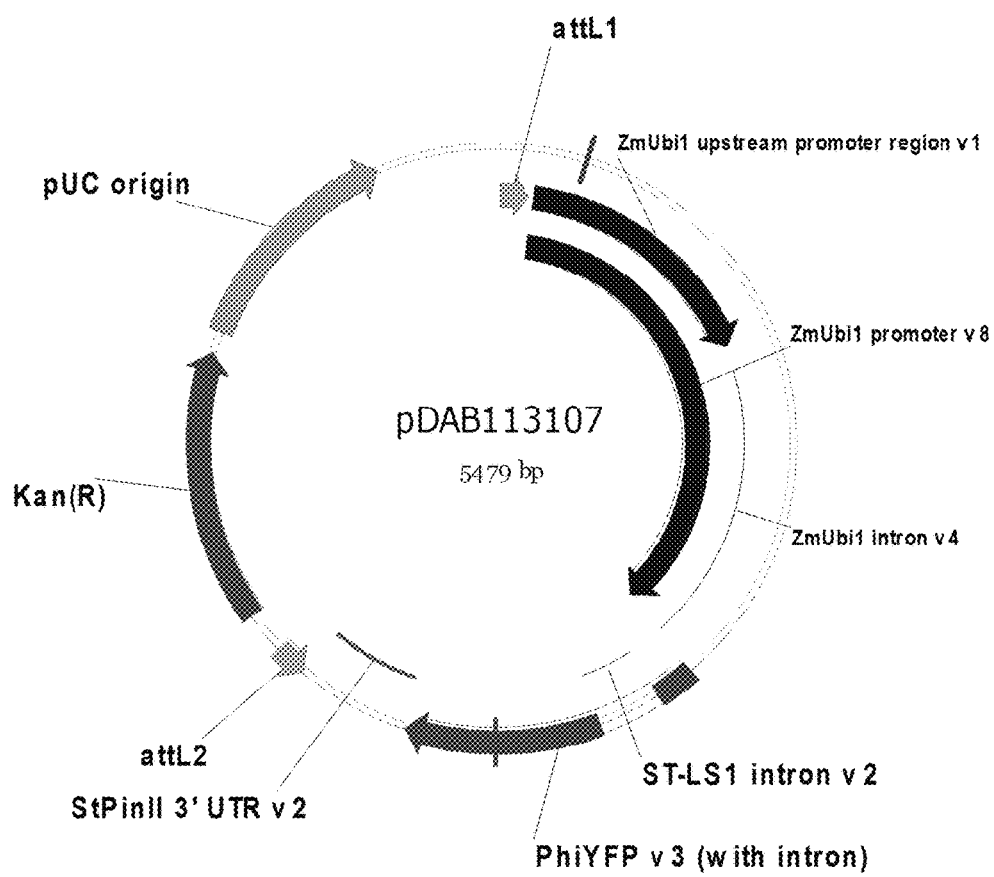
FIG. 10 is a plasmid map showing the expression vector containing ZM Ubi1 promoter fused to PhiYFP reporter gene.
Figure 11:
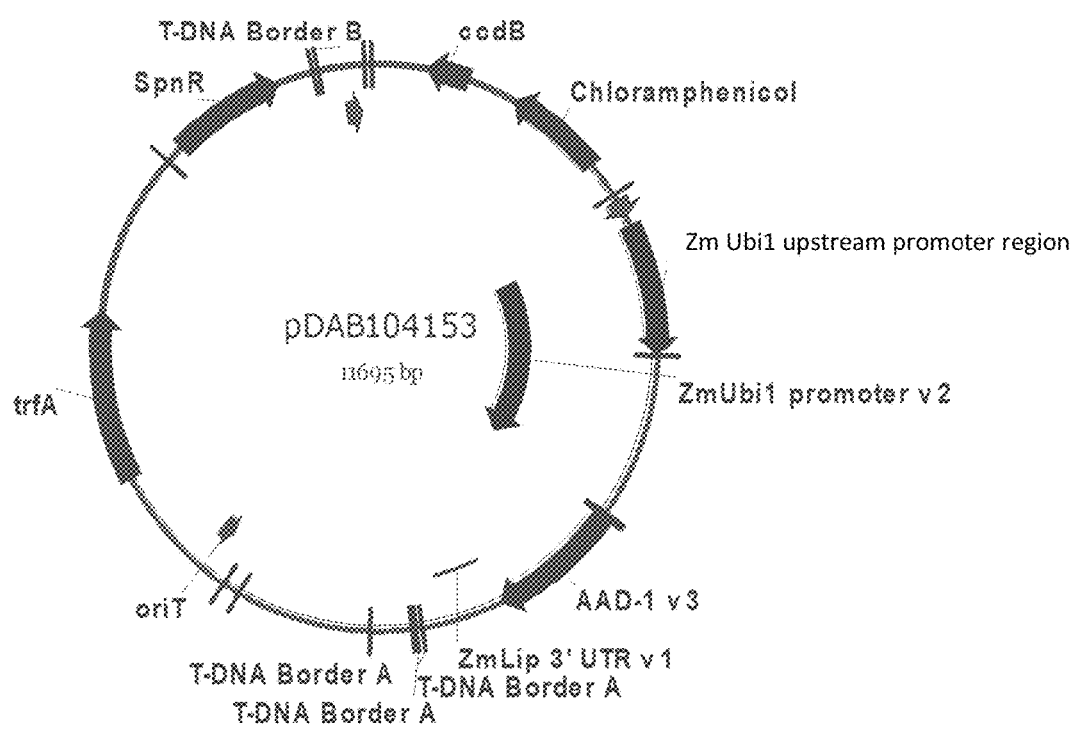
FIG. 11 is a plasmid map showing the binary destination vector used to build binary expression vectors using Gateway technology.
Figure 12:
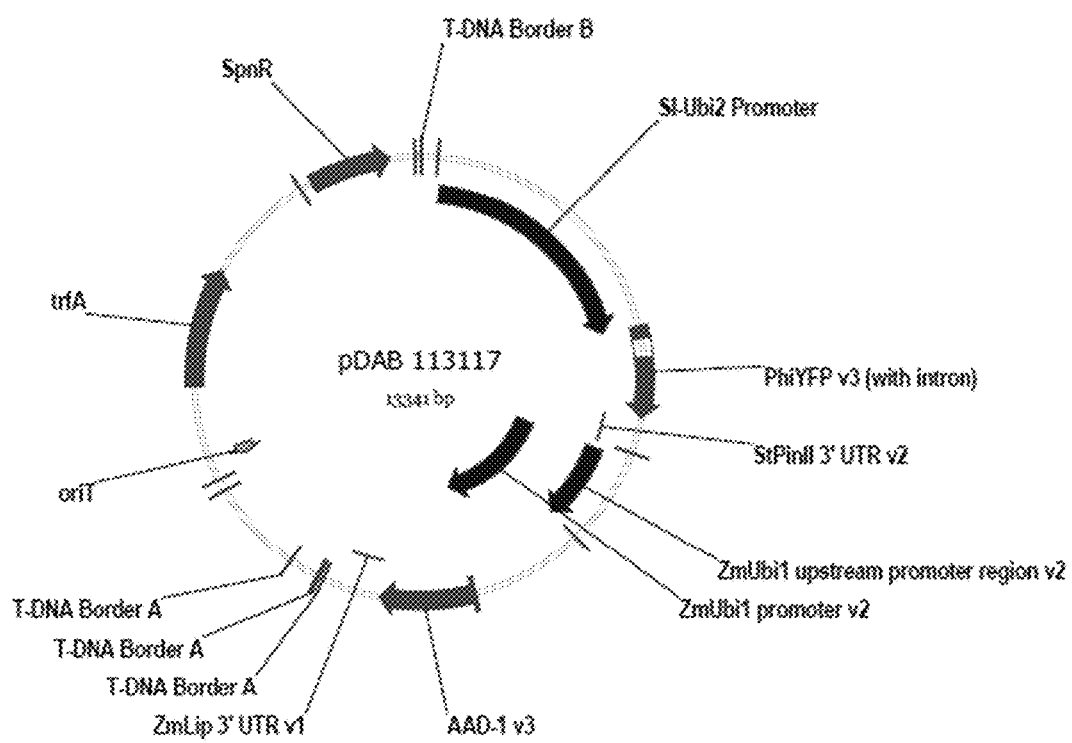
FIG. 12 is a plasmid map showing the binary expression vector containing *Setaria italica* Ubiquitin2 (SI-Ubi2) promoter fused to yellow fluorescent protein (Phi YFP) marker gene coding region containing ST-LS1 intron followed by fragment comprising a StPinII 3'UTR from potato.
Figure 13:
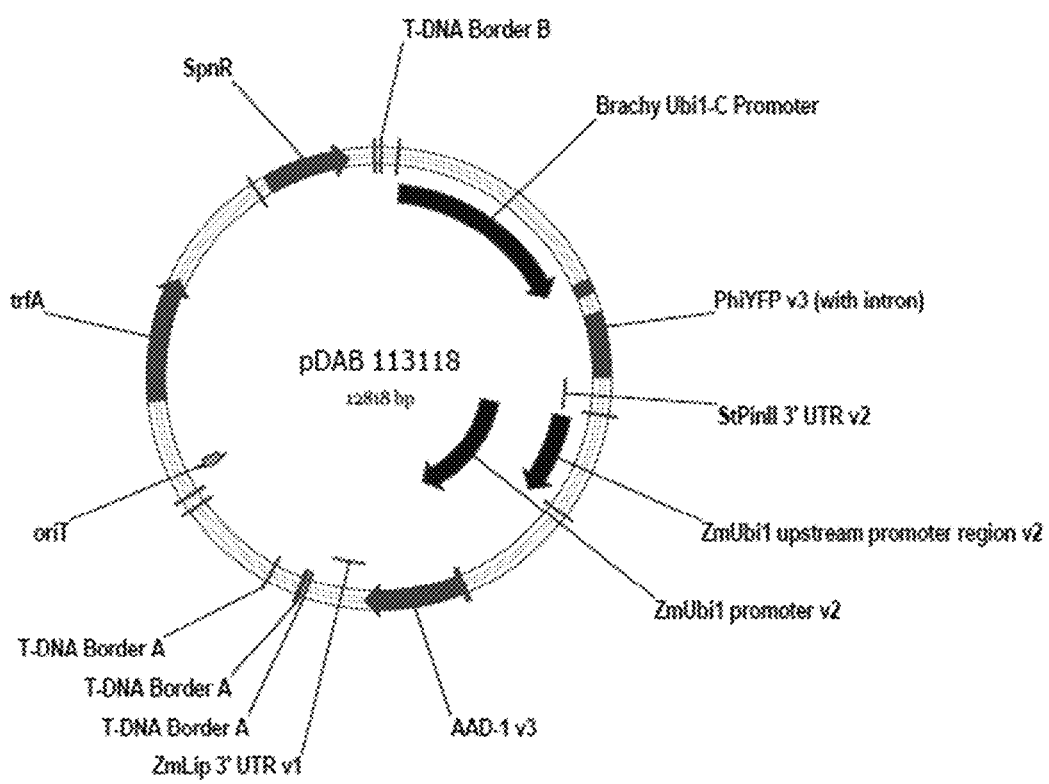
FIG. 13 is a plasmid map showing the binary expression vector containing *Brachypodium distachyon* Ubiquitin1 C promoter fused to yellow fluorescent protein (Phi YFP) marker gene coding region containing ST-LS1 intron followed by fragment comprising a StPinII 3'UTR from potato.
Figure 14:
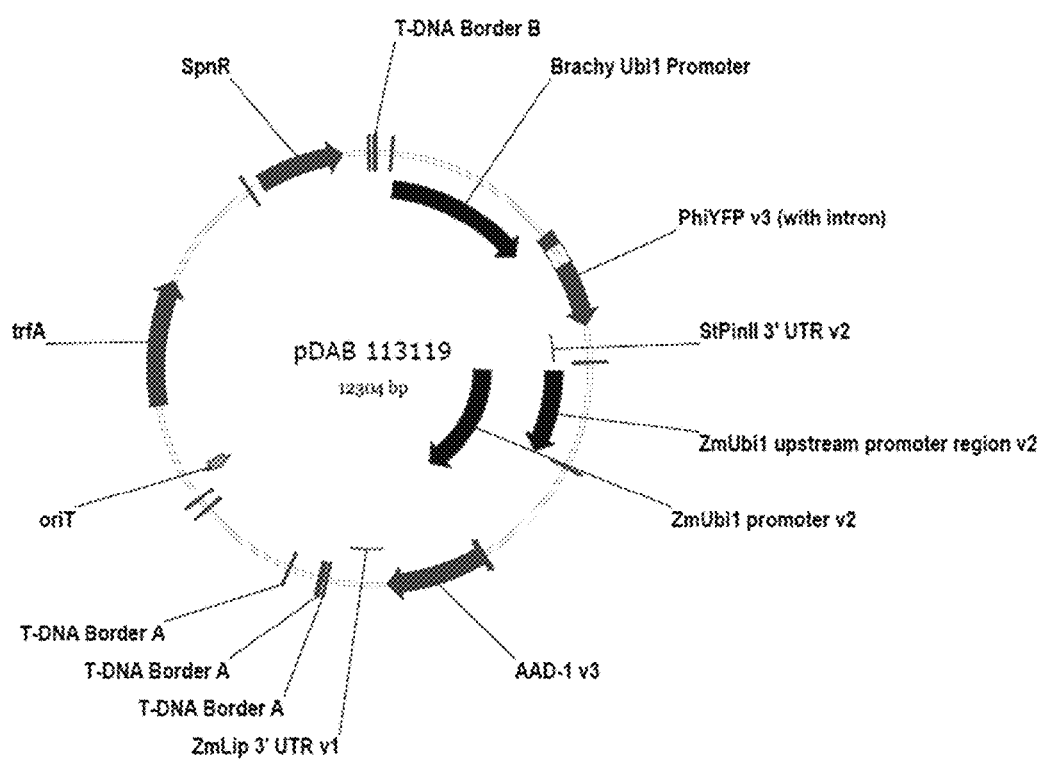
FIG. 14 is a plasmid map showing the binary expression vector containing *Brachypodium distachyon* Ubiquitin1 promoter fused to yellow fluorescent protein (Phi YFP) marker gene coding region containing ST-LS1 intron followed by fragment comprising a StPinII 3'UTR from potato.
Figure 15:
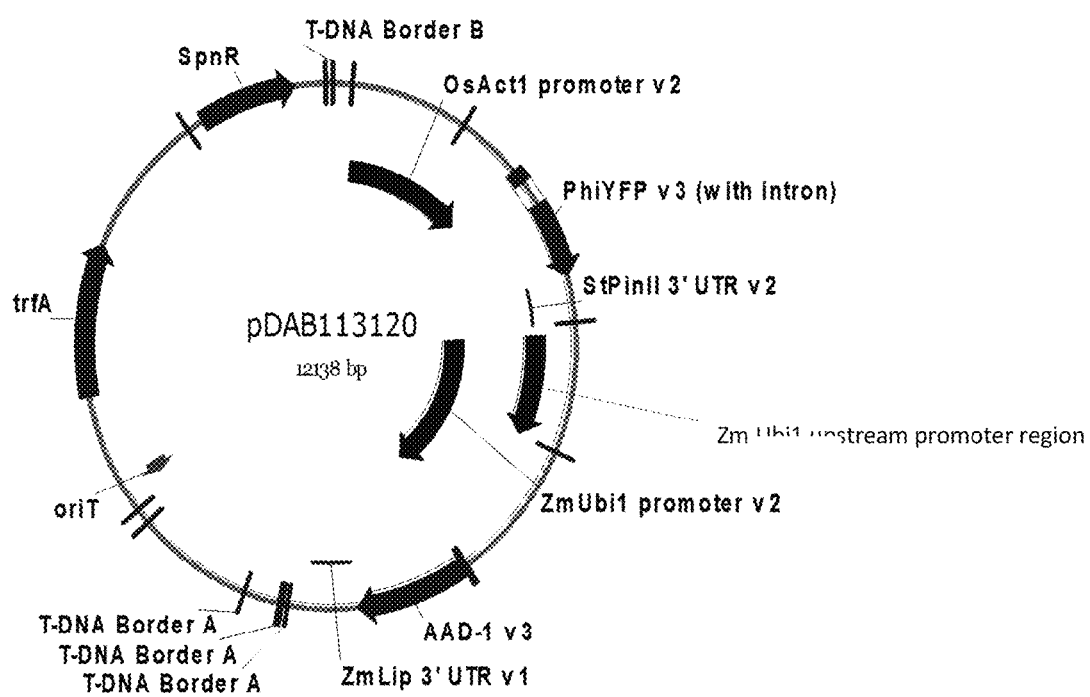
FIG. 15 is a plasmid map showing the binary expression vector containing OS Act1 promoter fused to yellow fluorescent protein (Phi YFP) marker gene coding region containing ST-LS1 intron followed by fragment comprising a StPinII 3'UTR from potato.
Figure 16:
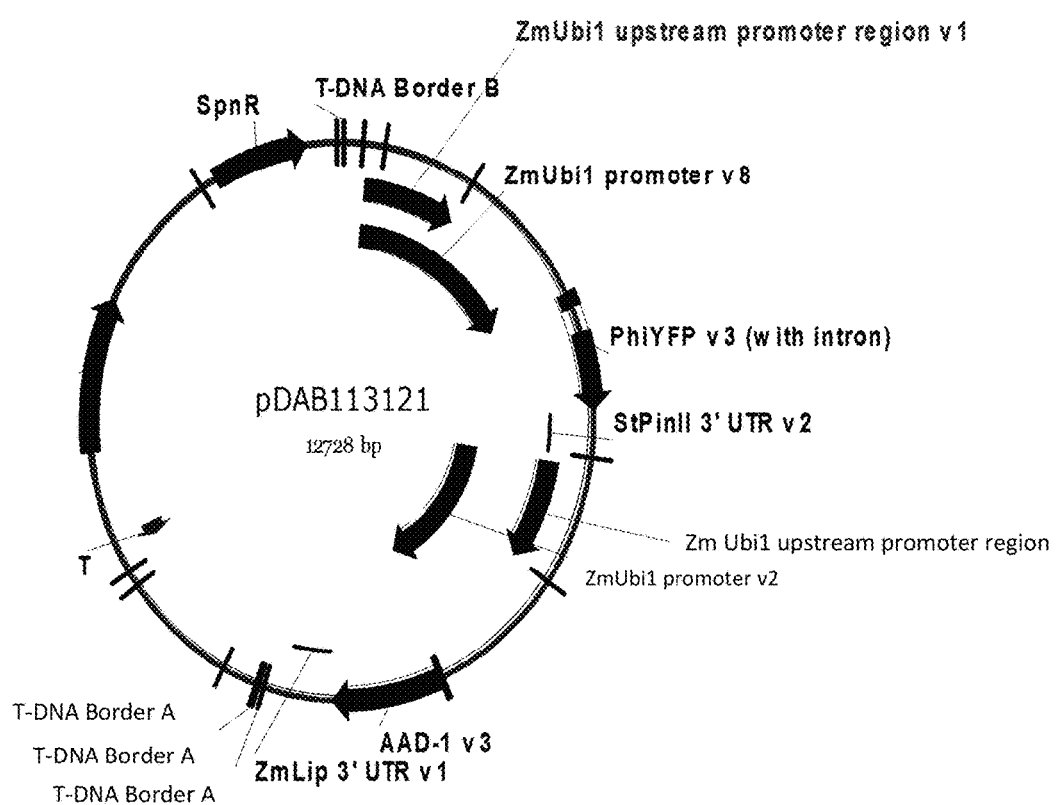
FIG. 16 is a plasmid map showing the binary expression vector containing ZM Ubi1 promoter fused to yellow fluorescent protein (Phi YFP) marker gene coding region containing ST-LS1 intron followed by fragment comprising a StPinII 3'UTR from potato.
Figure 22:
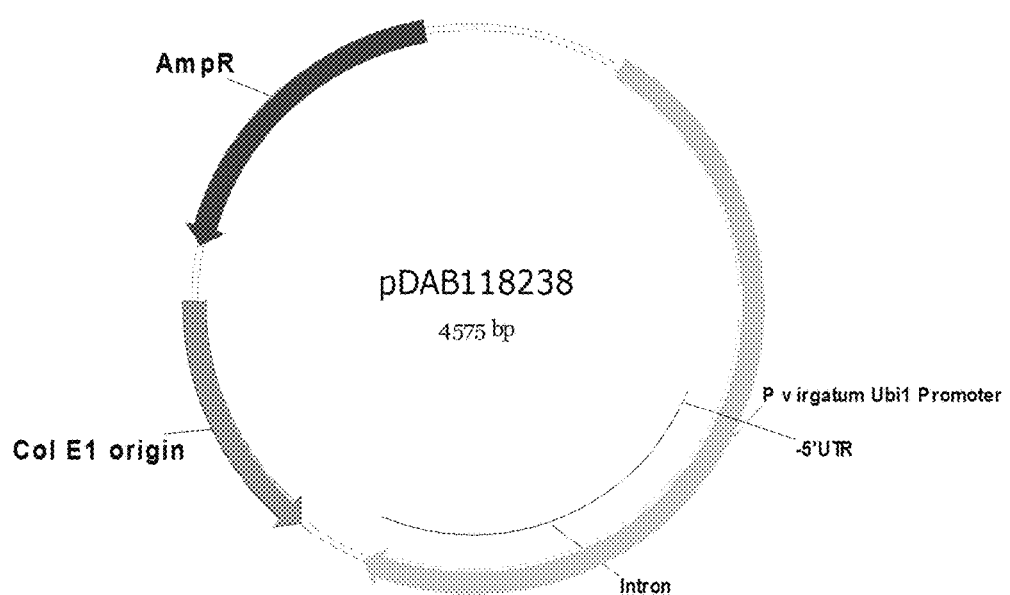
FIG. 22 is a plasmid map showing the synthesized *Panicum virgatum* Ubiquitin1 promoter genetic element and flanking seamless cloning overhang location.
Figure 23:
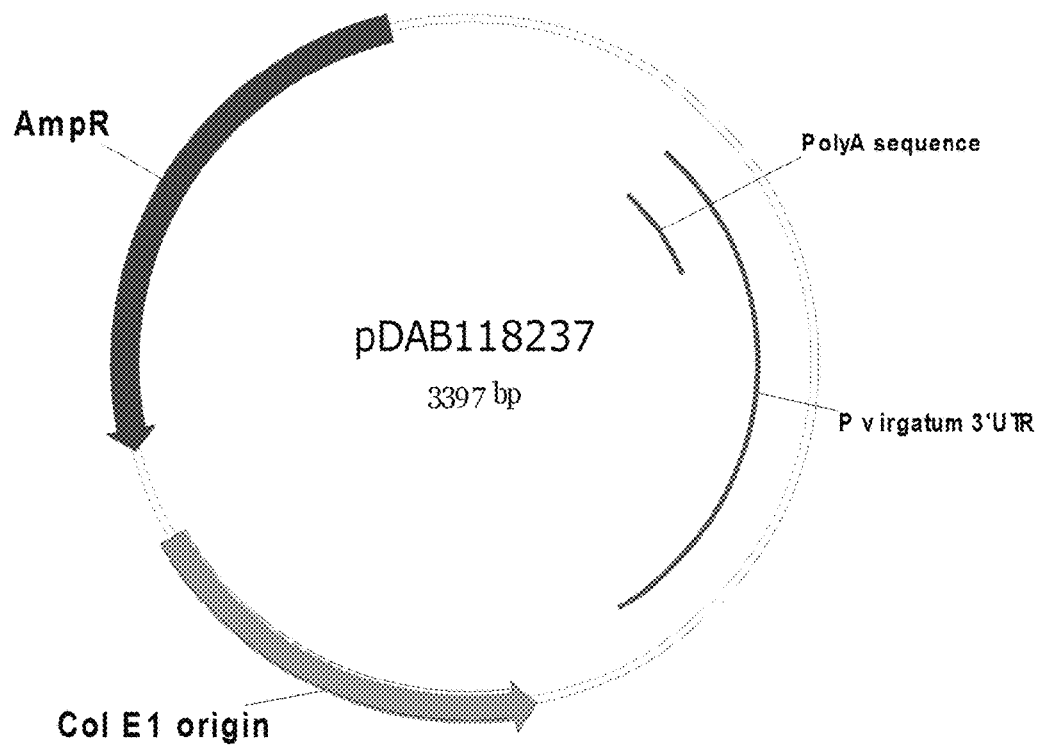
FIG. 23 is plasmid map showing the synthesized *Panicum virgatum* Ubiquitin1 3'UTR genetic element and flanking seamless cloning overhang location.
Figure 24:
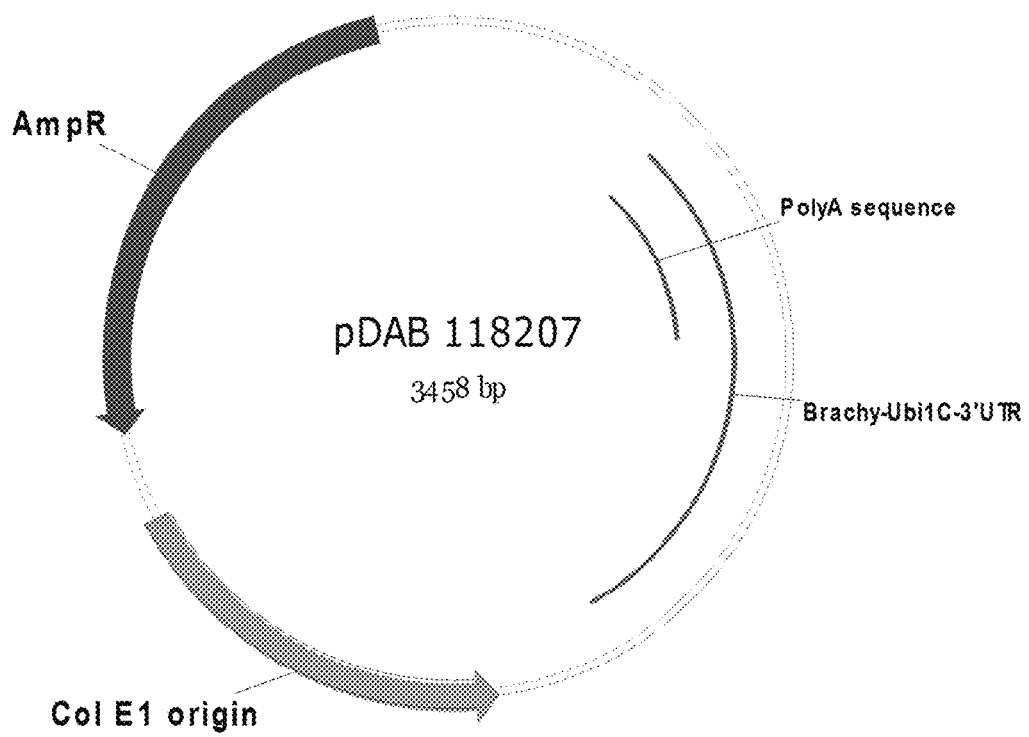
FIG. 24 is plasmid map showing the synthesized *Brachypodium distachyon* Ubiquitin1C 3'UTR genetic element and flanking seamless cloning overhang location.
Figure 25:
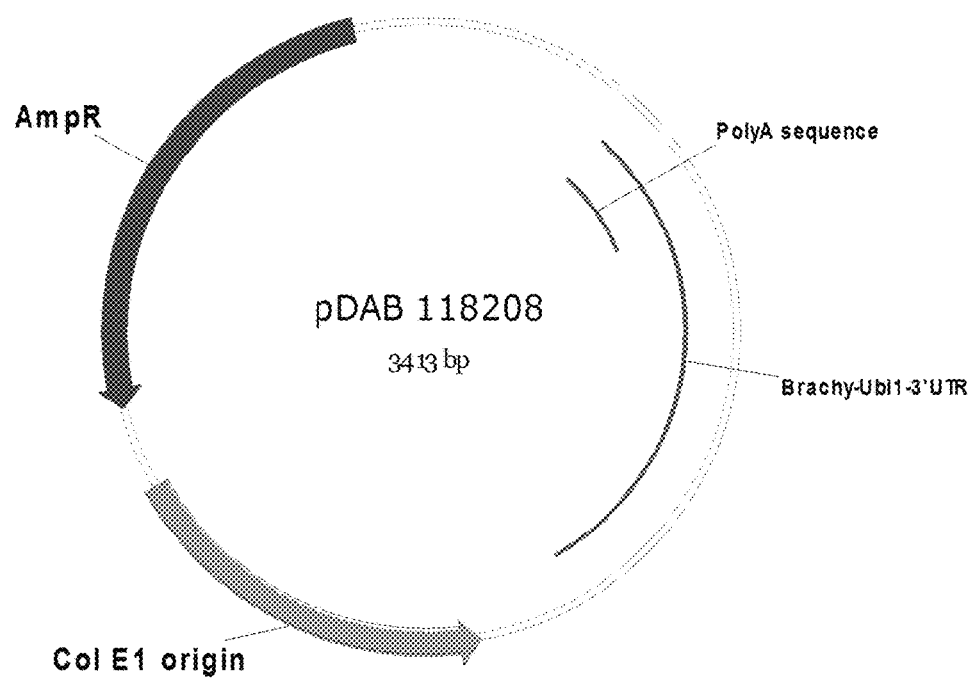
FIG. 25 is plasmid map showing the synthesized *Brachypodium distachyon* Ubiquitin1 3'UTR genetic element and flanking seamless cloning overhang location.
Figure 26:
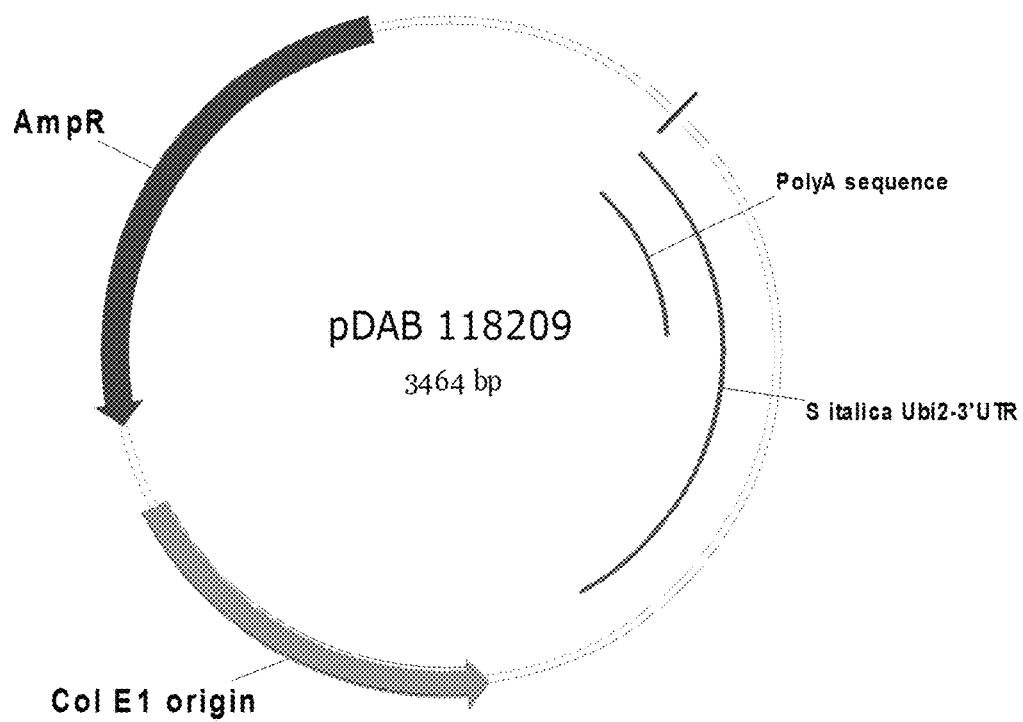
FIG. 26 is plasmid map showing the synthesized *Setaria italica* ubiquitin2 (SI-Ubi2) 3'UTR genetic element and flanking seamless cloning overhang location.
Figure 27:
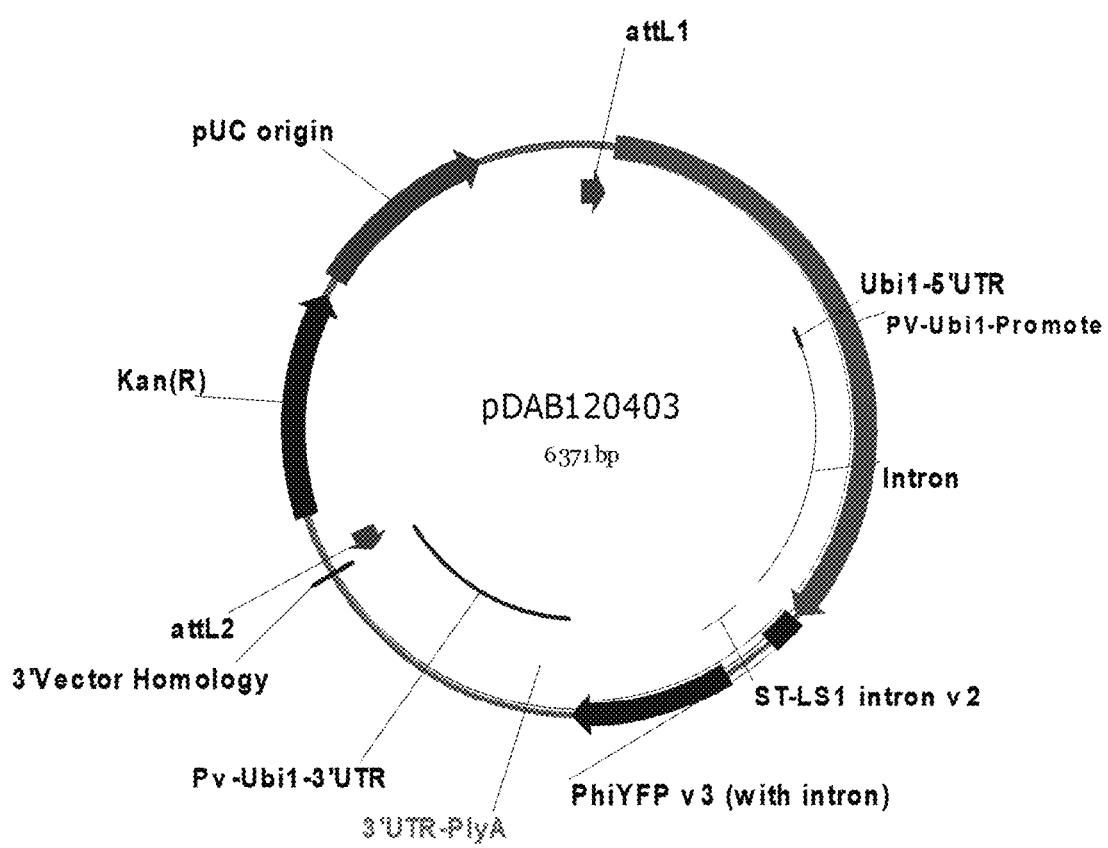
FIG. 27 is plasmid map showing the expression vector containing *Panicum virgatum* Ubiquitin1 promoter and 3'UTR fused to PhiYFP reporter gene.
Figure 28:
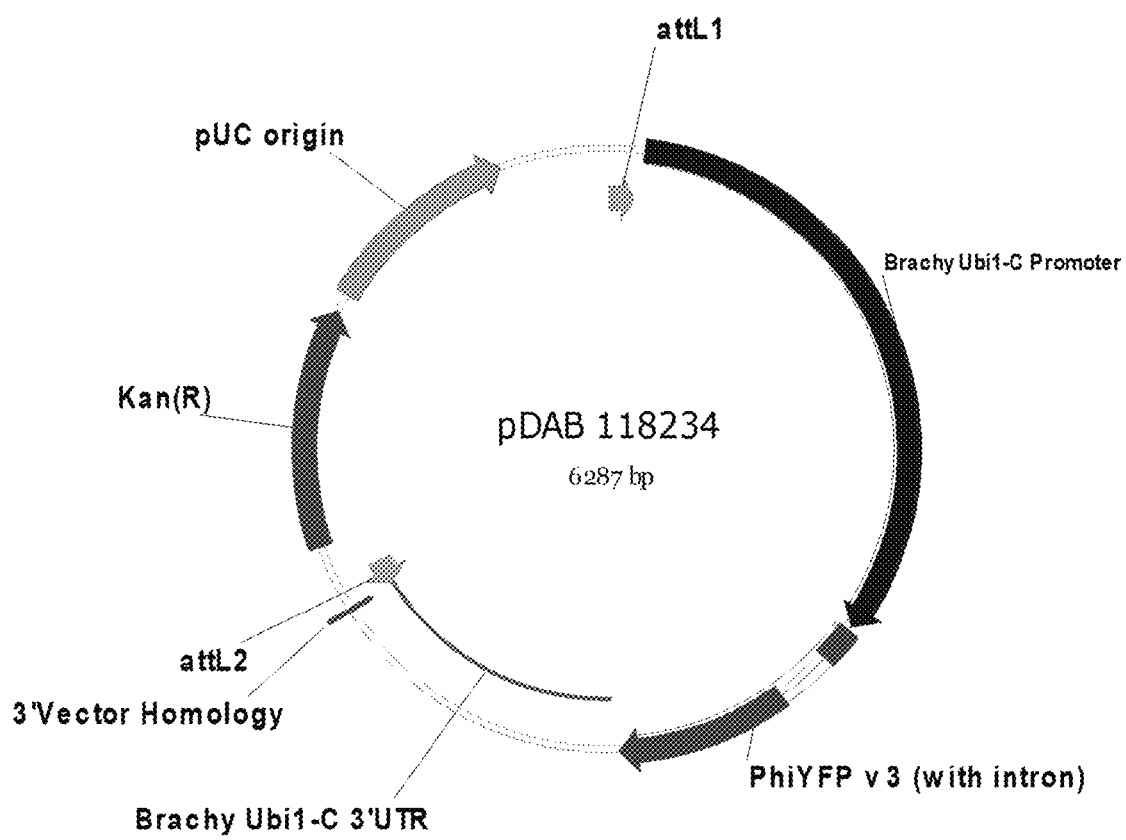
FIG. 28 is plasmid map showing the expression vector containing *Brachypodium distachyon* Ubiquitin1 C promoter and 3'UTR fused to PhiYFP reporter gene.
Figure 29:
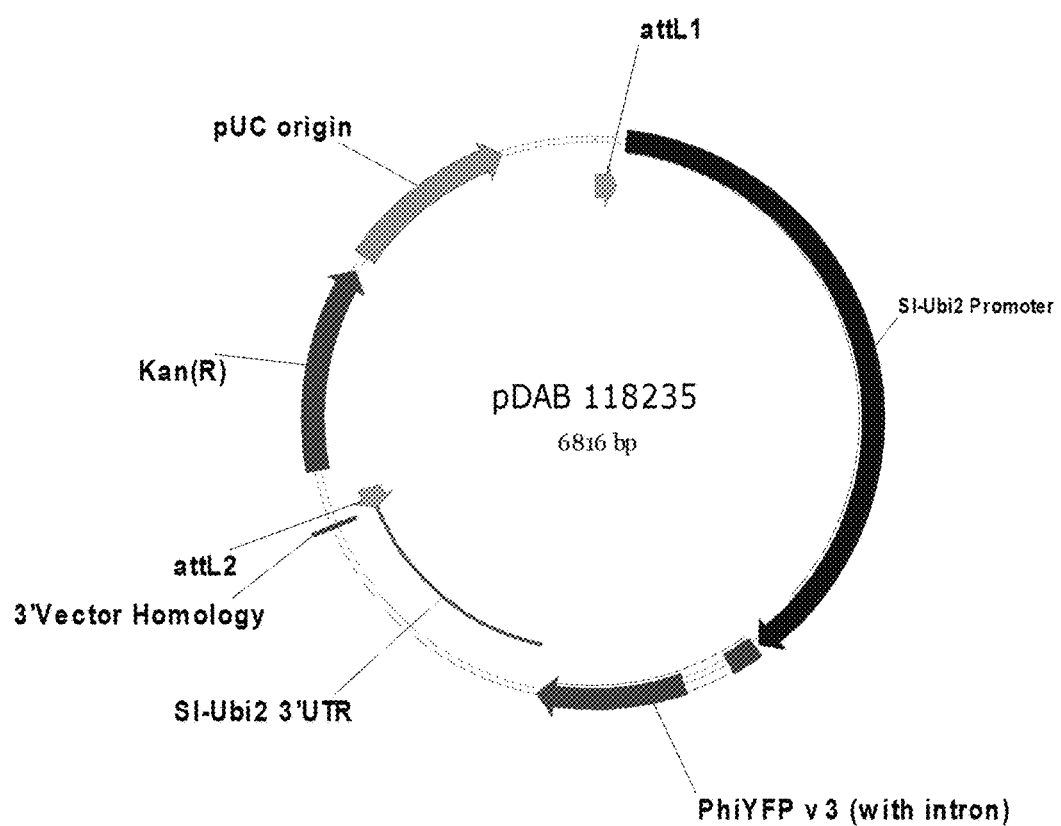
FIG. 29 is a plasmid map showing the expression vector containing *Setaria italica* ubiquitin2 promoter and 3'UTR fused to PhiYFP reporter gene.
Figure 30:
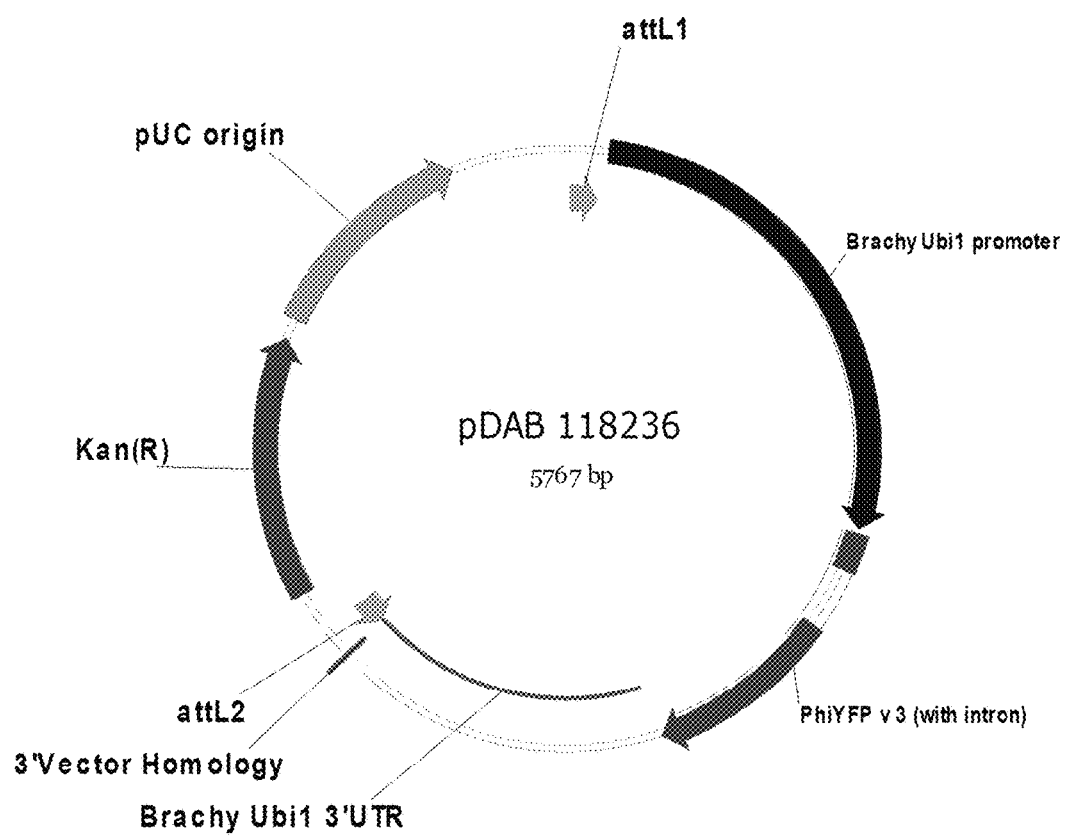
FIG. 30 is plasmid map showing the expression vector containing *Brachypodium distachyon* Ubiquitin1 promoter and 3'UTR fused to PhiYFP reporter gene.
Figure 31:
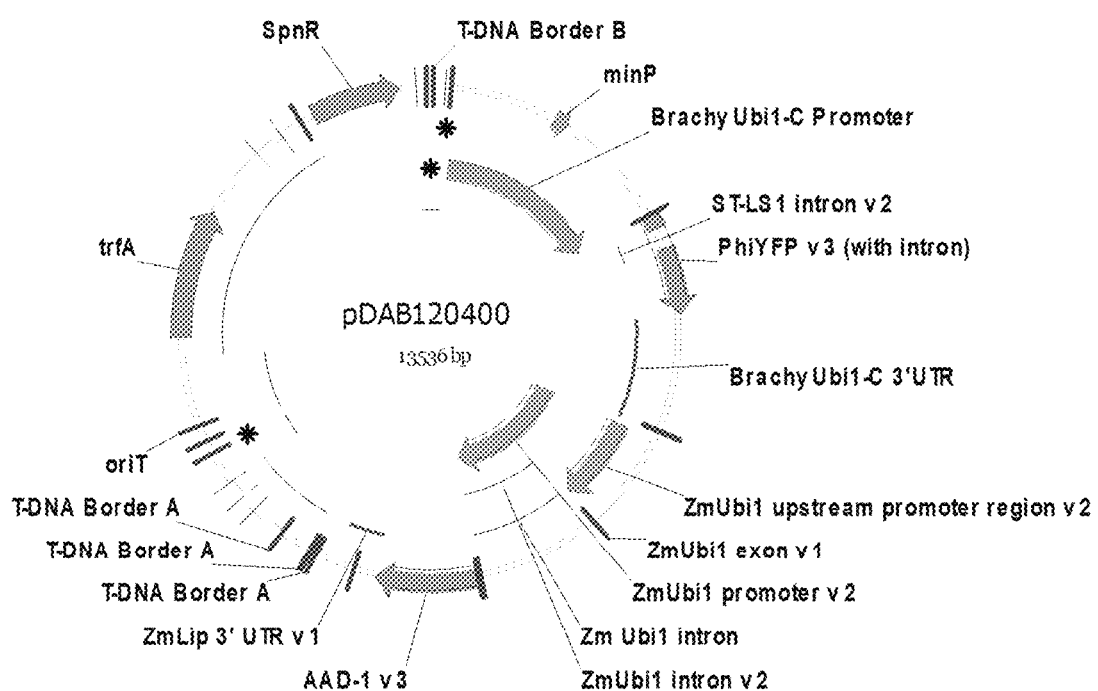
FIG. 31 is a plasmid map showing the binary expression vector containing *Brachypodium distachyon* Ubiquitin1 C promoter fused to yellow fluorescent protein (Phi YFP) marker gene coding region containing ST-LS1 intron followed by fragment comprising a *Brachypodium distachyon* Ubiquitin1 C 3'UTR.
Figure 32:
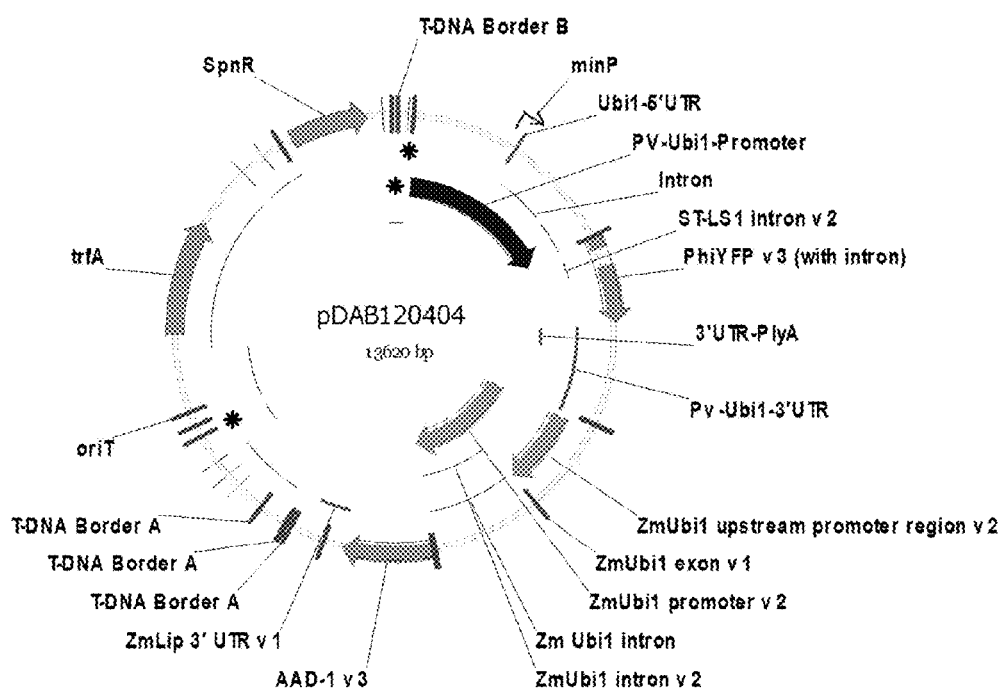
FIG. 32 is a plasmid map showing the binary expression vector containing *Panicum virgatum* Ubiquitin1 promoter fused to yellow fluorescent protein (Phi YFP) marker gene coding region containing ST-LS1 intron followed by fragment comprising a *Panicum virgatum* Ubiquitin1 3'UTR.
Figure 33:
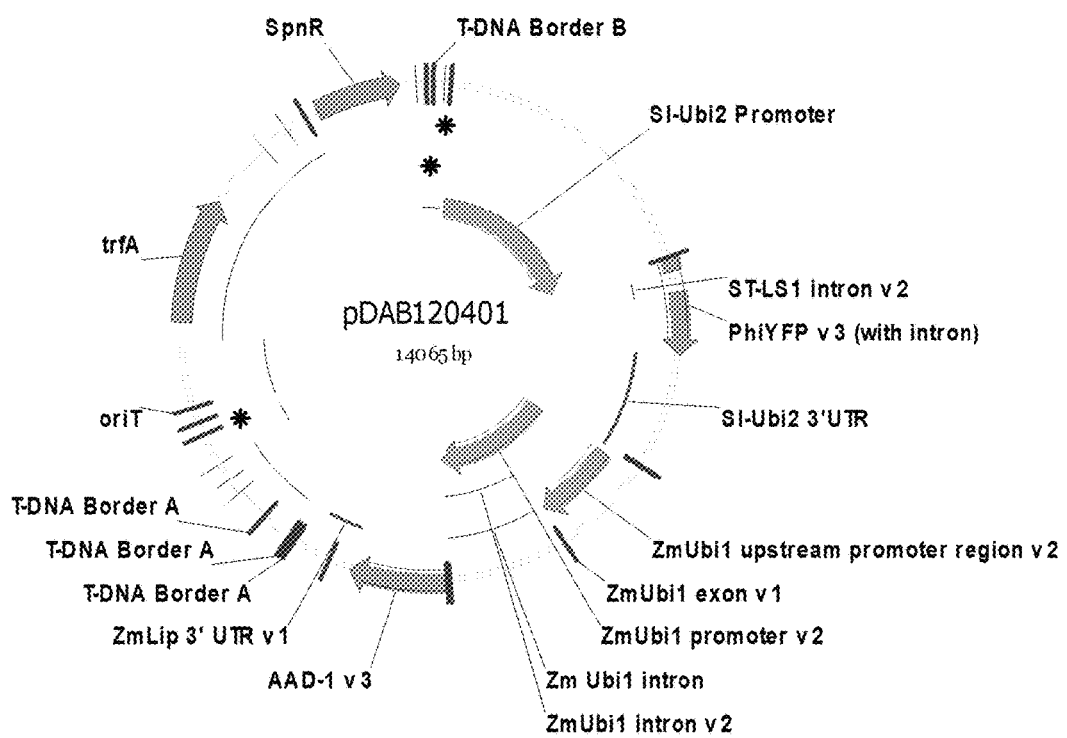
FIG. 33 is a plasmid map showing the binary expression vector containing *Setaria italica* ubiquitin2 promoter fused to yellow fluorescent protein (Phi YFP) marker gene coding region containing ST-LS1 intron followed by fragment comprising a *Setaria italica* ubiquitin2 3'UTR.
Figure 34:
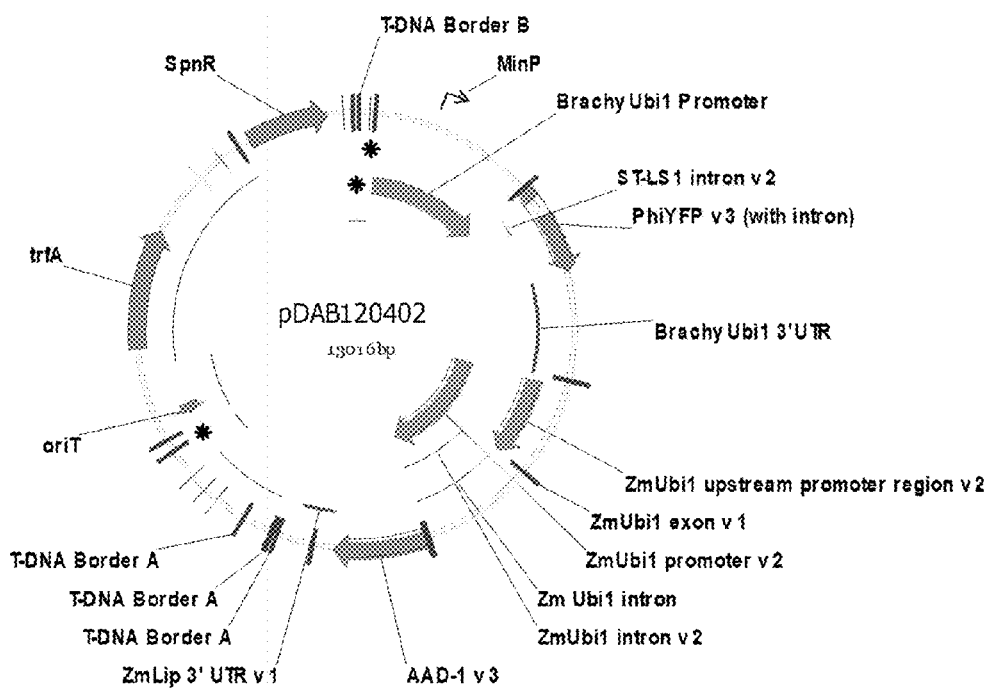
FIG. 34 is a plasmid map showing the binary expression vector containing *Brachypodium distachyon* Ubiquitin1 promoter fused to yellow fluorescent protein (Phi YFP) marker gene coding region containing ST-LS1 intron followed by fragment comprising a *Brachypodium distachyon* Ubiquitin1 3'UTR.

The four promoter sequences were commercially synthesized and incorporated into plasmid vectors as depicted in FIG. 3 (pDAB113091), FIG. 4 (pDAB113092), FIG. 5 (pDAB113066) and FIG. 22 (pDAB118238). Similarly four 3'UTR/transcription termination sequences were commercially synthesized and incorporated into plasmid vectors as depicted in FIG. 23 (pDAB118237), FIG. 24 (pDAB118207), FIG. 25 (pDAB118208) and FIG. 26 (pDAB118209). The sequences were flanked by 15-18 nucleotide homology fragments on both ends for seamless cloning (GeneArt® Seamless Cloning and Assembly Kit, Invitrogen, Carlsbad, Calif.) and type II restriction enzyme sites inserted for the isolation of promoter fragments. Seamless cloning compatible *Zea mays* Ubi1 promoter (Christensen and Quail (1996) Transgenic Research. 5; 213-218; Christensen et al., (1992) Plant Molecular Biology. 18; 675-689) or *Oryzae sativa* Actin promoter (McElroy et al., (1990) Plant Cell. 2; 163-71), and PhiYFP (Shagin et al., (2004) Mol Biol Evol. 21; 841-50) coding sequence comprising the ST-LS1 intron (Vancanneyt et al., (1990) Mol Gen Genet. 220; 245-50), and St PinII or native 3'-UTR (An et al., 1989 Plant Cell. 1; 115-22.) fragments were obtained using PCR or typeII restriction enzymes. Finally, the promoter::PhiYFP::St PinII 3'-UTR fragments were assembled using seamless cloning to create transient expression vectors (FIG. 6, pDAB113103; FIG. 7, pDAB113104; FIG. 8, pDAB113105; FIG. 9, pDAB113106; and, FIG. 10, pDAB113107; FIG. 27, pDAB120403; FIG. 28, pDAB118234, FIG. 29, pDAB118235; and FIG. 30, pDAB118236) for transient expression testing. These transient expression vectors were integrated into a binary vector containing the Zm Ubi 1 promoter and AAD-1 coding sequence (International Patent Publication No. 2005107437) and Zm Lip 3'UTR (Paek et al., (1998) Molecules and Cells, 8(3): 336-342). The resulting binaries were confirmed via restriction enzyme digestion and sequencing reaction (FIG. 12, pDAB113117; FIG. 13, pDAB113118; FIG. 14, pDAB113119; FIG. 15, pDAB113120; FIG. 16, pDAB113121; FIG. 31, pDAB120400; FIG. 32, pDAB120404; FIG. 33, pDAB120401; and, FIG. 34, pDAB120402).

Example 4

Transient Expression Testing

Figure 19:
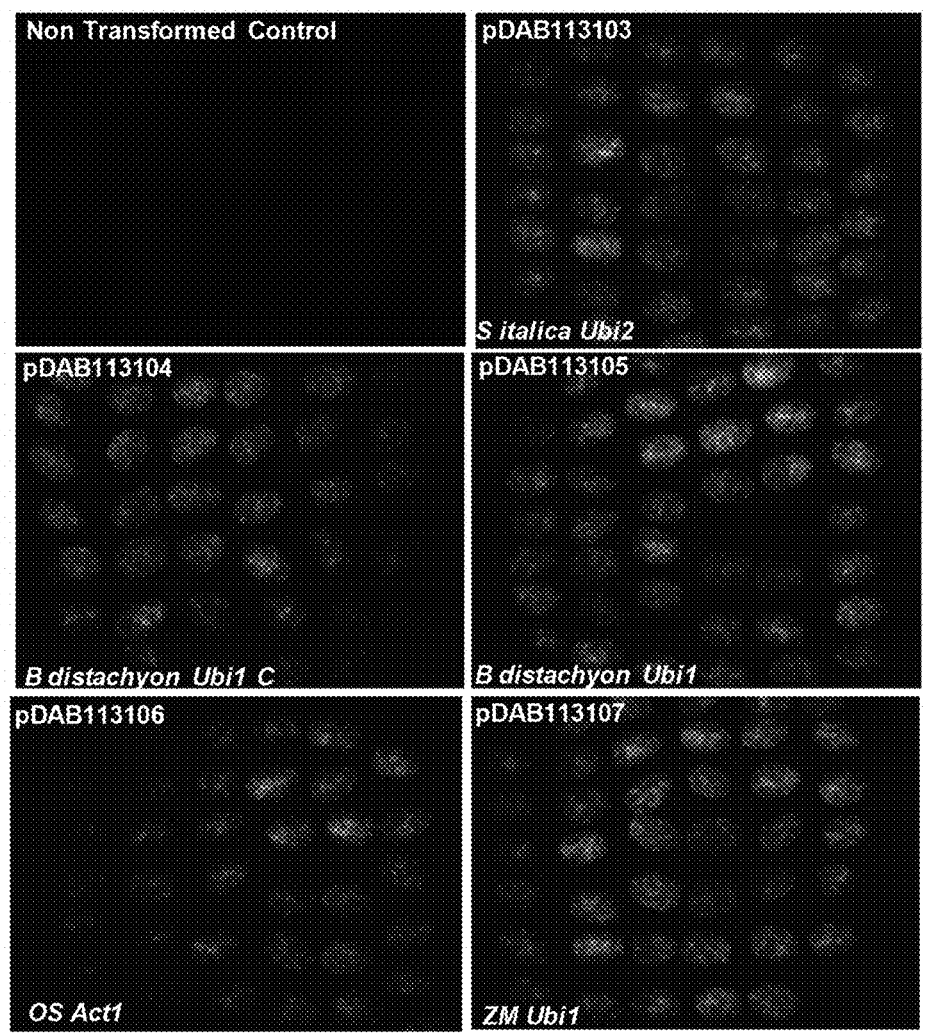
FIG. 19 shows transient YFP expression driven by the *Brachypodium distachyon* and *Setaria italica* novel promoters as compared to YFP expression driven by the ZM Ubi1 and OS Act1 promoters.

Transient expression was tested using particle bombardment of immature maize (B104) embryos. Forty embryos were used per treatment in a Petri plate for bombardment. YFP image analysis was done after overnight incubation of particle bombardment. FIG. 19 shows YFP expression levels obtained from the novel promoters. The data show that YFP expression levels obtained from the novel promoters (pDAB113103, pDAB113104, and pDAB113105) is comparable to the YFP expression levels obtained from the ZM Ubi1 promoter (pDAB113106) and the OS Act 1 promoter (pDAB113107) as visually observed under the microscope. Plant tissues were imaged on a Leica EL6000—mercury metal Halide™ microscope. Confocal and Differential Interference Contrast (DIC) images were captured using Chroma 42003-ZsYellow 1™ filters.

Example 5

Transgene Copy Number Estimation Using Real Time TaqMan® PCR

The stable integration of the yfp transgene within the genome of the transgenic Z. mays plants was confirmed via a hydrolysis probe assay. Stably-transformed transgenic Z. mays plantlets that developed from the callus were obtained and analyzed to identify events that contained a low copy number (1-2 copies) of full-length T-strand inserts. Identified plantlets were advanced to the green house and grown.

The Roche Light Cycler480™ system was used to determine the transgene copy number. The method utilized a biplex TaqMan® reaction that employed oligonucleotides specific to the yfp gene and to the endogenous Z. mays reference gene, invertase (Genbank Accession No: U16123.1), in a single assay. Copy number and zygosity were determined by measuring the intensity of yfp-specific fluorescence, relative to the invertase-specific fluorescence, as compared to known copy number standards.

A yfp gene-specific DNA fragment was amplified with one TaqMan® primer/probe set containing a probe labeled with FAM™ fluorescent dye, and invertase was amplified with a second TaqMan® primer/probe set containing a probe labeled with HEX™ fluorescence (TABLE 2). The PCR reaction mixture was prepared as set forth in TABLE 3, and the gene-specific DNA fragments were amplified according to the conditions set forth in TABLE 4. Copy number and zygosity of the samples were determined by measuring the relative intensity of fluorescence specific for the reporter gene, yfp, to fluorescence specific for the reference gene, invertase, as compared to known copy number standards.

TABLE 2

Forward and reverse nucleotide primer and fluorescent probes.

| Primer/Probe | Sequence |
| --- | --- |
| PhiYFP v3 Forward Primer | (SEQ ID NO: 28) CGTGTTGGGA AAGAACTTGGA |
| PhiYFP v3 Reverse Primer | (SEQ ID NO: 29) CCGTGGTTG GCTTGGTCT |
| PhiYFP v3 Probe | (SEQ ID NO: 30) 5'FAM/CAC TCCCCACTGCCT/MGB_BHQ_1/3' |
| Invertase Forward Primer | (SEQ ID NO: 31) TGGCGGAC GACGACTTGT |
| Invertase Reverse Primer | (SEQ ID NO: 32) AAAGTTTGG AGGCTGCCGT |
| Invertase Probe | (SEQ ID NO: 33) 5'HEX/ CGAGCAGACCGCCGTGTACTT/ 3BHQ_1/3' |

(synthesized by Integrated DNA Technologies, Coralville, IA).

TABLE 3

Taqman ® PCR reaction mixture.

| Component | Working Concentration | Final Concentration | Volume (μl) |
| --- | --- | --- | --- |
| Water | — | — | 0.5 |
| Roche LightCyler 480 Probes Master Mix | 2X | 1X | 5 |
| PhiYFP v3 F | 10 μM | 400 nM | 0.4 |
| PhiYFP v3 R | 10 μM | 400 nM | 0.4 |
| PhiYFP v3 Probe-FAM | 5 μM | 200 nM | 0.4 |
| Invertase F | 10 μM | 400 nM | 0.4 |
| Invertase R | 10 μM | 400 nM | 0.4 |
| Invertase Probe-Hex | 5 μM | 200 nM | 0.4 |
| Polyvinylpyrrolidone (PVP) | 10% | 0.1% | 0.1 |
| Genomic DNA template | Diluted BioCel DNA (~5 nglul) | ~10 ng/uL | 2 |
| Total reaction volume | — | — | 10.0 |

TABLE 4

Thermocycler conditions for PCR amplification.

| PCR Steps | Temp (° C.) | Time | No. of cycles |
| --- | --- | --- | --- |
| Step-1 | 95 | 10 minutes | 1 |
| Step-2 | 95 | 10 seconds | 40 |
|  | 58 | 35 seconds |  |
|  | 72 | 1 second |  |
| Step-3 | 40 | seconds | 1 |

Standards were created by diluting the vector, pDAB108706, into Z. mays B104 genomic DNA (gDNA) to obtain standards with a known relationship of pDAB108706:gDNA. For example, samples having one; two; and four cop(ies) of vector DNA per one copy of the Z. mays B104 gDNA were prepared. One and two copy dilutions of the pDAB108706 mixed with the Z. mays B104 gDNA standard were validated against a control Z. mays event that was known to be hemizygous, and a control Z. mays event that was known to be homozygous (Z. mays event 278; see PCT International Patent Publication No. WO 2011/022469 A2). A TaqMan® biplex assay that utilizes oligonucleotides specific to the AAD1 gene and oligonucleotides specific to the endogenous *Z. mays* reference gene, invertase, was performed by amplifying and detecting a gene-specific DNA fragment for AAD1 with one TaqMan® primer/probe set containing a probe labeled with FAM fluorescent dye, and by amplifying and detecting a gene-specific DNA fragment for invertase with a second TaqMan® primer/probe set containing a probe labeled with HEX™ fluorescence (TABLE 2). The AAD1 TaqMan® reaction mixture was prepared as set forth in TABLE 3, and the specific fragments were amplified according to the conditions set forth in TABLE 4.

The level of fluorescence that was generated for each reaction was analyzed using the Roche LightCycler® 480 Thermocycler according to the manufacturer's directions. The FAM™ fluorescent moiety was excited at an optical density of 465/510 nm, and the HEX™ fluorescent moiety was excited at an optical density of 533/580 nm. The copy number was determined by comparison of Target/Reference values for unknown samples (output by the LightCycler® 480) to Target/Reference values of four known copy number standards (Null, 1-Copy (hemi), 2-Copy (homo) and 4-Copy). Results from the transgene copy number analysis of transgenic plants obtained via transformation with different promoter constructs are shown in TABLE 5. Only plants with 1-2 copies of the yfp transgene were transferred to the greenhouse for further expression analyses.

TABLE 5

Transgene copy number estimation of the transgenic plants obtained from promoter construct described herein and control constructs.

| Construct | Number of Positive Events | 1-2 Copies of yfp |
|---|---|---|
| pDAB113117 | 32 | 17 |
| pDAB113118 | 26 | 13 |
| pDAB113119 | 30 | 16 |
| pDAB113120 | 43 | 10 |
| pDAB113121 | 36 | 19 |

Example 6

Expression of Genes Operably Linked to Ubiquitin Promoters Protein Extraction $T_0$ plants were sampled at V4-5 using a leaf ELISA assays. Sample were collected in 96-well collection tube plate, and 4 leaf disks (paper hole punch size) were taken for each sample. Two 4.5 mm BBs and 200 µL extraction buffer [1×PBS supplemented with 0.05% Tween®-20 and 0.05% BSA (Millipore Probumin®, EMD Millipore Corp., Billerica, Mass.)] were added to each tube. For AAD1 extraction, the concentration of BSA was increased to 0.5%. Plates were processed in a KLECO bead mill at full speed for 3 minutes. Additional 200 µL of extraction buffer was added to each tube followed by inversion to mix. Plates were spun for 5 minutes at 3000 rpm. Supernatant was transferred to corresponding wells in a deep well 96 stored on ice.
YFP and AAD1 ELISA Procedure Nunc® 96-well Maxi-Sorp Plates (Thermo Fisher Scientific Inc., Rockford, Ill.) were used for ELISA. Plates were coated with mouse monoclonal anti-YFP capture antibody (OriGene Technologies Inc., Rockville, Md.). The antibody was diluted in PBS (1 µg/mL) and 150 µL of diluted PBS was added per well. The plates were incubated overnight at 4° C. The overnight plates were kept at room temperature for 20-30 minutes before washing 4× with 350 µL of wash buffer [1×PBS supplemented with 0.05% Tween®-20 (Sigma-Aldrich, St. Louis, Mo.)]. Plates were blocked with 200 µL per well of blocking buffer [1×PBS supplemented with 0.05% Tween®-20 plus 0.5% BSA (Millipore Probumin®)] for a minimum of 1 hr at +37° C. followed by 4× washing with 350 µL of wash buffer (Tomtec QuadraWash™ 2, Tomtec, Inc., Hamden, Conn.).

For the YFP ELISA, Evrogen recombinant Phi-YFP 1 mg/mL (Axxora LLC, Farmingdale, N.Y.) was used as a standard. A 5-parameter fit standard curve (between the 1 ng/ml and 0.125 ng/ml Standards) was used to ensure all data fall in the linear portion of the curve. 100 µL of standard or sample was added to the well. A minimum 1:4 dilution of sample in the Assay Buffer was used. Plates were incubated for 1 hr at RT on plate shaker (250 rpm; Titer Plate shaker) followed by 4× washing with 350 µL of wash buffer (Tomtec QuadraWash™ 2). About 100 µL of 1 µg/mL Evrogen rabbit polyclonal anti-PhiYFP primary antibody (Axxora) was added to each well. Plates were incubated for 1 hr at room temperature on a plate shaker at 250 rpm followed by 4× washing with 350 µL of wash buffer (Tomtec QuadraWash™ 2). Next, 100 µL of anti-rabbit IgG HRP secondary antibody (Thermo Scientific) diluted 1:5000 in Blocking/Assay buffer, which was added to each well. Plates were incubated for 1 hr at room temperature on plate shaker at 250 rpm followed by 4× washes with 350 µL of wash buffer (Tomtec QuadraWash™ 2). 100 µL of Pierce 1 Step Ultra TMB ELISA (Thermo Scientific) substrate was added in the well with gentle shaking for 10 minutes. Reaction was stopped by adding 50 µL of 0.4N $H_2SO_4$. Absorbance was read at 450 nm with a 650 nm reference filter.

AAD1 expression levels were determined by ELISAs using kits from Acadia BioSciences (Portland, Me.). The ELISAs were performed using multiple dilutions of the extracts and using the reagents and instructions provided by the supplier. The protein levels were normalized using total soluble protein assay, performed using the 660 nm protein assay reagent supplied by Thermo Scientific and following the supplier's instructions.

Example 7

Figure 20:
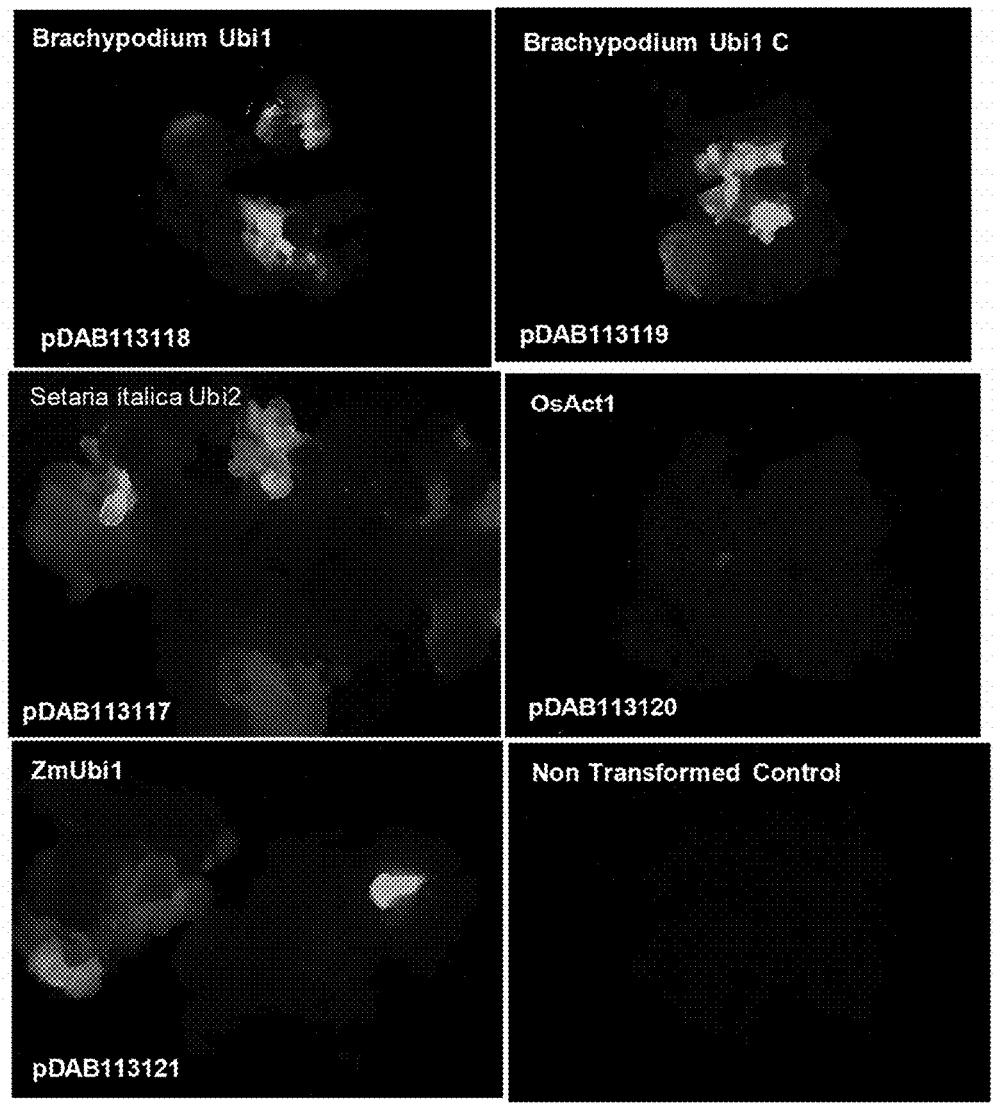
FIG. 20 shows YFP expression in calli tissues driven by the novel *Brachypodium distachyon* and *Setaria italica* promoters as compared to YFP expression driven by the ZM Ubi1 and OS Act1 promoters.
Figure 21:
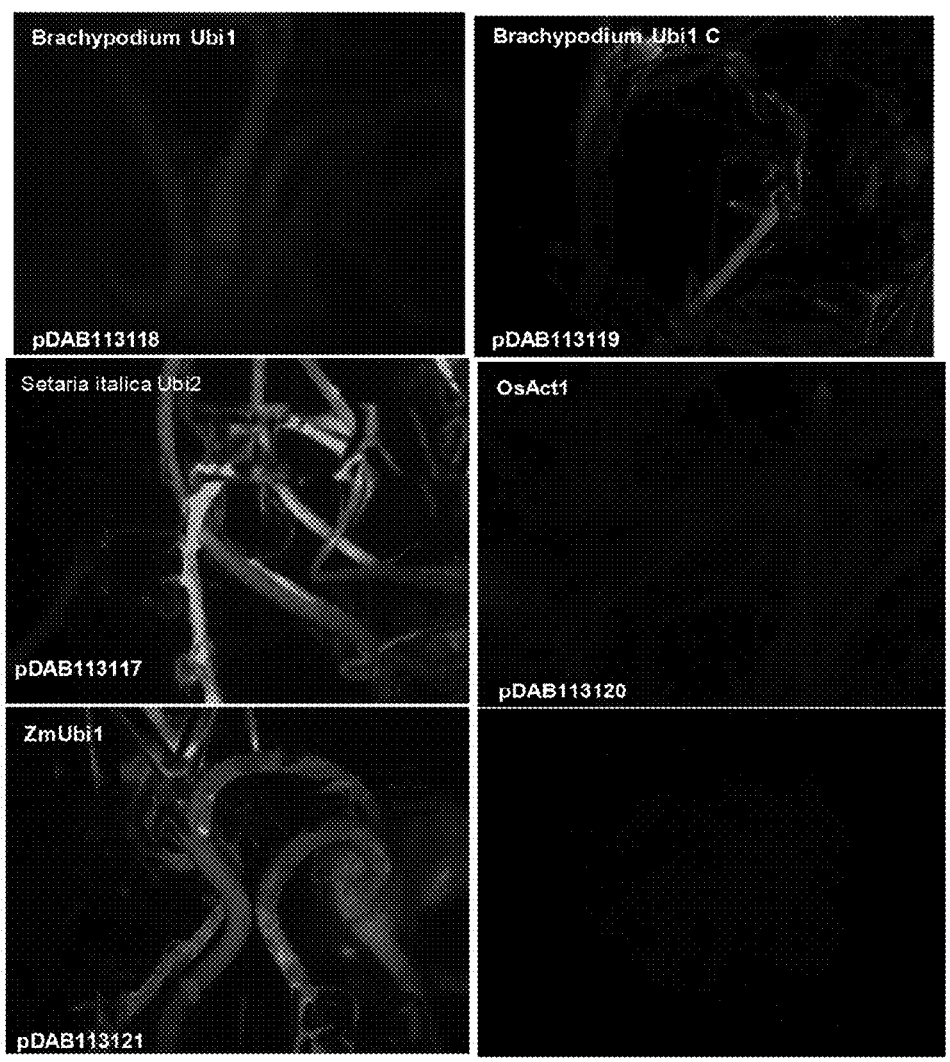
FIG. 21 shows YFP expression in root tissue driven by the novel *Brachypodium distachyon* and *Setaria italica* promoters as compared to YFP expression driven by the ZM Ubi1 and OS Act1 promoters.

Whole Plant YFP Image Analysis Exemplifying Stable Expression of Genes Operably Linked to Ubiquitin Promoters Whole plants that contained a low copy number of the binary plasmid were grown in a greenhouse. Plant tissues were imaged on a Leica EL6000-mercury metal Halide™ microscope. Confocal and Differential Interference Contrast (DIC) images were captured using Chroma 42003-ZsYellow 1™ filters. Representative examples of stable expression of YFP in callus and root tissue of transgenic $T_0$ maize plants obtained from *Z. mays* embryos transformed with the *Brachypodium distachyon* Ubiquitin1 C, *Brachypodium distachyon* Ubiquitin1, and *Setaria italica* ubiquitin 2 promoters described herein are presented in FIG. 20 to FIG. 21, respectively. The promoters drove robust expression of the yfp coding sequences both in callus (FIG. 20) and root (FIG. 21) plant tissues.

Example 8

Figure 17:
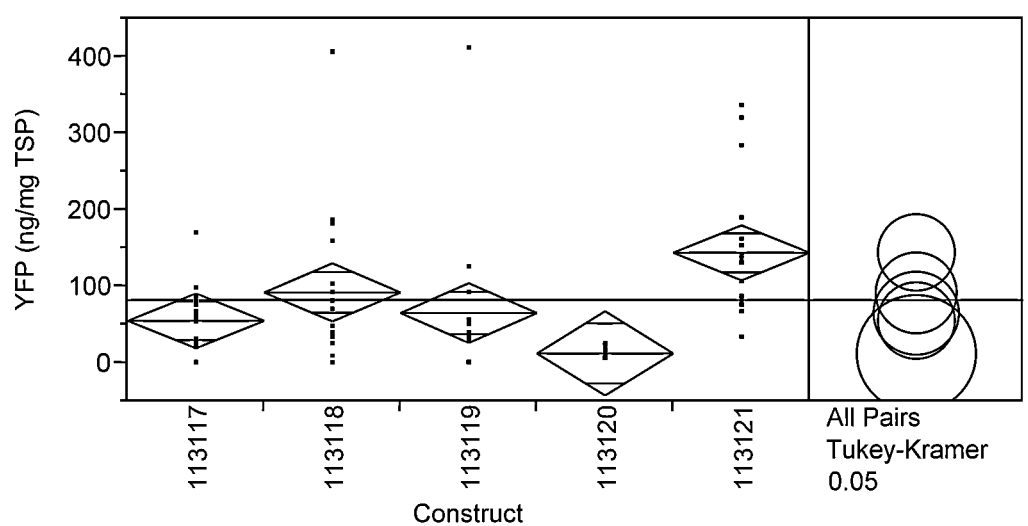
FIG. 17 shows YFP expression in a $T_0$ leaf where YFP is driven by the cross species ubiquitin and Os Act 1 promoters as depicted in FIGS. 12, 13, 14, 15, and 16.
Figure 18:
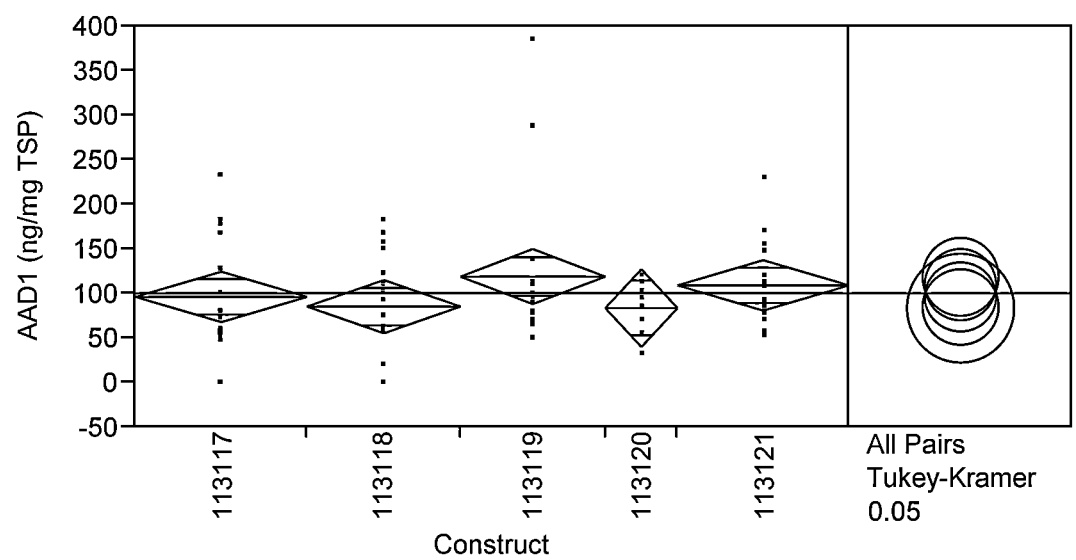
FIG. 18 shows AAD1 expression in a $T_0$ leaf where AAD1 is driven by the Zm Ubi 1 promoter as depicted in FIGS. 12, 13, 14, 15, and 16.

Whole Plant $T_0$ Stable Expression of Genes Operably Linked to Ubiquitin Promoters Additional data was produced from an ELISA analysis of the expressed YFP protein. The ELISA analysis further confirmed that the novel promoters drove robust expression of a transgene. The quantitative measurements of YFP protein obtained from transgenic plants comprising novel promoter constructs are shown in FIG. 17 and TABLE 6. The data show that expression of YFP protein in the plants containing the novel promoters (pDAB113117, pDAB113118, and pDAB113119) is several fold higher that YFP expression obtained from the Os Act1 (Rice Actin1) promoter (pDAB113120). Comparatively, FIG. 18 and TABLE 7 show that similar level of AAD1 expression was obtained from all the constructs. This is expected because AAD1 is driven by the Zm Ubi1 promoter for all of the constructs.

TABLE 6

Cross Species Ubiquitin Promoter $T_0$ Leaf YFP expression

| Construct | Mean (ng/mg TSP) | Statistical significance |
|---|---|---|
| pDAB113121 | 144.00173 | A |
| pDAB113118 | 92.37256 | AB |
| pDAB113119 | 65.30393 | B |
| pDAB113117 | 55.24345 | B |
| pDAB113120 | 12.77181 | B |

Levels not connected by same letter are significantly different

TABLE 7

Cross Species Ubiquitin Promoter $T_0$ Leaf AAD1 expression

| Construct | Mean (ng/mg TSP) | Statistical significance |
|---|---|---|
| pDAB113121 | 119.06932 | A |
| pDAB113118 | 109.19796 | A |
| pDAB113119 | 96.29021 | A |
| pDAB113117 | 85.40412 | A |
| pDAB113120 | 83.81594 | A |

Levels not connected by same letter are significantly different

Example 9

Whole Plant $T_1$ Stable Expression of Genes Operable Linked to Ubiquitin Promoters and 3'UTRs $T_0$ single transgene copy plants were backcrossed to wild type B104 corn plants to obtain $T_1$ seed. Hemizygous $T_1$ plants were used for analysis. Five events per construct and 5-10 plants per event for V4 and V12 leaf expression. Three events per construct and 3 plants per event were used for the other tissue type expression. Zygosity analysis was done for AAD1/YFP.

The quantitative measurements of YFP protein obtained from leaf tissue of $T_1$ transgenic plants comprising novel promoter constructs are shown in TABLE 8. The data confirmed the $T_0$ leaf expression results and further showed that consistent high expression of YFP protein was obtained in the V4, V12 and R3 leaf tissue of the plants containing the novel promoters (pDAB113117, pDAB113118, and pDAB113119). TABLE 8 also shows that there was several fold increase in the expression of YFP protein when this novel promoters were used in combination with their native 3'UTRs (pDAB120400, pDAB120401, and pDAB120402) instead of PinII 3'UTR (pDAB113117, pDAB113118, and pDAB113119). YFP protein expression was detected from the plants containing construct pDAB120404 confirming that novel promoter and 3'UTR used in this construct drive expression of a transgene.

TABLE 8

Cross Species Ubiquitin Promoter and 3'UTR $T_1$ Leaf Expression

| | | Mean YEP (ng/mg TSP) | | |
|---|---|---|---|---|
| Construct | Event | V4 Le | V12 Leaf | R3 Leaf |
| pDAB113117 | pDAB113117[1]-006 | 44.0 | 169.4 | 2108.3 |
| pDAB113117 | pDAB113117[1]-007 | 44.8 | 181.4 | 2582.7 |
| pDAB113117 | pDAB113117[1]-008 | 79.6 | 322.8 | 4096.3 |
| pDAB113117 | pDAB113117[1]-019 | 74.3 | 369.1 | 3420.3 |
| pDAB113117 | pDAB113117[1]-028 | 34.2 | 168.2 | 2164.1 |
| pDAB113118 | pDAB113118[1]-005 | 33.6 | 148.8 | 2094.7 |
| pDAB113118 | pDAB113118[1]-007 | 54.9 | 180.1 | 2171.4 |
| pDAB113118 | pDAB113118[1]-010 | | 138.0 | 2748.2 |
| pDAB113118 | pDAB113118[1]-023 | 46.2 | 156.6 | 2216.8 |
| pDAB113118 | pDAB113118[1]-025 | 41.7 | 132.9 | 2071.4 |
| pDAB113119 | pDAB113119[1]-001 | 133.1 | 436.0 | 6744.0 |
| pDAB113119 | pDAB113119[1]-005 | 49.2 | 138.6 | 1772.9 |
| pDAB113119 | pDAB113119[1]-011 | 54.6 | 133.9 | 1415.5 |
| pDAB113119 | pDAB113119[1]-013 | | 129.1 | 1807.7 |
| pDAB113119 | pDAB113119[1]-028 | 38.5 | 129.9 | 1632.8 |
| pDAB113120 | pDAB113120[1]-005 | 9.8 | 69.6 | 493.5 |
| pDAB113120 | pDAB113120[1]-010 | 24.3 | 74.5 | 638.3 |
| pDAB113120 | pDAB113120[1]-014 | 17.2 | 79.7 | 552.4 |
| pDAB113120 | pDAB113120[1]-023 | 13.2 | 55.4 | 372.2 |
| pDAB113120 | pDAB113120[1]-032 | 12.5 | 69.6 | 233.7 |
| pDAB113121 | pDAB113121[1]-008 | 327.9 | | |
| pDAB113121 | pDAB113121[1]-011 | 166.2 | 271.2 | 4472.6 |
| pDAB113121 | pDAB113121[1]-018 | 128.2 | 362.0 | 7116.3 |
| pDAB113121 | pDAB113121[1]-023 | 112.2 | 309.1 | 6813.7 |
| pDAB113121 | pDAB113121[1]-026 | 118.7 | 311.7 | 6300.7 |
| pDAB120400 | pDAB120400[1]-001 | 640.8182 | | |
| pDAB120400 | pDAB120400[1]-002 | 339.24463 | | |
| pDAB120400 | pDAB120400[1]-004 | 943.96511 | | |
| pDAB120400 | pDAB120400[1]-007 | 1653.7402 | | |
| pDAB120400 | pDAB120400[1]-024 | 466.01906 | | |
| pDAB120401 | pDAB120401[1]-001 | 833.04373 | | |
| pDAB120401 | pDAB120401[1]-011 | 471.9103 | | |
| pDAB120401 | pDAB120401[1]-019 | 795.08285 | | |
| pDAB120401 | pDAB120401[1]-022 | 721.58288 | | |
| pDAB120401 | pDAB120401[1]-025 | 696.94286 | | |
| pDAB120402 | pDAB120402[1]-010 | 750.82185 | | |
| pDAB120402 | pDAB120402[1]-011 | 619.38603 | | |
| pDAB120402 | pDAB120402[1]-014 | 618.98144 | | |
| pDAB120402 | pDAB120402[1]-030 | 625.84385 | | |
| pDAB120404 | pDAB120404[1]-003 | 44.088479 | | |
| pDAB120404 | pDAB120404[1]-013 | 47.464389 | | |
| pDAB120404 | pDAB120404[1]-014 | 52.204801 | | |
| pDAB120404 | pDAB120404[1]-016 | 45.397854 | | |
| pDAB120404 | pDAB120404[1]-020 | 46.913279 | | |

High YFP protein expression was found in different tissue types including cob, husk, kernel, pollen, root, silk and stem sampled from the transgenic corn plants containing novel Ubiquitin Promoters driving YFP (Table 9). These data demonstrate that the novel promoters and 3'UTRs claimed here drive high constitutive expression of transgene in plants and would be useful for biotechnological applications.

TABLE 9

Cross Species Ubiquitin Promoter T1 Expression in Different Tissue Type

| | | Mean YFP (ng/mg TSP) | | | | | | |
|---|---|---|---|---|---|---|---|---|
| Construct | Event | Cob | Husk | Kernel | Pollen | V12 Root | Silk | Stem |
| pDAB113117 | pDAB113117[1]-006 | 3452.1 | 1164.3 | 1341.2 | 397.1 | 2292.7 | 1405.0 | 7279.8 |
| pDAB113117 | pDAB113117[1]-007 | 2519.6 | 954.7 | 1410.9 | 414.3 | 2245.6 | 1974.3 | 6179.0 |
| pDAB113117 | pDAB113117[1]-019 | 8362.3 | 2280.8 | 2829.6 | 749.5 | 7112.4 | 4790.2 | 13044.1 |
| pDAB113118 | pDAB113118[1]-005 | 2801.6 | 620.9 | 886.3 | 782.2 | 1136.1 | 636.7 | 1953.6 |
| pDAB113118 | pDAB113118[1]-007 | 2339.2 | 524.9 | 725.1 | 376.1 | 1495.6 | 1271.0 | 2806.9 |
| pDAB113118 | pDAB113118[1]-023 | 1302.1 | 491.8 | 716.8 | 435.3 | 1193.0 | 829.1 | 1522.9 |
| pDAB113119 | pDAB113119[1]-011 | | | | 399.7 | 1025.9 | 942.2 | 2475.6 |
| pDAB113119 | pDAB113119[1]-013 | 2238.1 | 572.0 | 1050.5 | 438.1 | 1311.2 | 539.7 | 2235.2 |
| pDAB113119 | pDAB113119[1]-028 | 2013.9 | 536.4 | 1061.4 | 450.0 | 1166.3 | 826.9 | 1912.5 |
| pDAB113120 | pDAB113120[1]-005 | 1166.8 | 310.5 | 514.0 | 1704.1 | 169.7 | 322.1 | 739.3 |
| pDAB113120 | pDAB113120[1]-023 | 1096.4 | 531.9 | 845.8 | 1433.9 | 268.4 | 572.2 | 877.9 |
| pDAB113120 | pDAB113120[1]-032 | 1344.1 | 587.8 | 985.1 | 1252.3 | 187.6 | 472.4 | 694.0 |
| pDAB113121 | pDAB113121[1]-011 | 6779.1 | 2942.3 | 3452.6 | 2022.6 | 5834.0 | 2881.7 | 7445.5 |
| pDAB113121 | pDAB113121[1]-023 | 4830.0 | 2689.8 | 1913.7 | 1641.8 | 2547.7 | 2453.8 | 8295.9 |
| pDAB113121 | pDAB113121[1]-026 | 8186.2 | 3889.3 | 4432.3 | 1432.0 | 2521.9 | 2182.5 | 7760.7 |

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

What is claimed:

1. A nucleic acid vector comprising a promoter, wherein
   i) said promoter is operably linked to a polylinker sequence;
   ii) said promoter is operably linked to a non-ubiquitin-coding sequence or
   iii) said promoter is operably linked to a sequence comprising a polylinker sequence and a non-ubiquitin-coding sequence, wherein said promoter comprises SEQ ID NO: 2 or a sequence that has at least 99% sequence identity with SEQ ID NO: 2 and can initiate transcription of an operably linked coding sequence.

2. The nucleic acid vector of claim 1 wherein said promoter is less than 3 kb in length.

3. The nucleic acid vector of claim 1 wherein said promoter consists of SEQ ID NO: 2.

4. The nucleic acid vector of claim 1 further comprising a sequence encoding a selectable marker.

5. The nucleic acid vector of claim 4 wherein said promoter is operably linked to a transgene.

6. The nucleic acid vector of claim 5 wherein the transgene encodes a selectable marker or a gene product conferring insecticidal resistance, herbicide tolerance, nitrogen use efficiency, water use efficiency, or nutritional quality.

7. The nucleic acid vector of claim 1 further comprising a 3' untranslated sequence comprising SEQ ID NO: 5 or a sequence that has at least 99% sequence identity with SEQ ID NO: 5, wherein the 3' untranslated sequence is operably linked to said polylinker or said coding sequence.

8. The nucleic acid vector of claim 1 further comprising a 5' untranslated sequence comprising SEQ ID NO: 12 or a sequence that has at least 99% sequence identity with SEQ ID NO: 12, wherein the 5' untranslated sequence is inserted between, and operably linked to, said promoter sequence and said polylinker or said coding sequence.

9. The nucleic acid vector of claim 8 further comprising an intron sequence inserted after the 5' untranslated sequence.

10. The nucleic acid vector of claim 9 wherein the intron sequence comprises SEQ ID NO: 8.

11. The nucleic acid vector of claim 1 wherein the promoter consists of SEQ ID NO: 40 or a sequence having at least 99% sequence identity with SEQ ID NO: 40, said promoter being operably linked to said polylinker or said coding sequence, wherein said promoter can initiate transcription of the operably linked coding sequence.

12. The nucleic acid vector of claim 1 wherein the promoter consists of SEQ ID NO: 16 or a sequence having at least 99% sequence identity with SEQ ID NO: 16, and said promoter being operably linked to said polylinker or said coding sequence, wherein said promoter can initiate transcription of the operably linked coding sequence.

13. The nucleic acid vector of claim 12 further comprising a 3' untranslated sequence comprising SEQ ID NO: 5 or a sequence that has at least 99% sequence identity with SEQ ID NO: 5, wherein the 3' untranslated sequence is operably linked to said polylinker or said coding sequence.

14. A non-*Brachypodium* plant comprising a *Brachypodium* promoter, wherein said *Brachypodium* promoter comprises SEQ ID NO: 2, or a sequence that has at least 99% sequence identity with SEQ ID NO: 2, operably linked to a coding sequence wherein said *Brachypodium* promoter can initiate transcription of the operably linked coding sequence.

15. The plant of claim 14 wherein said plant is selected from the group consisting of maize, wheat, rice, sorghum, oats, rye, bananas, sugar cane, soybean, cotton, sunflower, and canola.

16. The plant of claim 14 wherein said plant is *Zea mays*.

17. The plant of claim 16 wherein the operably linked coding sequence is a transgene, further wherein said transgene is inserted into the genome of said plant.

18. The plant of claim 14 further comprising a 5' untranslated sequence comprising SEQ ID NO: 12 or a sequence that has at least 99% sequence identity with SEQ ID NO: 12, wherein the 5' untranslated sequence is inserted between, and operably linked to, said *Brachypodium* promoter and said coding sequence.

19. The plant of claim 18 further comprising an intron sequence inserted after the 5' untranslated sequence.

20. The plant of claim 19 wherein the intron sequence comprises SEQ ID NO: 8.

21. The plant of claim 18 further comprising a 3' untranslated sequence comprising SEQ ID NO: 5 or a sequence that has at least 99% sequence identity with SEQ ID NO: 5, wherein the 3' untranslated sequence is operably linked to said coding sequence.

22. The plant of claim 14 wherein the *Brachypodium* promoter consists of SEQ ID NO: 40 or a sequence having at least 99% sequence identity with SEQ ID NO: 40 and can initiate transcription of the operably linked coding sequence, further wherein said promoter is operably linked to a transgene.

23. The plant of claim 14 wherein the *Brachypodium* promoter consists of SEQ ID NO: 16 or a sequence having at least 99% sequence identity with SEQ ID NO: 16 and can initiate transcription of the operably linked coding sequence, further wherein said promoter is operably linked to a transgene.

24. The plant of claim 23 further comprising a 3' untranslated sequence comprising SEQ ID NO: 5 or a sequence that has at least 99% sequence identity with SEQ ID NO: 5, wherein the 3' untranslated sequence is operably linked to said transgene.

25. A nucleic acid vector comprising a transcription terminator, wherein
  i) said terminator is operably linked to a polylinker sequence;
  ii) said terminator is operably linked to a non-ubiquitin-coding sequence; or
  iii) said terminator is operably linked to a sequence comprising a polylinker sequence and a non-ubiquitin-coding sequence, wherein said transcription terminator comprises SEQ ID NO: 5 or a sequence that has at least 99% sequence identity with SEQ ID NO: 5.

26. The nucleic acid vector of claim 25 wherein said transcription terminator consists of SEQ ID NO: 5.

* * * * *